United States Patent
Maury et al.

(10) Patent No.: US 10,696,694 B2
(45) Date of Patent: Jun. 30, 2020

(54) LANTHANIDE COMPLEXES FOR CRYSTALLISING BIOLOGICAL MACROMOLECULES AND DETERMINING THE CRYSTALLOGRAPHIC STRUCTURE THEREOF

(71) Applicants: ECOLE NORMALE SUPERIEURE DE LYON, Lyons (FR); UNIVERSITE CLAUDE BERNARD LYON I, Villeurbanne (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

(72) Inventors: Oliver Maury, Brindas (FR); Eric Girard, Romans sur Isere (FR); Sylvain Engilberge, Reignier (FR); François Riobe, Lyons (FR)

(73) Assignees: ECOLE NORMALE SUPERIEURE LE LYON, Lyons (FR); UNIVERSITE CLAUDE BERNARD LYON I, Villeurbanne (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/061,691

(22) PCT Filed: Dec. 16, 2016

(86) PCT No.: PCT/FR2016/053539
§ 371 (c)(1),
(2) Date: Jun. 13, 2018

(87) PCT Pub. No.: WO2017/103545
PCT Pub. Date: Jun. 22, 2017

(65) Prior Publication Data
US 2018/0362550 A1 Dec. 20, 2018

(30) Foreign Application Priority Data
Dec. 18, 2015 (FR) ...................... 15 62880

(51) Int. Cl.
*C07F 5/00* (2006.01)
*G01N 23/22* (2018.01)
(Continued)

(52) U.S. Cl.
CPC .............. *C07F 5/003* (2013.01); *B01D 9/005* (2013.01); *C07D 401/14* (2013.01);
(Continued)

(58) Field of Classification Search
CPC ................................ C07F 5/00; C07D 401/14
See application file for complete search history.

(56) References Cited

U.S. PATENT DOCUMENTS

2010/0247448 A1* 9/2010 Gateau ................. A61K 49/103
424/9.363

FOREIGN PATENT DOCUMENTS

| FR | 2 991 322 | 12/2013 |
|----|-----------|---------|
| WO | 02/088435 | 11/2002 |
| WO | 2014/162105 | 10/2014 |

OTHER PUBLICATIONS

James W. Walton et al., Isostructural Series of Nine-Coordinate Chiral Lanthanide Complexes Based on Triazacyclononane, Inorg. Chem, 51(15), 8042-8056. (Year: 2012).*

(Continued)

*Primary Examiner* — Michael G. Hartley
*Assistant Examiner* — Jagadishwar R Samala
(74) *Attorney, Agent, or Firm* — Clark & Brody LP

(57) ABSTRACT

The invention relates to cationic complexes made up of a lanthanide ion Ln3+ and a ligand of formula (I):

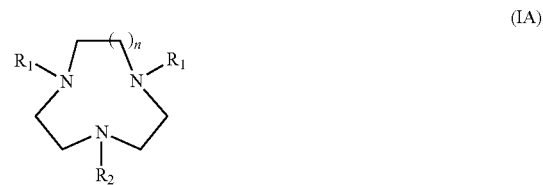

(IA)

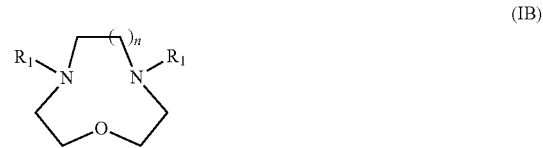

(IB)

(IC)

(ID)

(Continued)

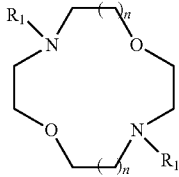

(IE)

with X, Y and R1 as defined in claim 1, and to the salts thereof with an anion, the solvates and hydrates thereof;
with the exception of cationic complexes made up of a lanthanide ion Ln3+ and a ligand of one of formulae (I.1) or (I.4) as defined in claim 1, and the salts, solvates and hydrates thereof. The invention also relates to the use of such a complex or of a cationic complex made up of a lanthanide ion Ln3+ and a ligand of formula (I.1) or (I.4) as defined in claim 1, or of one of the salts thereof with an anion, the solvates or hydrates thereof, as an aid to the crystallisation of a biological macromolecule, as well as to crystallisation methods and methods for analysing or determining the structure of a biological macromolecule.

6 Claims, 8 Drawing Sheets

Specification includes a Sequence Listing.

(51) Int. Cl.
| | |
|---|---|
| C07D 401/14 | (2006.01) |
| G01N 23/223 | (2006.01) |
| C07D 413/14 | (2006.01) |
| B01D 9/00 | (2006.01) |
| C30B 7/14 | (2006.01) |
| C30B 29/58 | (2006.01) |

(52) U.S. Cl.
CPC .............. *C07D 413/14* (2013.01); *C30B 7/14* (2013.01); *C30B 29/58* (2013.01); *G01N 23/223* (2013.01)

(56) References Cited

OTHER PUBLICATIONS

Corneillie et al., "Crystal Structures . . . Chiral System", Journal of the American Chemical Society, American Chemical Society, 2003, vol. 125, No. 49, pp. 15039-15048.
E. Girard et al., "A new class . . . macromolecular crystallography", Acta Crystallographica Section D, 2003, pp. 1914-1922.
Pompidor et al., "Protein Crystallography . . . and Arginine", Angewandte Chemie International Edition, 2008, vol. 47, No. 18, pp. 3388-3391.
Mato-Iglesias et al., "Lanthanide Complexes . . . Contrast Agents", Inorganic Chemistry, American Chemical Society, 2008, vol. 47, pp. 7840-7851.
Palinkas et al., "Stability, Water . . . the Gd Complex", Inorganic Chemistry, American Chemical Society, 2009, vol. 48, pp. 8878-8889.
Inmaculada et al., "Crystallization of . . . lanthanide complexes", Act Crystallographica, 2010, vol. 64, No. 4, pp. 448-451.
Roca-Sabio et al., "The effect of . . . picolinate pendants", Dalton Transactions, Royal Society of Chemistry, 2011, vol. 40, pp. 384-392.
Rodriguez-Rodriguez et al., "Lanthanide (III) Complexes . . . Hydration Number", Inorganic Chemistry, 2012, vol. 51, No. 4, pp. 2509-2521.
Talon et al., "Clicked europium . . . structure determination", Chemical Communications, 2012, vol. 48, No. 997, pp. 3388-3391.
Bijelic et al, "Hen Egg-White . . . Centred Polyoxotungstate", ChemBioChem, 2015, vol. 16, pp. 233-241.
Regueiro-Figueroa et al., "Stabilizing Divalent . . . Electrostatic Effects", Inorg. Chem., 2015, vol. 54, pp. 4940-4952.
K. Allen et al., "Lanthanide-tagged-proteins—an illumination partnership", Current Opinion in Chemical Biology, vol. 14, 2010, pp. 247-254.
D'Arcy et al., "using natural seeding . . . protein crystallization experiments", Biological Crystallography , vol. 59, pp. 1343-1346, 2003.
Dauter et al., "Novel approach . . . with halides" Biological Crystallography, pp. 232-237, 2000.
Dumont et al., "Exploration of the . . . and NMR study" Phys. Chem. Chem. Phys. 2013, vol. 15, pp. 18235-18242.
G. Falini et al., "Protein crystallization . . . mica surfaces", Acta Crystallogr D. Biol. Crystallogr. vol. 58, pp. 1649-1652, 2002.
E. Girard et al., "A new class of . . . from Aspergillus Flavus", Acta Crystallographica, 2003, D59, 118-126.
E. Girard et al., "High-phasing-power lanthanide . . . using synchrotron radiation" Acta Crystallographica, 2003, D59, 1877-1880.
S. Khurshid et al., "Automating the application . . . for protein crystallization", Acta Cryst. D, vol. 71, pp. 534-540, 2015.
R. Matar-Merhab et al., "Structuring Detergents . . . Membrane Proteins", PloS ONE, Mar. 2011, vol. 6.
A. McPherson et al., "Heterogeneous and . . . Mineral Surfaces" Science, vol. 239, pp. 385-387, 1988.
R. Nagem et al., "Protein crystal . . . anomalous scatterers", Acta Crystallographica D, D57, pp. 996-1002, 2001.
E. Pechkova et al., "Protein Nucleation . . . Film Template", Journal of Cellular Biochemistry 85:243-251 (2002).
M. Purdy et al., "Thiol-ractive lanthanide . . . diffraction data", Acta Crystallographica D58, pp. 1111-1117, 2002.
E. Saridakis et al., "Protein crystallization . . . imprinted polymers", Proceedings of the National Academy of Sciences, vol. 108, pp. 11081-11086, 2011.
N. Silvaggi et al., "Double-Lanthanide-Binding Tags . . . Structure Determination", J. Am. Chem. Soc., vol. 129, pp. 7114-7120, 2007.
X. Su et al., "[Ln(DPA)₃]³⁻ Is a Convenient . . . NMR Studies", J. Am. Chem. Soc., vol. 131, pp. 10352-10353, 2009.
M. Sugahara et al., "Nucleant-mediated protein . . . synthetic zeolites", Acta Crystallographica D Biol. Crystallography, vol. 64, pp. 686-695, 2008.

* cited by examiner

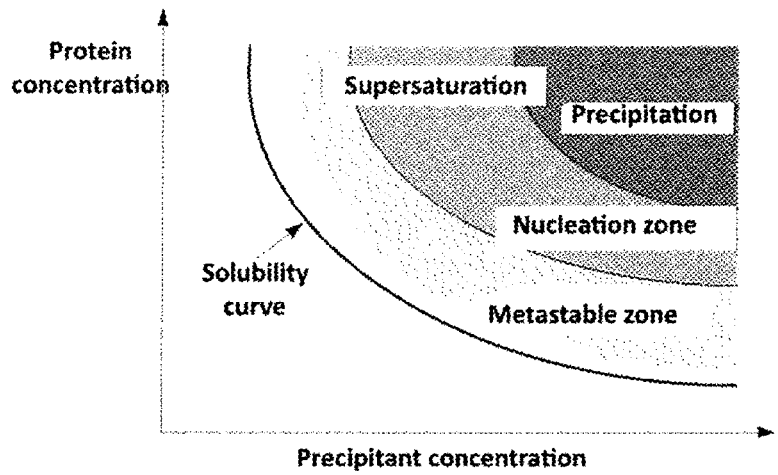
FIGURE 1
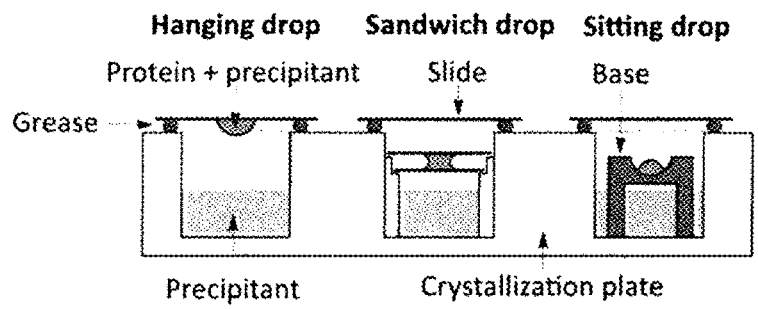
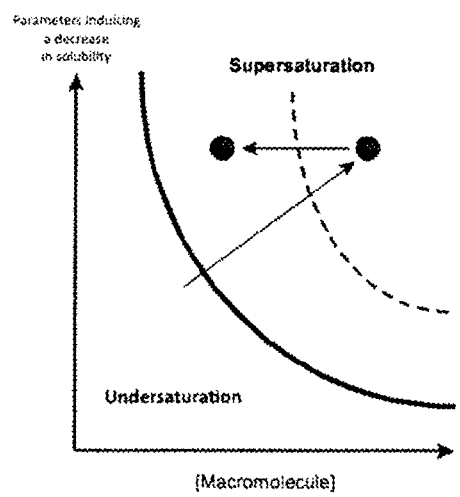
FIGURE 2

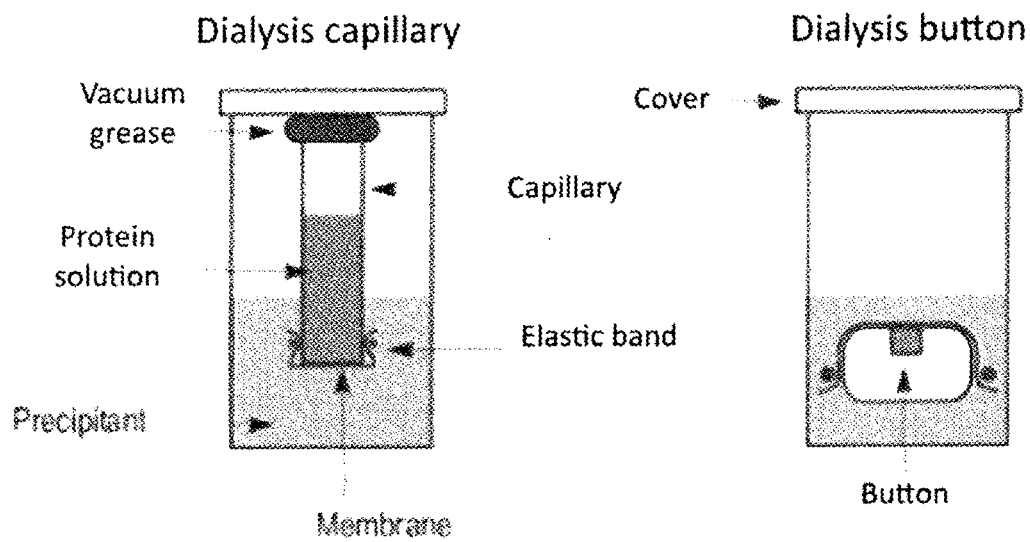
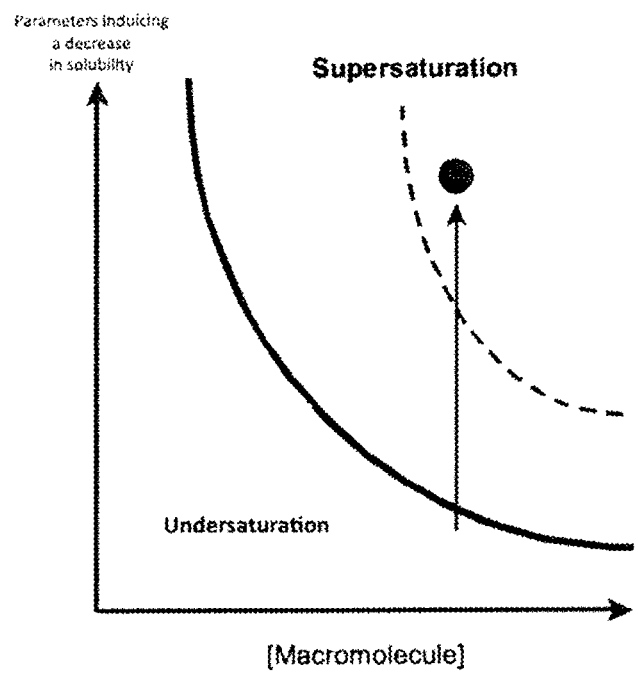
FIGURE 3

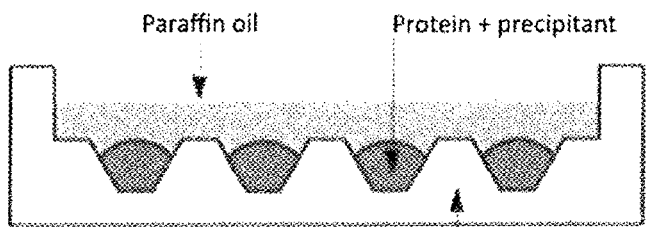
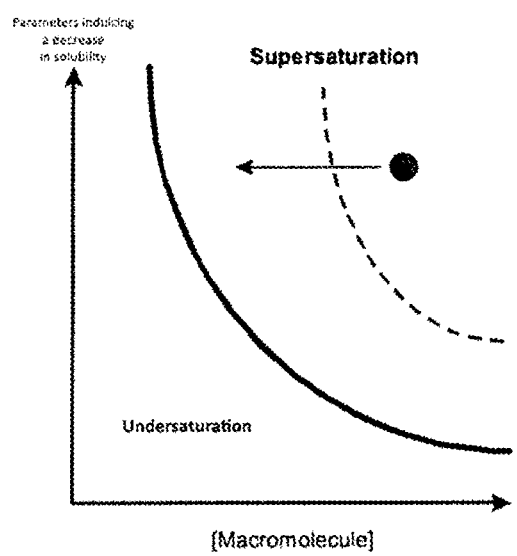
FIGURE 4
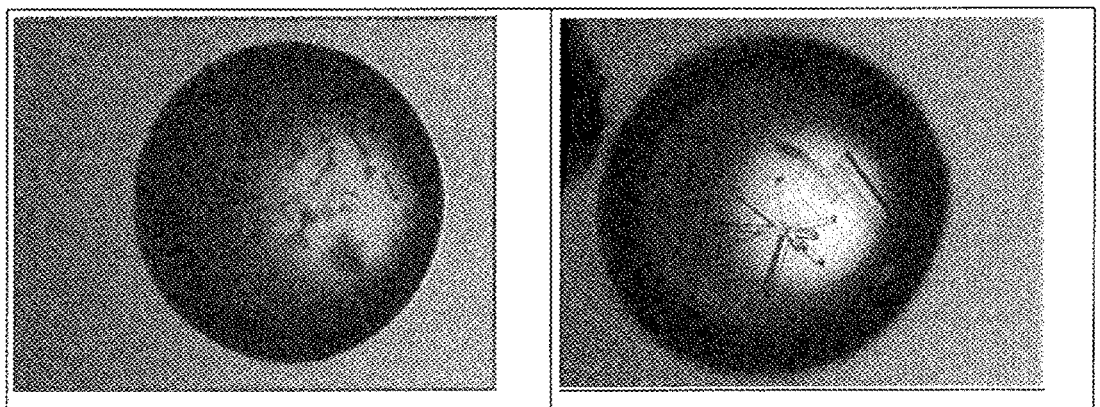
FIGURE 8

| | | |
|---|---|---|
| NatXray system | | |
| | Low luminescent crystals of native lysozyme under UV exposure (280 nm) | Strong luminescent lysozyme crystals (green color) obtained in the presence of 10 mM of complex 10 under UV exposure (280 nm) |
| UV LED source | | |
| | Lysozyme crystals + 10 mM complex 17 in white light. The small crystal (white arrow) has a size of about 45 microns. | Crystals of lysozyme + 10 mM of complex 17 under UV exposure (365 nm) |

FIGURE 9

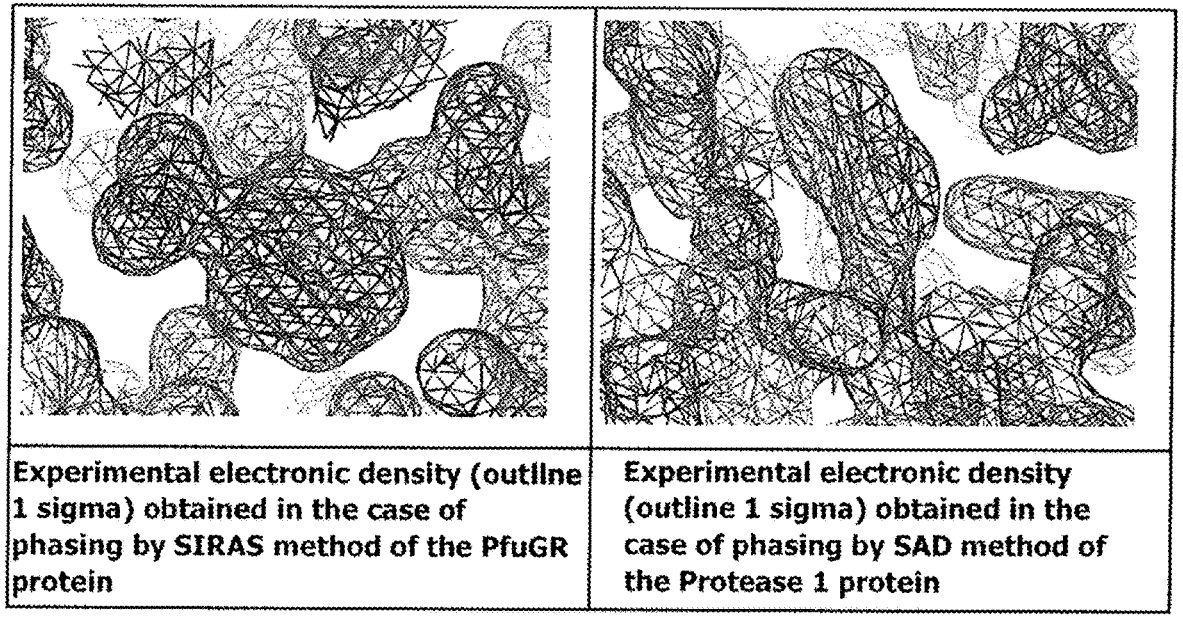
| Experimental electronic density (outline 1 sigma) obtained in the case of phasing by SIRAS method of the PfuGR protein | Experimental electronic density (outline 1 sigma) obtained in the case of phasing by SAD method of the Protease 1 protein |
FIGURE 11
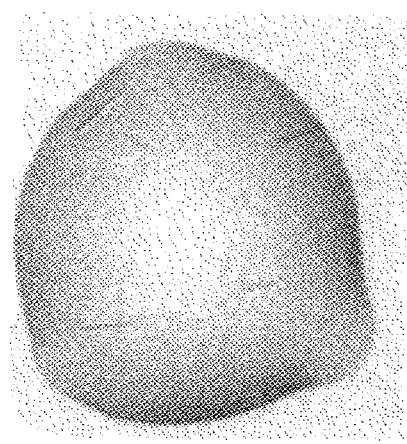
10 mM of complex 10 + ANC80
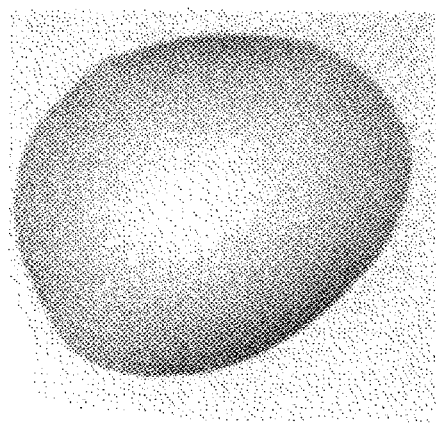
native ANC80
FIGURE 12

LANTHANIDE COMPLEXES FOR CRYSTALLISING BIOLOGICAL MACROMOLECULES AND DETERMINING THE CRYSTALLOGRAPHIC STRUCTURE THEREOF

The present invention relates to the technical fields of crystallization and crystallography. More specifically, the invention concerns new lanthanide complexes which can be used as phasing agents for the determination of the crystal structure of biological macromolecules, but also as an aid for their crystallization. The invention is also intended to be used in these fields and the crystallization and determination of structural data which implement them.

The resounding success of the full determination of the human genome in 2000 paved the way for an even broader area of research: structural genomics, which involves determining the structure of proteins to understand the relationships between their structure and function. Due to the number and variety of proteins available, this is a huge project whose scope in terms of scientific and medical benefits is invaluable. Today, the two tools for this structural resolution are crystallography and nuclear magnetic resonance (NMR). These are two complementary techniques with advantages and limitations: (i) NMR allows protein solution analysis but requires isotopic enrichment; (ii) crystallography allows faster determination of structures but remains dependent on the preparation of good quality crystals. Currently, the research effort is focused on the development of very large instruments to the detriment of the search for new methodologies.

In this area, several successive difficulties have to be overcome. The first difficulty is in the field of biology and concerns the preparation and purification of proteins of interest and only 18% of cloned proteins pass this stage. The second difficulty concerns the crystallization stage, since again only 20% of the purified proteins can be crystallized and only half of these crystals will allow the structure to be determined by X-ray diffraction. On balance, only 1.8% of cloned proteins are structurally characterized and this, at the cost of considerable investment in terms of time and human and financial resources.

A crystal of a protein, or more generally a biological macromolecule, consists of a regular and periodic stacking of the molecules that make up the protein. Stacking is maintained by contacts within the crystal (hydrogen bonds, salt bridges, hydrophobic contacts). Obtaining a crystal from a biological macromolecule is a key step in determining its structure by X-ray crystallography.

It should be noted that the crystallization processes of biological macromolecules are still far from being understood and that current approaches are based on an empirical trial and error approach.

One of the important notions to consider in crystallogenesis is the concept of solubility. In solution, a macromolecule is surrounded by a solvent-based layer that has a repellent and insulating effect and avoids self aggregation and precipitation. Crystallization goes against this effect, since it involves moving away from the solubility conditions of the biological macromolecule by adding a precipitating agent, also called a crystallizing agent. For the purposes of this description, "precipitating agent" and "crystallizing agent" are used interchangeably. crystallizsing/precipitant means a molecule or mixture of molecules which, under certain conditions, help to form a crystal of biological macromolecules.

The general principle of crystallization is based on the diagram presented in FIG. 1, which corresponds to the diagram produced by Mirjam Leunissen and appearing on http://people.ds.cam.ac.uk/ml527/publications/assets/leunissen-literature-research.pdf.

The two main steps that occur in the crystallization process are: nucleation and crystal growth. The crystallizing agent induces a change in solubility and therefore in the position on the diagram as a function of time. There are different crystallization methods using a crystallizing agent. The crystallizing agent induces a change in solubility and therefore in the position on the diagram as a function of time. There are different crystallization methods using a crystallizing agent.

The aim during crystallization is to play on the concentrations of biological macromolecule and crystallizing agent in order to reach the nucleation zone represented on the diagram in FIG. 1. When this zone is reached, nuclei (nucleation points) can form. These nuclei are more or less organized aggregates of about a hundred macromolecules. The formation of these "crystalline" departures reduces the concentration of soluble macromolecule. This is the beginning of crystal growth. Other macromolecules are added to this nuclei and form microcrystals that will grow over time. There are three major classes of crystallizing agents:

salts,
organic solvents (ethanol, dioxane, MPD for methylpentanediol etc.)
polymers (PEG (Poly-Ethylene Glycol) with molecular weighting up to 20000 g/mol, Jeffamine T etc.)
These agents have the effect:
to compete with the biological macromolecule for water, or more generally the solvent in which the macromolecule is initially in solution, and thus decrease the solubility of the macromolecule, inducing its crystallization,
to shield charges on the surface of the macromolecule allowing several macromolecules to get closer together,
to change the dielectric constant of the solvent and therefore the forces between macromolecules
to favor phenomena of excluded volume type (hydrophobic exclusion).

To obtain the crystallization of a protein, or more generally of a biological macromolecule, an automated approach allowing a screening of different commercially available crystallization conditions (for example, Hampton Research crystallization kits). Crystallization experiments are prepared by robots and the crystallization phase is regularly monitored by microscope robots that scan the appearance of the crystals. This high-throughput approach has shifted the search for alternative methodologies to promote crystallization, including finding agents that promote crystallization without denaturing the protein. Some works exist on this subject in the literature, such as the use of natural compounds: mineral solids (Falini G., Fermani S., Conforti G., Ripamonti A. (2002); Acta Crystallogr D Biol Crystallogr. 58, 1649-1652, McPherson, A. & Shlichta, P. (1988), Science, 239, 385-387), substrate of biological origin such as hair, horsehair, rat whiskers or dried algae (D'Arcy A., Mac Sweeney A. & Haber, A. (2003), Acta Crystallogr D Biol Crystallogr. 59, 1343-1346), but also synthetic products (Bijelic A., Molitor C., Mauracher S., G. Al-Oweini, R., Kortz U. & Rompel, A. (2014), Chem Bio Chem. 16, 233-241, Pechkova, E. & Nicolini, C. (2002), J. Cell. Biochem. 85, 243-251, Sugahara, M. Asada, Y. Morikawa, Y. Kageyama, Y. & Kunishima, N. (2008), Acta Crystallogr D Biol Crystallogr. 64, 686-695, Matar-Merheb, R. Rhimi, M. Leydier, A. Huché, F. Galián, C. Desuzinges-Mandon, E. Ficheux, D. Flot, D. Aghajari, N. Kahn, R. et al. (2011), PLoS ONE. 6, e18036).

In all these cases, crystalline growth occurs in contact with these "impurities". The most successful work in this area is that of Naomi E. Chayen's team, which proposes the use of mesoporous materials, capable of inducing nucleation in pores after a concentration/aggregation stage within the pores (WO 02/088435). The same group also describes the use of MIP "molecular imprinted polymers" based on the same principle. These are polymers previously printed by the protein to be crystallized and which therefore contain traces of it. Added to the crystallization drop, a form interaction can occur that favors nucleation (Saridakis, PNAS, 2001, 108,11081). All these crystallization aid agents are solids forming a heterogeneous phase in the crystallization medium, each of which must therefore be added manually to the crystallization drop, which is incompatible with the use of robotic screening platforms, except for MIP.

Moreover, due to the gigantic size of biological macromolecules, such as proteins, the determination of their structure by X-ray diffraction involves solving the problem of crystallographic phases. This implies having a native crystal (pure protein) and/or a derivative crystal containing a heavy atom easily identifiable and allowing to remove the problem of phases, we speak of phasing agent. The most classical method, based on muitiwavelength anomalous diffraction (MAD) is based on the replacement of the sulphur of the amino acids methionines of the protein by a selenium atom. Used since the 1990s, this method has revolutionized macromolecular crystallography, but it involves the synthesis, purification, crystallization and resolution of the structure of analogous selenium proteins. This is a very time-consuming method. Other exogenous phasing agents can be used and are marketed, such as bromine, heavy metals (Pt, Au, Hg). In this context, R. Kahn showed in the early 2000s that lanthanides, which have some of the most intense anomalous effects, can be included as complexes in protein crystals, which allows the structure of the macromolecule to be resolved quickly if lanthanide is fixed (E. Girard, M. Stelter, P. L. Anelli, J. Vicat, R. Kahn, Acta. Cristallogr. D, 2003, D59, 118; E. Girard, P. L. Anelli, J. Vicat, R. Kahn, Acta. Cristallogr. D, 2003, 059, 1877). To date, five lanthanide complexes are marketed as phasant agents by NatX-ray.

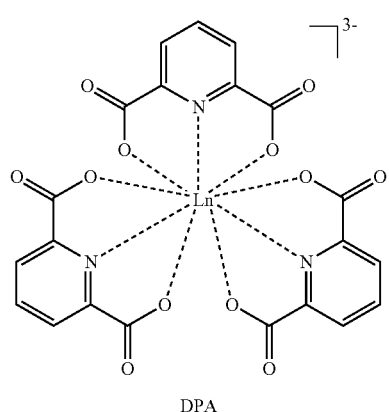

DPA

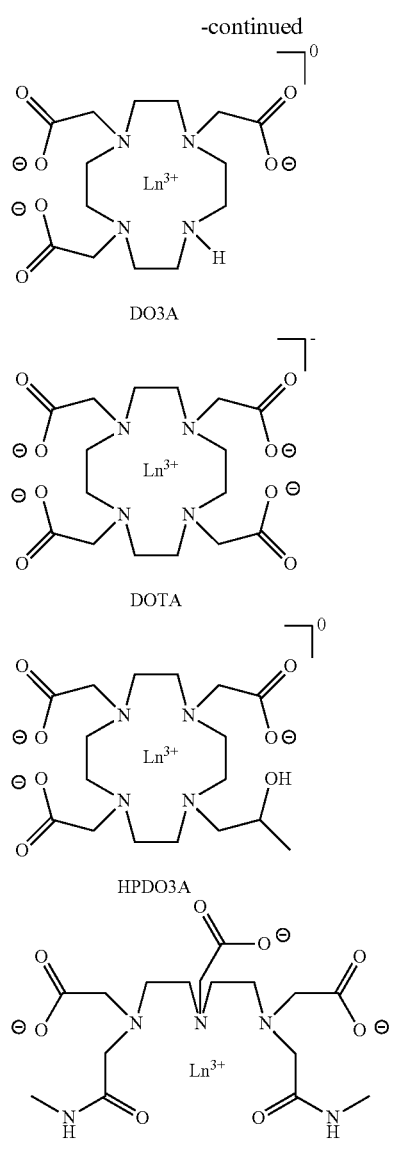

DO3A

DOTA

HPDO3A

DTPA-BMA

Ln = Eu, Yb, (et Gd poour HPDO3A)

It exists in the literature some phasing luminescent agents, such as functional derivatives of $DPA_3$ (FR 2 991 322 et ACIE 2008) or complexes of lanthanide directly grafted to the structure of proteins (X. C. Su, H. B. Liang, K. V. Loscha and G. Otting, J. Am. Chem. Soc., 2009, 131, 10352-10353).

Of all these derivatives, the tri-anionic complexes $[(DPA)_3 Ln]^{3-}$ seemed very promising because specific interactions with cationic amino acids and, in particular, arginine, were highlighted by some of the inventors of this patent application (E. Dumont, G. Pompidor, A. D'Aléo, J. Vicat, L. Toupet, R. Kahn, E. Girard, O. Maury, N. Giraud, Phys Chem Chem Phys 2013, 15, 18235-18242), and confirmed by NMR measurements (X. C. Su, H. B. Liang, K. V. Loscha, G. Otting, J. Am. Chem. Soc., 2009, 131, 10352-10353). Unfortunately, this compound has been shown to be unstable in a large number of commercial crystallization kits; (i) the presence of transition metals (Zn (II), Cu (II), Fe (II)) induces the destructuring of the complex, (ii) the presence of divalent alkaline earth salts (Ba (II), Ca (II), Mg (II)) induces immediate self-crystallization of the complex giving rise to false positives detection (crystals of complexes and not of crystals derived from proteins) (Doctoral thesis of R. Talon supported defended in Grenoble on Jun. 6, 2012).

Other solutions have proposed to introduce lanthanides into protein crystals to obtain a phasant effect. Nagem et al. (Nagem, R. A., Dauter, Z. & Polikarpov I, Acta Crystallogr. D, 2001, D57, 996-1002) proposed the use of lanthanide salts and the rapid soaking method (Dauter Z., Dauter, M. & Rajashankar, K. R. Acta Crystallogr. D, 2000, D56, 232-237). This method, originally developed for the haiogenide salts (NaCl, NaI, NaBr) consists of soaking the crystals in a highly concentrated salt solution (>1 mol L$^{-1}$) for a time of less than one minute. In the case of lanthanide salt, this method led to rapid crystal degradation. Purdy et al (Purdy M. D., Ge P., Chen 1, Selvin P. R., & Wiener, M. C. Acta Crystallogr. D, 2002, D58,1111-1117) proposed to use a covalent bond linking lanthanide complexes (where the ligand provides complete coordination of lanthanide) to the protein. The binding consists of a disulfide bridge formed between free cysteines of the protein and a thiol reactive function carried by the complex. Finally, Silvaggi et al. (Silvaggi, N. R., Martin, L. 1, Schwalbe, H., Imperiali, B., Allen, K. N. 1, Am. Chem. Soc, 2007 129,7114-7120) proposed the use of a "tag" fixing one or two lanthanides (LBT for Lanthanide-Binding Tag). LBT is based on a peptide sequence derived from calcium loops that can be introduced into proteins by conventional molecular biology techniques (Allen, K. N. Imperiali B., Current Opinion in Chemical Biology, 2010, 14, 247-254).

There is therefore a need for new phasing agents that do not require modification of the structure of biological macromolecules, the structure of which is to be determined. In addition, the invention proposes to provide phasing agents which are sufficiently stable in most conditions of crystallization of biological macromolecules and which also make it possible to broaden increase the possibilities of obtaining crystals allowing to obtain structural informations on the biological macromolecules of interest. In this context, the invention concerns cationic complexes consisting of a lanthanide $Ln^{3+}$ and a ligand of formula (I):

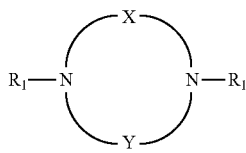
(I)

in which: X and Y, which may be identical or different, each independently represent —CH$_2$—(CH$_2$)$_n$—, —CH$_2$—(CH$_2$)$_n$-A-CH$_2$CH$_2$— or —CH$_2$—CR$_3$R'$_4$—CH$_2$—, X being based on the general formula (I) from left to right and Y being based on the general (I) from right to left, with::
n which is equal to 1, 2 or 3;
A which is —NR$_2$—, —O(CH$_2$)$_2$O— or —O—, with R$_2$ which is a hydrogen atom or a methyl group or —CH$_2$R$_5$, where R$_5$ is a phenyl, pyridinyl or picolinyl;
R$_3$ represents a methyl group; and
R'$_4$ represents —NHR$_4$ with R$_4$ which represents —H, —CH$_3$, —CH$_2$R$_6$; R$_6$ represents a phenyl or pyridinyl group;

R$_1$ represents:

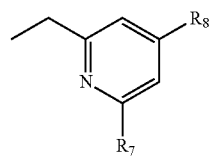

with:
R$_7$ which represents —COO, —CONH$_2$, —CONHR$_9$, —PR$_9$OO$^-$, or a selected group chosen among:

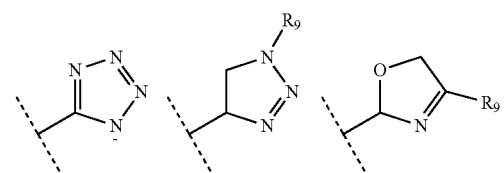

with R$_9$ which represents a hydrogen atom, a methyl, ethyl or phenyl group; and
R$_8$ which represents a hydrogen, fluorine, chlorine, bromine or iodine atom, an —OH or —NH2 group;
with the proviso that at least one of the sequences X and Y is different from —CH$_2$—(CH$_2$)$_n$—,
and their salts with an anion, their solvates and hydrates; with the exception of cationic complexes consisting of a lanthanide ion $Ln^{3+}$ and a ligand having one of the following formulae (I.1) to (I.5) and salts thereof with anion, solvates and hydrates thereof:

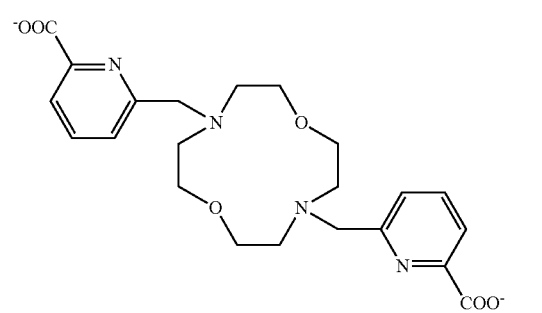
(I.1)

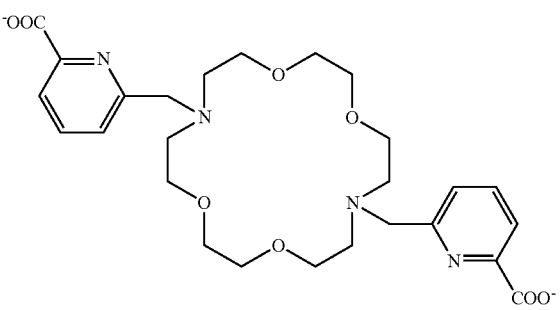
(I.2)

-continued

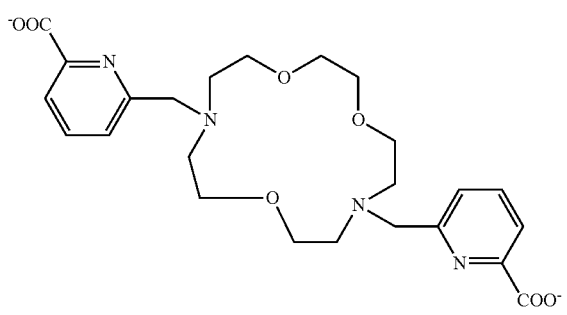

(I.3)

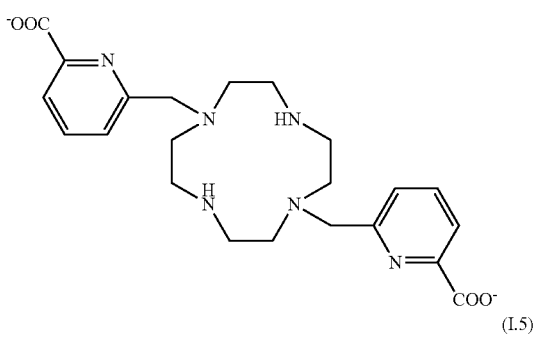

(I.4)

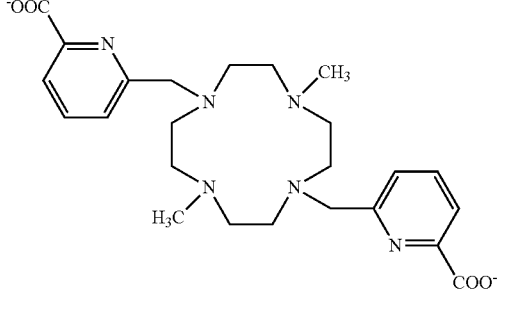

(I.5)

The ligands of formula (I) comprise at least 7 coordination sites for a lanthanide ion $Ln^{3+}$, or more, depending on the structures of X and Y. These coordination sites are located on the two nitrogen atoms represented on formula (I), on the two pyridines of the $R_1$, on the two $R_7$ groups, at least one coordination site is located on X and/or Y.

The complexes according to the invention, as well as the lanthanide complexes formed with ligands of the formulae (I.1) to (I.5), are cationic and have a positive charge greater than or equal to 1. They comprise a macrocyclic ligand incorporating several aromatic groups forming an open coordination sphere for the lanthanide ion. These aromatic groups, when the $Ln^{3+}$ ion is $Eu^{3+}$ or $Tb^{3+}$, also act as antennas to sensitize the luminescence of lanthanide in the visible.

Furthermore, the complexes according to the invention, have the advantage of being water soluble and stable in most commercial crystallization media. In the context of the invention, these complexes have been shown to be of interest not only as a phasing agent when obtaining structural data, but also as an aid to crystallization. In particular, said complex is used as a nucleating agent and/or as a crystallizing agent in the crystallization of a biological macromolecule. Such applications had never been described or considered for lanthanide complexes formed with ligands of the formulae (I.1) to (I.5) already described in the literature (M. Mato-Iglesias et al., Inorg. Chem. 2008, 47, 7840-7851; Z. Palinkas et al., Inorg. Chem. 2009, 48, 8878-8889; A. Roca-Sabio et al., Dalton Trans, 2011, 40, 384-392 and M. Regueiro-Figueroa et al., Inorg. Chem. 2015, 54, 4940-4952 for ligand complexes (I.1) to (I.3) and A. Rodrigues-Rodrigues et al., Inorg. Chem. 2012, 51, 2509-2521, for ligand complexes (I.4) and (I.5)). Indeed, these complexes were prepared for fundamental studies of coordination chemistry of lanthanides (study of the stability of complexes formed with different lanthanides) and in the case of Gd, only applications as an MRI contrast agent were considered.

In an advantageous way, the complexes according to the invention, as well as their salts with anion, solvates and hydrates, are formed with a ligand corresponding to one of the following formulae:

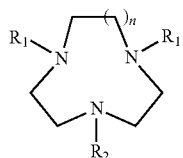

(IA)

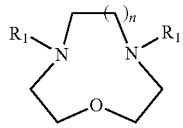

(IB)

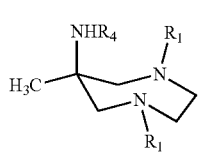

(IC)

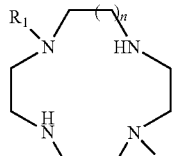

(ID)

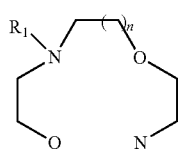

(IE)

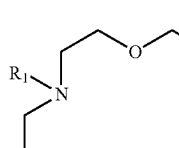

(IF)

with $R_1$, $R_2$, n and $R_4$ as defined for formula (I).

As an example of salts, complexes according to the invention or complexes formed with one of the ligands (I.1) to (I.5) which are applied in the context of the invention, one can cite salts of a cationic complex with an anion (or several anions, depending on the charge of the complex) chosen from: $Cl^-$, $Br^-$, $I^-$, $OH^-$, $NO_3^-$, triflate, $PF_6^-$, $SbF_6^-$, $B(Ph)_4^-$, $BF_4^-$, sulphates, sulphonates, carbonates, phosphates, phosphonates and carboxylates. Sulphates and sulphonates may correspond to $SO_4^{2-}$, $HSO_3^-$ or $R'SO_3^-$, carbonates to $CO_3^{2-}$, $HCO_2^-$ or $R'CO_2^-$, phosphates and phosphonates to $R'OPO_3^{2-}$ and $R'PO_3^{2-}$ and carboxylates to $R'CO_2^-$, with R' which may be, in particular, an alkyl or aryl group, in particular an alkyl group containing 1 to 4 carbon atoms or a phenyl group. In the form of salts, the complexes, depending on the invention, may also be in the form of hydrate or solvates, i.e. with at least one water or solvent molecule in the lanthanide coordination sphere. Preferably, the complexes according to the invention, as well as their salts with anion, solvates and hydrates, are formed with a ligand corresponding to the formula (IA):

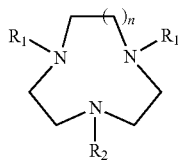
(IA)

wherein n=1 and $R_2$=H, and $R_1$ is as defined for the compounds of formula (I).

In an advantageous way, in the ligands of formula (I), (IA) to (IF), $R_1$ represents:

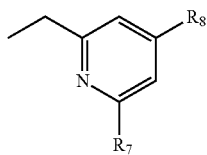

with:
$R_7$ which represents $-COO^-$ or $-PR_9OO^-$ with $R_9$ qui representing methyl or ethyl; or $R_7$ representing a group:

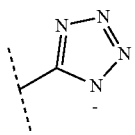

$R_8$ which represents a hydrogen, fluorine, chlorine, bromine or iodine atom.

In the context of the invention, when a substituent represents a picolinyl group, it represents:

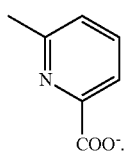

Preferably, the complexes according to the invention are chosen among the complexes of formula:

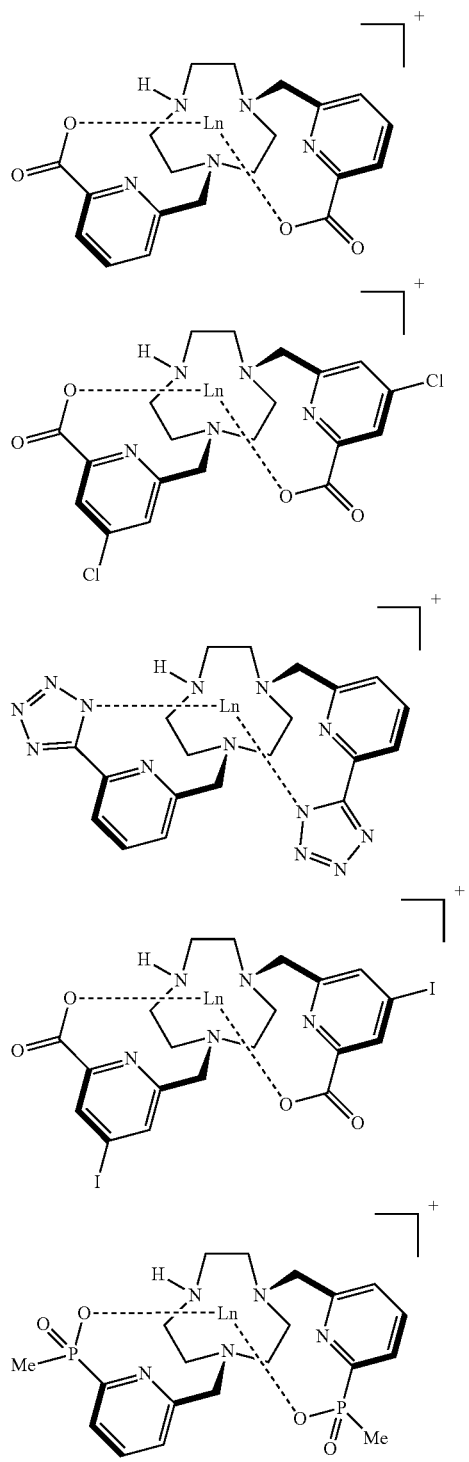

as well as their salts with anion, in particular their hydrochloride salt, solvates and hydrates. In an advantageous way, the complexes according to the invention or the complexes formed with one of the ligands (I.1) to (I.5) which find application in the context of the invention, as well as their salts with an anion, in particular their salt. hydrochloride, their solvates and hydrates, are formed with a lanthanide ion $Ln^{3+}$, Ln being Sm, Eu, Gd, Tb, Dy, Ho, Er, Tm, Yb or Lu, with Eu, Tb, Yb and Lu which are preferred.

The invention is also intended to use a complex depending on the invention, or a cationic complex consisting of a lanthanide ion $Ln^{3+}$ and a ligand of the formulae (I.1) to (I.5) as previously defined, or a salt thereof with an anion, solvates or hydrates, as an aid to the crystallization of a biological macromolecule. In particular, said complex is used as a nucleating agent and/or as a crystallizing agent in the is crystallization of a biological macromolecule. All lanthanide complexes according to the invention or formed with a ligand of formula (I.1) to (I.5), are of interest for their nucleating or crystallizing effect. However, only terbium or europium complexes will exhibit luminescence properties in the visible. Also, if in the complex, Ln=Eu or Tb, the complex can also be used as a luminescent agent for the detection of crystals. The invention is also intended to use a complex according to the invention, or a cationic complex consisting of a lanthanide ion $Ln^{3+}$ and a ligand of formula (I.1) to (I.5) as previously defined, or a salt thereof with an anion, solvates or hydrates, as an aid in obtaining structural data of a biological macromolecule. In particular, said complex is used as a phasing agent in the structural determination by X-ray diffraction. Again, if in the complex, Ln=Eu or Tb, the complex can also be used as an aid for positioning the crystal in an X-ray beam.

In particular, in the context of the invention, "biological macromolecule" means in particular peptides (sequence of less than 100 amino acids), proteins (sequence of at least 100 amino acids) and nucleic acids, in particular DNA or RNA. Such biological macromolecules shall in particular have an average molecular weight of more than 1 kDa.

The invention also has as its object the crystals of a biological macromolecule comprising a complex according to the invention or a cationic complex formed of a lanthanide ion $Ln^{3+}$ and a ligand of formula (I.1) to (I.5) as previously defined, or a salt thereof with an anion, solvate or hydrate, called derivative crystals.

The invention also has as its object a process for crystallizing a biological macromolecule, preferably selected from peptides, proteins and nucleic acids, in particular DNA or RNA, comprising the following steps:
Having a solution comprising said biological macromolecule and a complex according to the invention, or a cationic complex consisting of a lanthanide ion $Ln^{3+}$ and a ligand of formula (I.1) to (I.5) as previously defined, or a salt thereof with an anion, solvate or hydrate,
obtaining crystals of the macromolecule from said solution.

The solution used may also include a precipitating agent, other than the complex, chosen in particular from among those used in commercial crystallizsation kits, in particular from those listed in the tables presented in Annexes 2A or 2B, such as, for example, salts such as ammonium salts, sulphates (especially ammonium sulphate), acetates, phosphates, citrates (especially sodium citrate), formiates, tartrates such as sodium or potassium tartrate, double tartrate, sodium and potassium, chlorides, iodides and fluorides, for example NaCl; polymers such as polyethylene glycols and Jeffamine T; ethanol, dioxane, methylpentanediol, glycerol, isopropanol, 2-methyl-2,4-pentanediol.

In the solution, the complex is advantageously present at a concentration of 1 to 100 mM, preferably at a concentration of 1 to 25 mM, and even more favorably at a concentration of 10 mM±10%.

In particular, crystals are obtained by vapor diffusion crystallization, by dialysis, in batch or in a process of crystallization in the cubic phase of lipids.

The crystallization process, depending on the invention, can be integrated into a screening process or an optimization of the crystallization conditions of a biological macromolecule. The crystallization process according to the invention can be automated.

The invention shall also have as its subject matter a method of analyzing or determining the structure of a biological macromolecule comprising the following steps:
(a) having at its disposal a derivative crystal from the biological macromolecule as defined in the invention,
(b) analyzing the crystalline structure of the biological macromolecule from said derivative crystal.

The derivative crystal may be obtained by a crystallization process as described in the invention or by soaking a crystal from the biological macromolecule in a solution of a complex according to the invention or a cationic complex consisting of a lanthanide ion $Ln^{3+}$ and a ligand of formula (I.1) to (I.5) as previously defined, as well as their salts with an anion, their solvates or hydrates. The derivative crystal may also be obtained by soaking a derivative crystal from the biological macromolecule obtained by a crystallization process as described in the invention, in a solution of a complex according to the invention or a cationic complex consisting of a lanthanide ion $Ln^{3+}$ and a ligand of formula (I.1) to (I.5) as previously defined, or of a salt thereof with an anion, their solvates or hydrates.

In particular, the analysis of the crystalline structure of the biological macromolecule from said derived crystal corresponds to the determination of the structure of the biological macromolecule and is carried out by X-ray diffraction (RX). It is also possible that it corresponds to the obtaining of structural data by a high resolution method, such as X-ray diffraction (RX) or by a low resolution method by SAXS methods (Small-Angle X-ray Scattering) or MASC (Multi-wavelength-Anomalous Solvent Contrast).

The following detailed description provides a better understanding of the invention.

The cationic complexes formed from a lanthanide ion $Ln^{3+}$ and a ligand of formula (I), corresponding to complexes according to the invention or complexes formed with a ligand of formula (IA) to (IF) are cationic complexes, and in particular mono-cationic complexes. They are therefore capable of producing crystals derived from a biological macromolecule. Such derived crystals can be obtained by dipping or co-crystallization, as detailed below. The anomalous effect due to the presence of lanthanides in the derived crystals obtained leads to a phasing effect and facilitates the determination of the structure of the biological macromolecule concerned, in particular by X-ray diffraction. Complexes depending on the invention can therefore be used as an aid in determining or analyzing the crystalline structure of a biological macromolecule.

The cationic complexes formed from a lanthanide ion $Ln^{3+}$ and a ligand of formula (I), corresponding to complexes according to the invention or complexes formed with a ligand of formula (IA) to (IF), as well as their salts, solvates and hydrates may also be used as an aid in the crystallization of biological macromolecules. Indeed, depending on their structure and the crystallization conditions used, the complexes according to the invention have at least one of the following properties:
nucleating effect: the presence of said lanthanide complex during crystallization causes the growth of crystals under conditions (buffer and/or additives and/or temperature and/or concentration and/or duration . . . ) which do not allow the formation of crystals in the absence of the complex according to the invention.

Crystallizing effect: the presence of the said lanthanide complex during tests of a series of crystallization conditions (number of crystals and/or crystal size and/or improved diffraction of the obtained crystals . . . ) allows to improve the crystallization obtained, compared to a series of conditions differing by the absence of complex. In the absence of complexes, crystals appear but are of poorer quality.

In particular, the lanthanide complexes formed with ligands of formula (I) consisting of a lanthanide ion $Ln^{3+}$ and a ligand of formula (I), corresponding to the complexes according to the invention or complexes formed with a ligand of formula (IA) to (IF), as well as their salts, solvates and hydrates, either increase the number of conditions under which the crystal formation of a macromolecule is possible, or to work under conditions lower in biological macromolecule and/or other precipitating agent conventionally used, either to improve the quality or the number of crystals thus favoring the obtaining of subsequent structural data, or to obtain several of these advantages.

The Europium and Terbium complexes also have the advantage of being luminescent under UV irradiation. Thus, their use allows an easy identification of the derived crystals during crystallization tests. This property can be used as a rapid detection method for crystallization platforms equipped with an automatic UV imaging device. In addition, this property can be used as an aid for centering in an X-ray beam during diffraction characterization, in particular.

Complexes depending on the invention may be prepared according to techniques adapted by the skilled person, techniques described in the examples or in application WO 2014/162105. The synthesis of complexes according to the invention is usually carried out in water. The complexes thus formed will therefore be more in the form of hydrate, but this complex can then be put in a different solvent, such as alcohol or DMSO, and give rise to a solvate or be dehydrated. In hydrated form, a complex according to the invention will contain up to 3 molecules of water per complex. On average, the number of water molecules per complex may, however, be different from an integer, e.g. equal to 0.5. For the applications envisaged in the context of the invention, lanthanide complexes depending on the invention may be used in hydrated form, or dehydrated, solvated or not, in powder form or in solution.

The quality and purity of a crystallizing agent are essential for the smooth implementation of the macromolecule crystallization when used as a crystallizing agent. Finally, lanthanide complexes according to the invention will be subjected to an appropriate purification step, in particular by steric exclusion chromatography.

The cationic complexes consisting of a lanthanide ion $Ln^{3+}$ and a ligand of formula (I), corresponding to the complexes according to the invention or complexes formed with a ligand of formula (IA) to (IF), as well as their salts, solvates and hydrates, may be used as a crystallizing agent in any technique suitable for the crystallization of biological macromolecules.

For a detailed description of such techniques, reference can be made to the following reference works: <<Protein Crystallization, Second Edition (IUL Biotechnology Series)>> edited by Therese Bergfors or <<Crystallization of Nucleic Acids and Proteins: A Practical Approach>> edited by Arnaud Ducruix and Richard Giegé.

In particular, cationic complexes formed from a lanthanide ion $Ln^{3+}$ and a ligand of formula (I), corresponding to complexes according to the invention or complexes formed with a ligand of formula (IA) to (IF), as well as their salts, solvates and hydrates, may be used as a crystallizing agent in a process for the crystallization of biological macromolecules by vapor diffusion, dialysis, batch or in a method of crystallization in cubic phase of lipids.

These different techniques will each be described briefly, the crystallizing agent being a lanthanide complex or a mixture of crystallizing agents containing at least one lanthanide complex with a ligand of formula (I) in the form of salts, solvates or hydrates:

Vapor diffusion crystallization is the most commonly used crystallization method at present. This is the method generally used in automated crystallization platforms. There are three different schematic approaches in FIG. 2: the techniques of sitting drop, hanging drop and sandwich drop. These three techniques are shown schematically in FIG. 2.

In these three approaches, a solution of the crystallizing agent is placed in a well (light grey solution). The solution containing the biological macromolecule of interest is mixed with the crystallizing agent and deposited as a drop (either suspended, sitting or as a sandwich). The crystallization well is hermetically sealed with a glass plate or plastic film. At the start of crystallization, the concentration of the crystallizing agent in the drop is twice as low as in the well. Once the system is closed, a diffusion kinetics of the solvent from the drop (usually water) towards the well is set up. The volume of the drop will therefore decrease (loss of solvent i.e. of water) and the concentrations of biological macromolecule and crystallizing agent will thus increase, allowing, in favorable cases, to reach the nucleation phase. In this method, the concentration of crystallizing agent is extremely important. Indeed, an excess of crystallizing agent could lead to a diffusion kinetics of the solvent too fast and thus lead to the precipitation of the biological macromolecule. On the contrary, a too low concentration will not reach the nucleation zone. The concentration of the appropriate crystallizing agent will therefore be determined by routine tests carried out by the skilled worker. From the nucleation, crystalline growth will then decrease the concentration of soluble macromolecule until it reaches a stationary state.

Dialysis is another crystallization method, but it is less used than steam diffusion. This technique is shown schematically in FIG. 3.

The general principle is to slowly increase the concentration of the crystallizing agent. For this purpose, a solution containing the relevant biological macromolecule is placed in a dialysis container, e.g. capillary type or dialysis button closed by a semi-permeable membrane allowing the molecules of crystallizing agent (but not the macromolecule) to pass through. This container is then placed in a solution of crystallizing agent. An equilibrium between the solution containing the biological macromolecule of interest (which does not contain a crystallizing agent) and the external solution containing the crystallizing agent will be established. Thus, the concentration of the crystallizing agent in the dialysis container will increase and modify the solubility of the macromolecule. This technique has the advantage of being more precise than vapor diffusion with respect to maintaining pH and volume. However, the handling of crystals remains much more delicate.

Batch crystallization is the latest technique used to crystallize biological macromolecules. This technique, like dialysis, requires a large volume of solution.

The principle of this technique, shown schematically in FIG. 4, is simple: the highly concentrated macromolecule is mixed with the crystallizing agent. The oversaturated macromolecule solution will, over time, induce nuclei formation which will induce a decrease in the concentration of the macromolecule in solution, towards the formation of crystals.

The techniques of steam diffusion crystallization, crystallization by means of dialysis or batch crystallization work on all types of proteins, whether water-soluble or membranous, then soluble in detergent, as well as on other biological macromolecules (DNA, RNA, protein complexes, protein-DNA or RNA complexes, etc.).

For the crystallization of membrane proteins, it is also possible to use a lanthanide complex as a crystallizing agent in a technique of cubic phase lipid crystallization. The cubic phase crystallization of lipids of membrane proteins is described in the following publications: Landau et al. Lipidic cubic phase: A novel concept for the crystallization of membrane proteins, PNAS Vol. 93 no. 25 14532-14535 (1996), Caffrey et al. Crystallizing membrane proteins using lipidic mesophases. Nat Protoc 4 (5) 706-31 (2009), Cherezov V., Lipidic cubic phase technologies for membrane protein structural studies. Curr. Opin Struct Biol Vol 21 559-566 (2011).

Lanthanide complexes formed from a lanthanide ion $Ln^{3+}$ and a ligand of formula (I), corresponding to complexes according to the invention or complexes formed with a ligand of formula (IA) to (IF), as well as their salts, solvates and hydrates are compatible with all crystallization methods which have just been detailed.

In particular, a solution containing a concentration of 1 to 100 mM, preferably 1 to 25 mM of a lanthanide complex formed from a lanthanide ion $Ln^{3+}$ and a ligand of formula (I), corresponding to complexes according to the invention or complexes formed with a ligand of formula (IA) to (IF), in the form of a salt with an anion, optionally in the form of a solvate or hydrate and even more preferably 10 mM±10% will be used.

In crystallizations, in particular, in the vapor phase or batch, a solution of the biological macromolecule to be crystallized and a lanthanide complex consisting of a lanthanide ion $Ln^{3+}$ and a ligand of formula (I), corresponding to the complexes according to the invention or complexes formed with a ligand of formula (IA) to (IF), in the form of a salt with an anion, optionally in the form of a solvate or hydrate (which, for simplification, will be referred to in the remainder of the description as a lanthanide complex), shall be prepared, preferably with a concentration of 1 to 100 mM, preferably 1 to 25 mM, and even more preferably at 10 mM±10%, as a lanthanide complex. The lanthanide complex formed from a lanthanide ion $Ln^{3+}$ and a ligand of formula (I), corresponding to the complexes according to the invention or complexes formed with a ligand of formula (IA) to (IF), in the form of a salt with an anion, optionally in the form of a solvate or hydrate, can be directly solubilized by the solution containing the biological macromolecular to achieve a final complex concentration of 1 to 100 mM, preferably 1 to 25 mM, and preferably 10 mM±10% which corresponds to the concentration at which the nucleating effect is predominant. The lanthanide complex can also be introduced from a solution at a preferential concentration of 10 to 30 mM during the production of a crystallization drop: a volume of the macromolecular solution, an identical volume of the lanthanide complex solution and an identical volume of the well solution used for crystallization are then added successively.

In these crystallization techniques, the lanthanide complex and the biological macromolecule to be crystallized will generally be solved in water or in a buffered aqueous solution (see examples in the description of the crystallization kits in Annexes 2A and 2B), e.g. in an acetate, cacodylate, citrate, Bis tris propane, TRIS, HEPES, phosphate buffer solution. Solutions containing a biological macromolecule are usually buffered. If a solution of the lanthanide complex is formed, it will not necessarily be buffered. The solution containing the complex, the solution containing the biological macromolecule and/or the solution containing the biological macromolecule and the complex, depending on the crystallization technique used, will preferably have a pH in the range of 3 to 9.

Additives such as additives already known to act as precipitating/crystallizing agents or additives which initially facilitate the dissolution of the biological macromolecule to be crystallized may be added. Examples of these are those listed in the tables in Annex 2A or 2B, such as salts such as ammonium salts, sulphates (especially ammonium sulphate), acetates, phosphates, citrates (especially sodium citrate), formiates, tartrates such as sodium or potassium tartrate, double sodium and potassium tartrate, chlorides, iodine, and fluorides, e.g. Nacl; polymers such as polyethylene glycols and Jeffamine T; ethanol, dioxane, methylpentanediol, glycerol, isopropanol, 2-methyl-2,4-pentanediol. In particular, lanthanide complex can be used in any crystallization solution already on the market.

The concentration of macromolecule in the solution will theoretically be close to its solubility limit in the said solution, but may be more diluted, depending on the solution used.

Lanthanide complexes consisting of a lanthanide ion $Ln^{3+}$ and a ligand of formula (I), corresponding to the complexes according to the invention or complexes formed with a ligand of formula (IA) to (IF), in the form of a salt with an anion, optionally in the form of a solvate or hydrate, may also be used to obtain derivative crystals from biological macromolecules, i.e. crystals containing said lanthanide complex. In particular, said lanthanide complex will be fixed on a specific position of the biological macromolecule to be studied, allowing the determination of the structure of said studied biological macromolecule.

The determination of the phases can be carried out with derived crystals obtained in a solution containing 1 to 100 mM of complex, preferably 10 to 100 mM, and in an even more preferable way from 100 mM±10% to the said lanthanide complex. However, in order to improve the quality of phasing, a soaking in a solution of a lanthanide complex, in particular, with a high concentration of complex, can also be carried out. This allows to increase the occupancy rate of the sites occupied by the complex.

Co-crystallization therefore involves adding the lanthanide complex during the crystallization process. Thus, during crystallization, the lanthanide complex can be inserted into specific crystalline sites leading to the production of derivative crystals.

In addition, to obtain a derivative crystal or increase the occupancy by a lanthanide complex of sites in the derivative crystal, a soaking of a biological macromolecule crystal in a lanthanide complex solution can be performed. It is possible to carry out a rapid soaking or long time soaking.

Rapid soaking consists of taking a crystal from a biological macromolecule of interest and soaking it briefly (notably from 45 seconds to 2 minutes) in a solution of the lanthanide complex. The solution in which the crystal is hardened has a high concentration of lanthanide complex, typically 50 to 500 mM, preferably 100 mM±10%.

In particular, a rapid soaking during the freezing phase of one or more crystals can be achieved. A rapid soaking during a freezing phase typically takes place in three steps: crystals are taken from their original drop and soaked in a soaking drop, corresponding to a solution equivalent to the original solution used for the formation of the said crystal(s) to which is added a concentration of 50 to 500 mM, preferably 100 mM±10% of lanthanide complex, and a cryoprotectant agent. After 45 seconds to 2 minutes, the crystal is soaked in a cryoprotective solution without lanthanide complexes to remove its excess. Finally, the crystal is immersed in liquid nitrogen and stored at low temperature, for example at 100K.

This soaking method is very efficient and allows to increase the occupancy rates and improve the quality of the phasing. For example, in the case of PhP1 protein, a 45-second soaking in a 100 mM complex solution increased the occupancy rate of the complex by 3. Rapid soaking prevents crystal from deteriorating and preserves its diffraction properties.

Long time soaking consists of taking a crystal from a biological macromolecule of interest and soaking it for a prolonged period of time (notably from 10 minutes to 24 hours) in a solution of the lanthanide complex. Advantageously, the solution in which the crystal is soaked has a high concentration of lanthanide complex, typically a concentration of 50 to 500 mM, preferably 100 mM±10%.

With the exception of duration, long time soaking can take place according to the same protocol as described for rapid soaking, especially during a freezing phase. However, the soaking drop is placed in equilibrium with a well containing the original solution used for the formation of the said crystal(s) in order to avoid dehydration of the drop.

Regardless of the type of soaking, it is possible to soak both crystals obtained by co-crystallization in the presence of a lanthanide complex and crystals obtained in the absence of such a complex (named native crystals in the context of this patent application). Soaking does not lead to any destruction or modification of the biological macromolecule. Lanthanide complexes allow to form derivative crystals from a biological macromolecule to obtain structural data for said biological macromolecule. In particular, structural data will be obtained from a derivative crystal from a biological macromolecule containing a lanthanide complex that acts as a phasing agent. These structural data can be obtained using a high-resolution method, such as the diffraction of X-rays (RX) or by a low resolution method, such as SAXS and MASC. Lanthanide complexes may be used as a phasing agent in X-ray diffraction (crystallization and structural analysis) or X-ray scattering, or as a contrast agent in SAXS or MASC, in electronic microscopy.

The use of lanthanide complexes consisting of a lanthanide ion $Ln^{3+}$ and a ligand of formula (I) corresponding to the complexes according to the invention or complexes formed with a ligand of formula (IA) to (IF), in the form of a salt with an anion, optionally in the form of a solvate or hydrate, in particular as a phasing agent, has the advantage of not requiring a modification of the biological macromolecule by genetic engineering, as in the case of obtaining selenium proteins. There is no covalent binding between the lanthanide complex and the biological macromolecule of interest.

The following examples, with reference to the attached figures, illustrate the invention but are not specific.

FIG. 1 shows a phase diagram illustrating the crystallization process (extract from http://people.ds.cam.ac.uk/ml527/publications/assets/leunissen-literature-research.pdf)

FIG. 2 shows three different approaches: the techniques of sitting drop, hanging drop and sandwich drop.

FIG. 3 shows the dialysis technique: another crystallization method, which is still less used than vapor diffusion.

FIG. 4 schematically shows a batch crystallization technique used to crystallize biological macromolecules.

Figure 5:
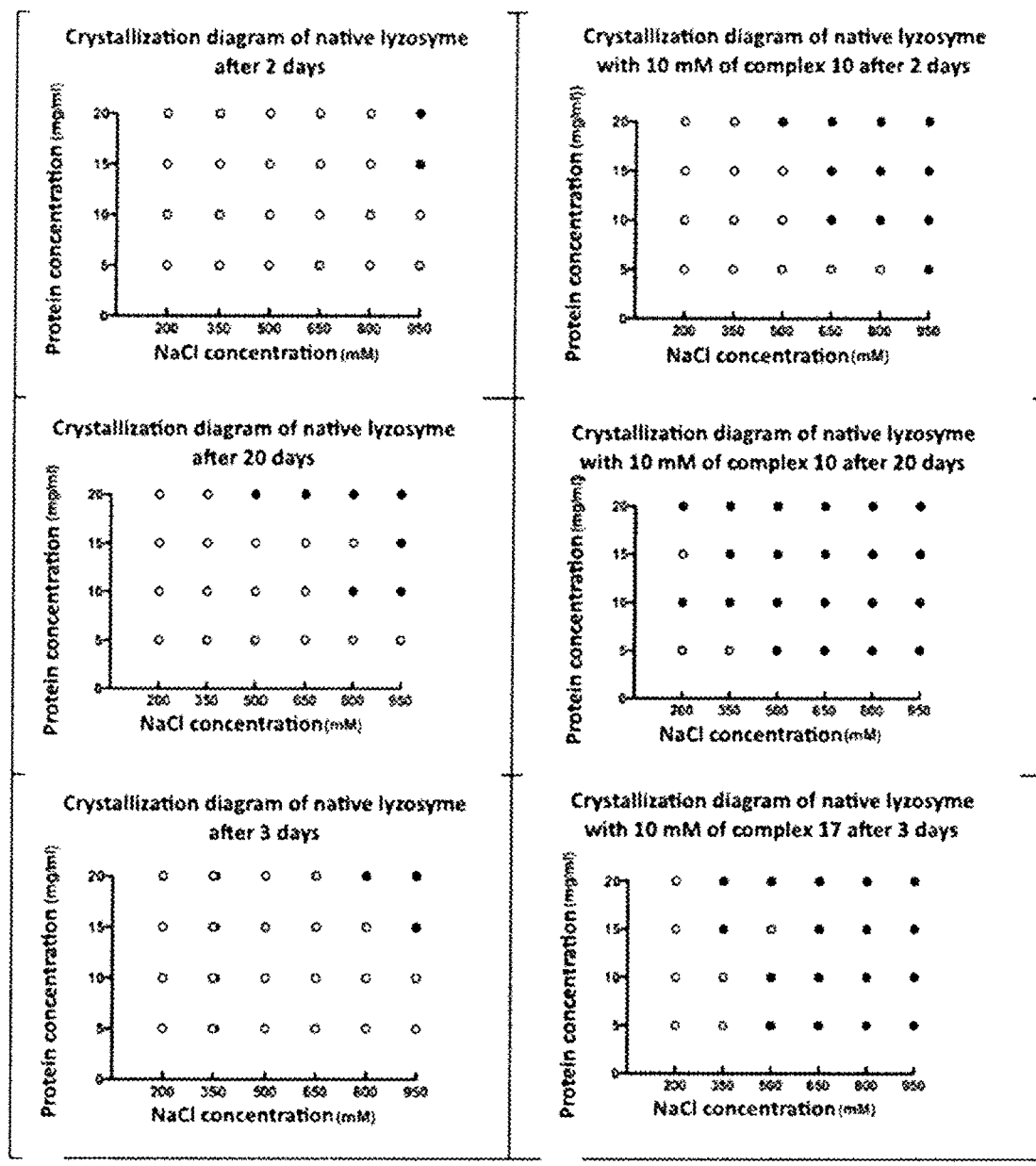

FIG. 5 shows phase diagrams of the lysozyme protein in absence (right) and in the presence of complex 10 or 17 determined at different crystallization times: the conditions, having produced crystals, are illustrated by black dots, the white dots being clear drops.

Figure 6:
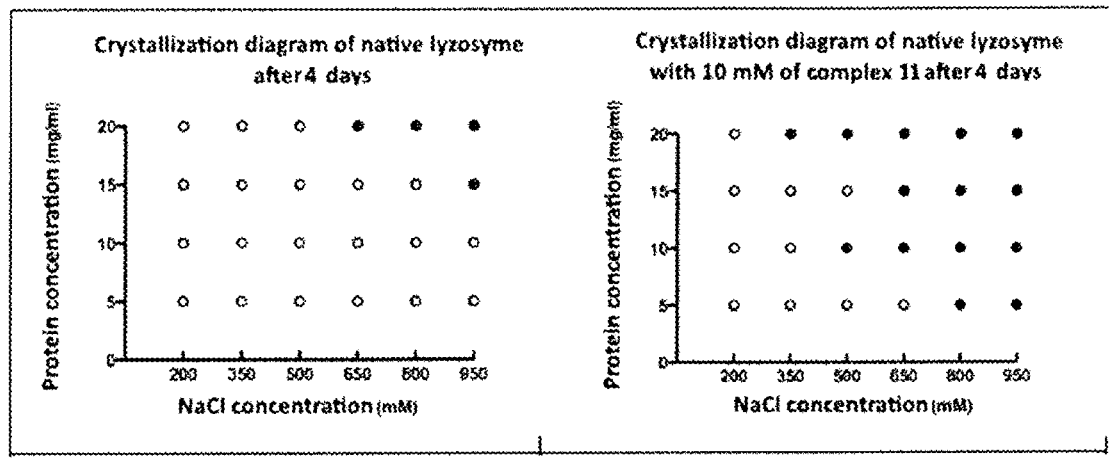

FIG. 6 shows phase diagrams of chicken breast white lysozyme in the absence and presence of complex 11 lysozyme determined after 4 days of crystallization. Crystal conditions are illustrated by black dots, white dots are clear drops and precipitate triangles.

Figure 7:
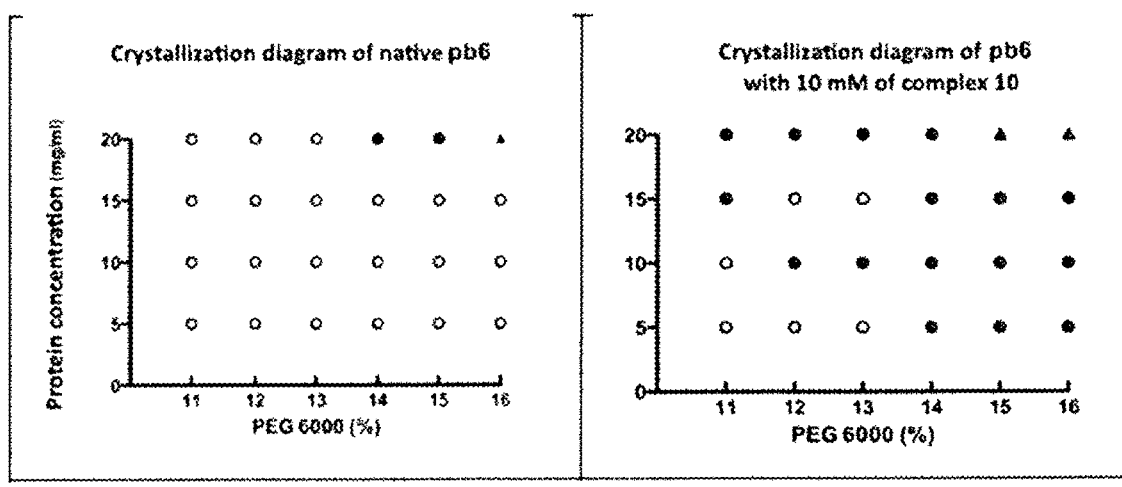

FIG. 7 shows phase diagrams of the PB6 protein in the absence and presence of 10 mM of complex 10 determined after one day of crystallization. Crystal conditions are illustrated by black dots, white dots are clear drops and precipitate triangles.

FIG. 8 shows pb6 crystals (pb6-1 condition) in the presence of 10 mM complex 10 on the right (13% PEG—10 mg/ml) and without complex 10 on the left (15% PEG—20 mg/ml).

FIG. 9 shows the luminescence induced in the crystals by lanthanide complexes.

Figure 10:
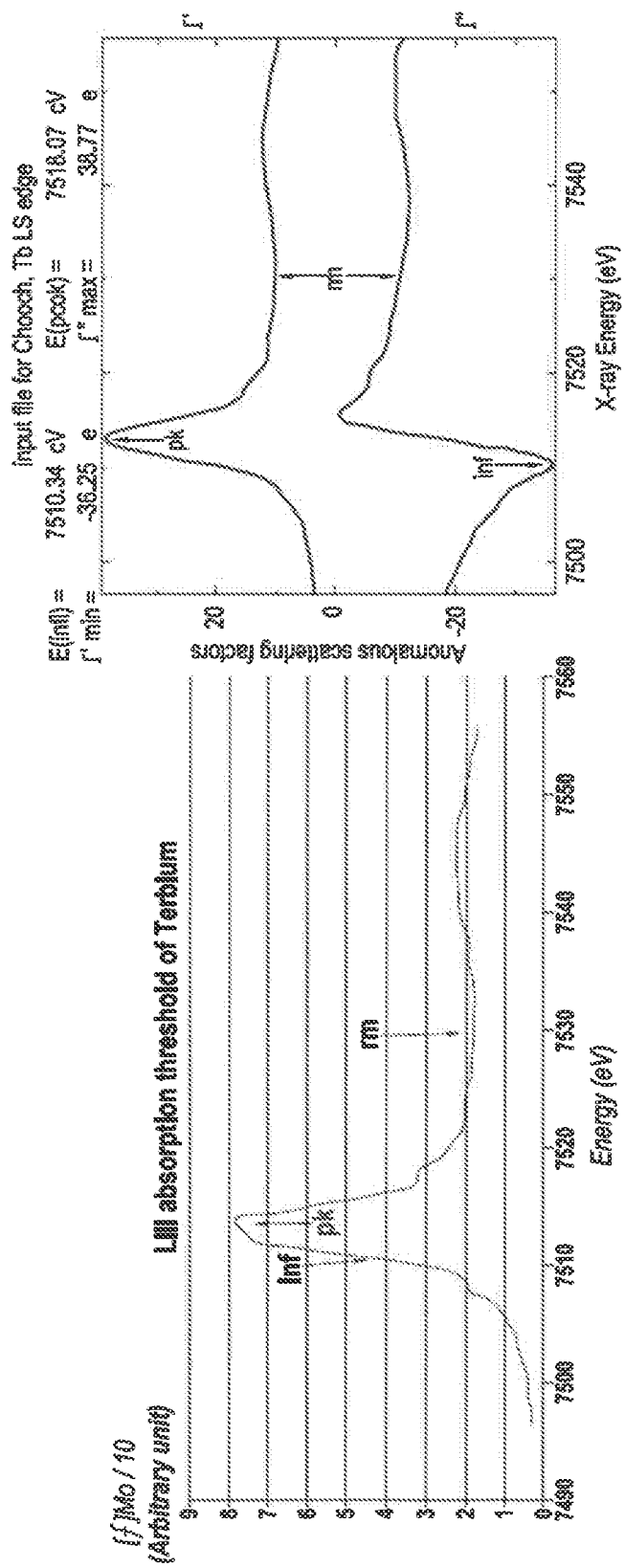

FIG. 10 shows a X-ray fluorescence spectrum measured on a 10 mM solution of complex 10 (left) and processed by the CHOOCH software (right). The wavelengths for recordings that allow optimal use of the anomalous diffusion of lanthanide (here the terbium) are indicated by an arrow.

FIG. 11 shows examples of experimental electron density maps.

FIG. 12 shows images obtained from the HTXIab crystallization robot.

EXAMPLES OF ACHIEVEMENTS

Part I: Synthesis and Characterization of Complexes

The following abbreviations are used:

Me=methyl; Moz=methoxyybenzyloxycarbonyl; Boc=tert-butoxycarbonyl; Ms=mesyl; Et=ethyl; TA=ambient temperatura; Ac=acetyl; DCM=dichloromethane; TACN=triazacyclononane; DMF=dimethylformamide; TFA=trifluoroacetic acid; ACN=acetonitrile; CCM=thin layer chromatography Starting Materials and Characterization All starting materials, solvents and salts of lanthanide were purchased from Sigma-Aldrich®, Acros Organics® and TCI® with purities greater than 98% for organic compounds and greater than 99.99% for lanthanide salts. These products were used directly without additional purification.

Chromatographs were carried out on neutral alumina activity III obtained by hydration of Acros Organics® alumina activity I (60Å) and on silica gel Acros Organics® (60 Å). The formed complexes have all been purified by Sephadex® steric exclusion column LH20.

The NMR spectra ($^1H$, $^{13}C$) were recorded on two Bruker® Advance devices operating at 500.10 MHz and 125.75 MHz for $^1H$ and $^{13}C$ respectively, and at 300 MHz for $^1H$ for the second. Chemical displacements are partially reported per million (ppm) relative to the tetramethylsilane signature ($^1H$, $^{13}C$), with residual solvent peaks being used as internal reference.

The exact mass measurements were carried out at the Joint Centre for Mass Spectrometry (Villeurbanne, France).

A) Preparation of a First Batch of Triazacyclononane-Based Ligands/Complexes (TACH)

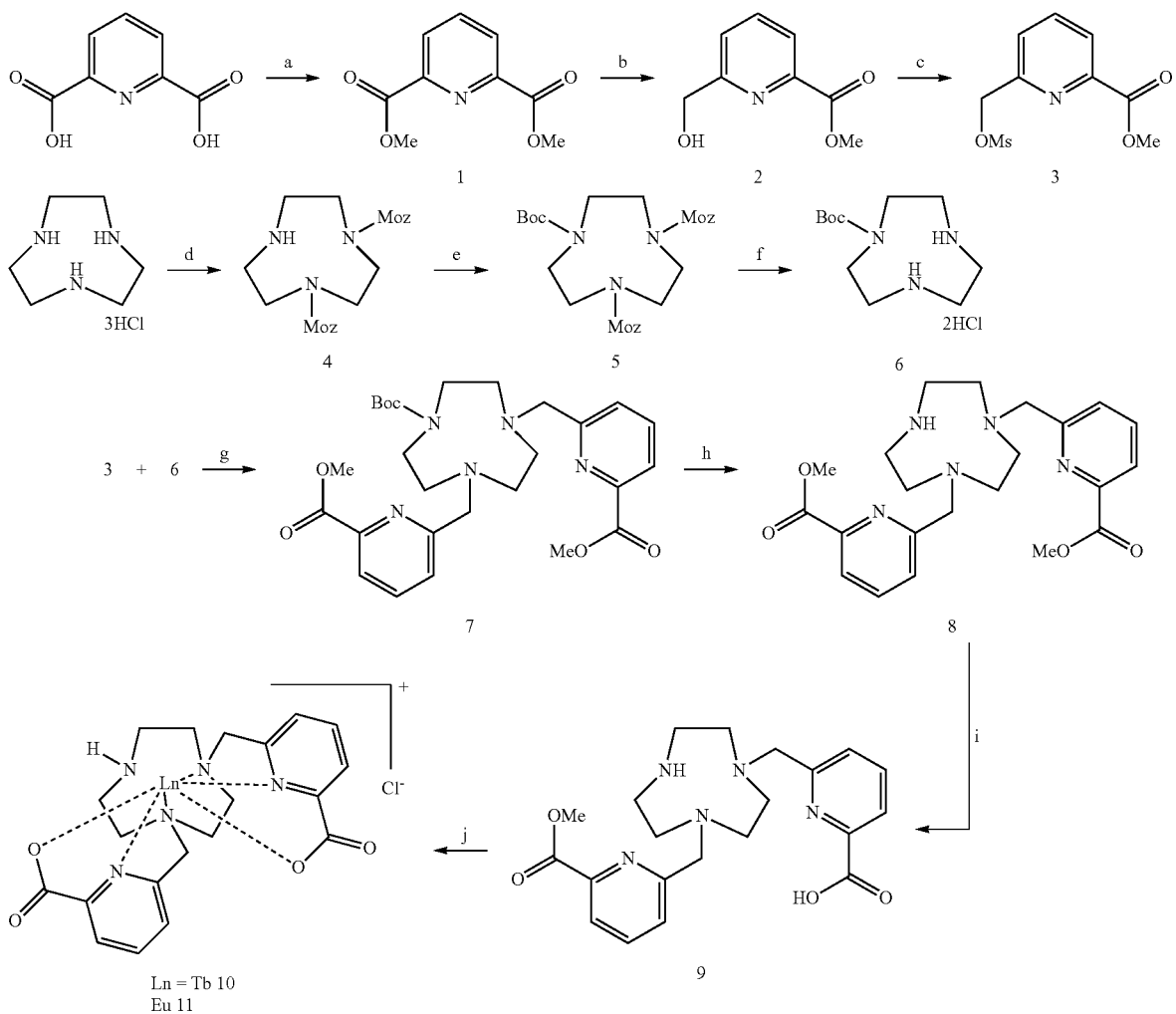

a) HCl (cat.) in MeOH
b) NaBH$_4$ in DCM/MeOH
c) MsCl, Et$_3$N in DCM
d) Moz-on, Et$_3$N in ACN
e) Boc-O-succinimide in DCM
f) H$_2$, Pd/C in MeOH
g) Na$_2$CO$_3$ in MeOH/H$_2$O
h) TFA in DCM
i) Na$_2$CO$_3$ in ACN
j) Na$_2$CO$_3$ in H$_2$O then LnCl$_3$, 6(H$_2$O) with Ln = Tb or Eu Compound 6 was prepared according to the procedure previously described in patent application WO2013/011236A1.

A1) Preparation of Compound 1

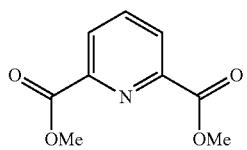

To a suspension of 20 g dipicolinic acid (0.12 mol, 1 eq.) in 120 mL methanol, 1 mL concentrated sulphuric acid is added. The mixture is carried in reflux for 24 hours. After cooling, the crystallized product is filtered and rinsed with cold methanol to give, after drying, 18 g of white crystalline powder of compound 1. (R=78%). $^1$H-NMR (300 MHz, CDCl$_3$) δ (ppm)=8.26 (d, J=8 Hz, 2H), 7.99 (t, J=8 Hz, 1H), 3.98 (s, 6H).

A2) Preparation of Compound 2

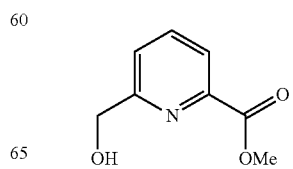

18 g compound 1 (92 mmol, 1 eq.) are dissolved in 450 ml methanol and cooled to 0° C. 3.8 g NaBH₄ (101.2 mmol, 1.1 eq.) are then added. The mixture is then stirred 30 min at 0° C. and 30 min further, leaving the temperature slowly rising to RT. The reaction is stopped by adding 50 mL HCl (1M in H2O), then the organic phase is extracted with 100 mL dichloromethane. After washing the organic phase with brine (up to pH=7), drying with Na₂SO₄ and evaporation, the obtained product is purified by chromatography on silica gel (eluent: DCM/AcOEt 9/1 v/v up to pure AcOEt). We obtain 6 g of a white solid of compound 2 (R=40%).
¹H-NMR (300 MHz, CDCl₃) δ (ppm)=8.01 (d, J=8 Hz, 1H), 7.84 (t, J=8 Hz, 1H), 7.53 (d, J=8 Hz, 1H), 4.85 (d, J=3 Hz, 2H), 3.98 (s, 3H), 3.69 (bs, 1H).

A3) Preparation of Compound 3

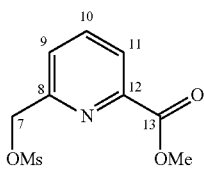

3 mL of Et₃N (22 mmol, 3.2 eq.) is added to a solution of 1.2 g of alcohol 2 in 50 mL of dichloromethane at 0° C. and rapidly followed by 0.79 mL of mesyl chloride (10.2 mmol, I, 5 eq.). The mixture is then allowed to return at room temperature before heating for 1 hour at 50° C. Then 40 mL of water is added and the dichloromethane mixture (3×20 mL) is extracted. The obtained oily residue, after drying and evaporation of the organic phases, is finally purified on silica gel (eluent: CH₂Cl₂) to obtain a colorless oil of compound 3 which crystallizes in the freezer.
¹H NMR (500 MHz, CDCl₃) δ 8.12 (d, J=7.7 Hz, 1H), 7.93 (t, J=7.8 Hz, 1H, H10), 7.70 (d, J=7.8 Hz, 1H), 5.44 (s, 2H, H7), 4.01 (s, 3H, OMe), 3.15 (s, 3H, OMs).
¹³C NMR (126 MHz, CDCl₃) δ 165.33 (C13), 154.59 (s), 147.92 (s), 138.45 (C10), 125.41 (s), 125.13 (s), 71.11 (C7), 53.23 (OMe), 38.24 (OMs).

A4) Preparation of compound 6

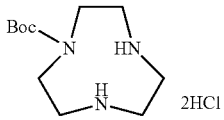

Compound 6 is prepared by the method described above, (a) WO2013011236A1; b) 1.S. J. Butler, B. K. McMahon, R. Pal, D. Parker and J. W. Walton, Chem. Eur. J., 2013, 19, 9511-9517.)

A5) Preparation of compound 7

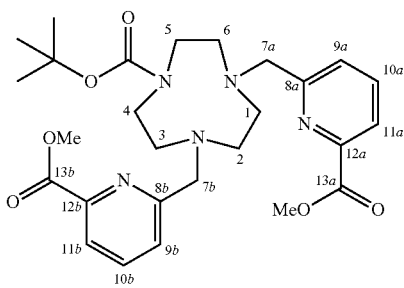 [SMILES: COC(=O)c1cccc(CN2CCN(Cc3cccc(C(=O)OC)n3)CCN(C(=O)OC(C)(C)C)CC2)n1]

360 mg of compound 6 (1.19 mmol) and 760 mg of sodium carbonate (7.15 mmol, 6 eq.) are dried under reduced pressure in a schlenk before adding 100 mL of acetonitrile. Under argon, 710 mg of compound 3 (2.74 mmol, 23 eq.) are added to the suspension before heating for 12 h at 70° C. After return to room temperature, the mixture is filtered on sintered (porosity 4) and concentrated under reduced pressure. The product is purified by alumina chromatography (activity III, eluent DCM then DCM/MeOH 96/4 v/v) to finally obtain a yellow oil of compound 7 (532 mg, Yield: 80%).
¹H NMR (500 MHz, CDCl₃) δ 7.99 (dd, J=6 Hz, 2H, H11), 7.86-7.65 (m, 4H, H9), 3.98 (s, 10H, H7+OMe), 3.39 (d, J=30 Hz, 4H, H4H5), 3.11 (s, 2H, H3H6), 2.95 (s, 2H, H3'H6'), 2.66 (d, J=31 Hz, 4H, H1H2), 1.44 (s, 9H, boc).
¹³C NMR (126 MHz, CDCl₃) δ 166.01, 166.09 (C13), 161.43, 161.60 (C8), 155.88(CO(boc)) 147.45 (C12), 137.42 (d,C10), (s), 126.19, 126.46 (C9), 123.70 (C11), 79.48 (C(boc)), 63.70 (d, C7), 57.21 (C1C2), 55.37 (s), 55.11 (s), 54.67 (s), 53.04 (OMe), 50.54, 49.95 (C4C5), 28.72 (CH₃(boc)).

A6) Preparation of Compound 8

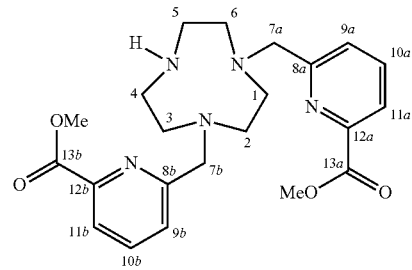

In 100 mL dichloromethane, 5 mL trifluoroacetic acid is added to a 427 mg solution of compound 7. After 5 hours of agitation at room temperature, the mixture is evaporated by removing the TFA by drive with several toluene additions. The resulting residue is purified by alumina chromatography (activity III, eluent DCM/MeOH (gradient 1% to 7%)). The viscous yellowish solid obtained from compound 8 is stored under argon in the freezer (mass: 315 mg, yield: 90%).
¹H NMR (500 MHz, CDCl₃) δ 7.96 (dd, J=7.7, 0.5 Hz, 2H, H11), 7.71 (t, J=8 Hz, 2H, H10), 7.42 (dd, J=7.9, 0.5 Hz, 2H), 3.98 (d, 10H, H7+OMe), 3.40 (t, J=5 Hz, 4H, H4H5), 3.03 (t, J=5 Hz, 4H, H3H6), 2.71 (s, 4H, H1H2).
¹³C NMR (126 MHz, CDCl₃) δ 65.37 (C13), 159.43 (C8), 147.59 (C12), 137.87 (C10), 126.10 (C9), 124.02 (C11), 60.95 (C7), 54.60 (C1C2), 53.31 (OMe), 51.66 (C3C6), 46.52 (C4C5).

NB: the synthesis of this compound has been previously described in the following reference: A. Nonat, C. Gateau, P. H. Fries, M. Mazzanti, Chem. Eur. J., 2006, 12, 7133.

A7) Preparation of Compound 9

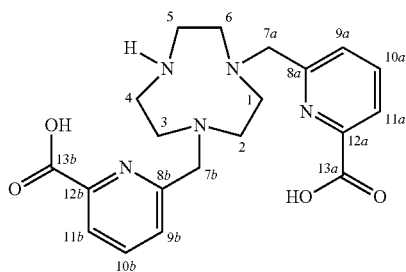 [SMILES: O=C(O)c1cccc(CN2CCNCCN(Cc3cccc(C(=O)O)n3)CC2)n1]

Ligand 9 is generated in situ by saponification of diester 8 in the presence of sodium carbonate $Na_2CO_3$ (2 eq.) in a MeOH/H20 mixture (1/1, v/v) stirred for 3 hours at 50° C.

$^1$H NMR (500 MHz, $D_2O$) δ 7.77 (d, J=7.1 Hz, 2H, H9), 7.69 (t, J=7.7 Hz, 2H, H10), 7.29 (d, J=7.2 Hz, 2H, H11), 3.86 (s, 4H, H7), 3.08 (t, J=5.9 Hz, 4H, H4H5), 2.91 (t, J=5.9 Hz, 4H, H3H6), 2.65 (s, 4H, H1H2).

$^{13}$C NMR (126 MHz, $D_2O$) δ 173.22 (C13), 158.44 (C8), 153.01 (C12), 138.23 (C10), 125.17 (C11), 122.40 (C9), 60.27 (C7), 50.53 (C1,C2), 47.12 (C3,C6), 44.10 (C4,C5).

A8) Preparation of Compound 10

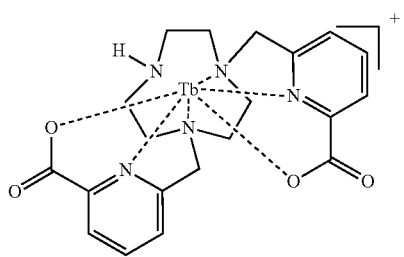

After reaction for 3 h at 50° C. of 110 mg diester 8 (0.26 mmol) with 83 mg $Na_2CO_3$ (0.78 mmol, 3.0 eq.) and neutralization by HCl (1M), the disappearance of the ester is verified by NMR. 96 mg terbium chloride (0.26 mmol, 1 eq.) are added to compound 9, formed in situ, before stirring the mixture for 12 hours at 50° C. Solubilized in a minimum of methanol, complex 10 is then separated from the various salts by centrifugation. The last traces of salts are removed by passing through a steric exclusion column (LH20, Sephadex®, eluent: water). MS (ESI-TOF) calculated M+: 556.1003; measured: 556.0990

A9) Preparation of Compound 11

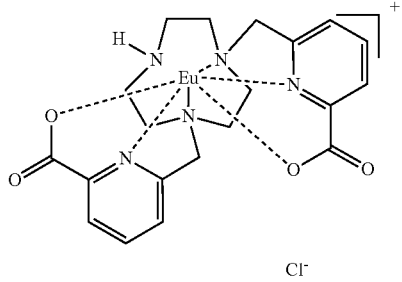

An identical protocol to that/the one used for the preparation of Complex 10 is used with 170 mg diester 8 (0.4 mmol) and 219 mg EuCl3,6H20 (0.6 mmol, 1.5 eq.). MS (ESI-TOF) calculated M+: 550.0962; measured: 550.0957.

B) Preparation of a Second Series of Triazacyclononane-Based Ligands (TACN)

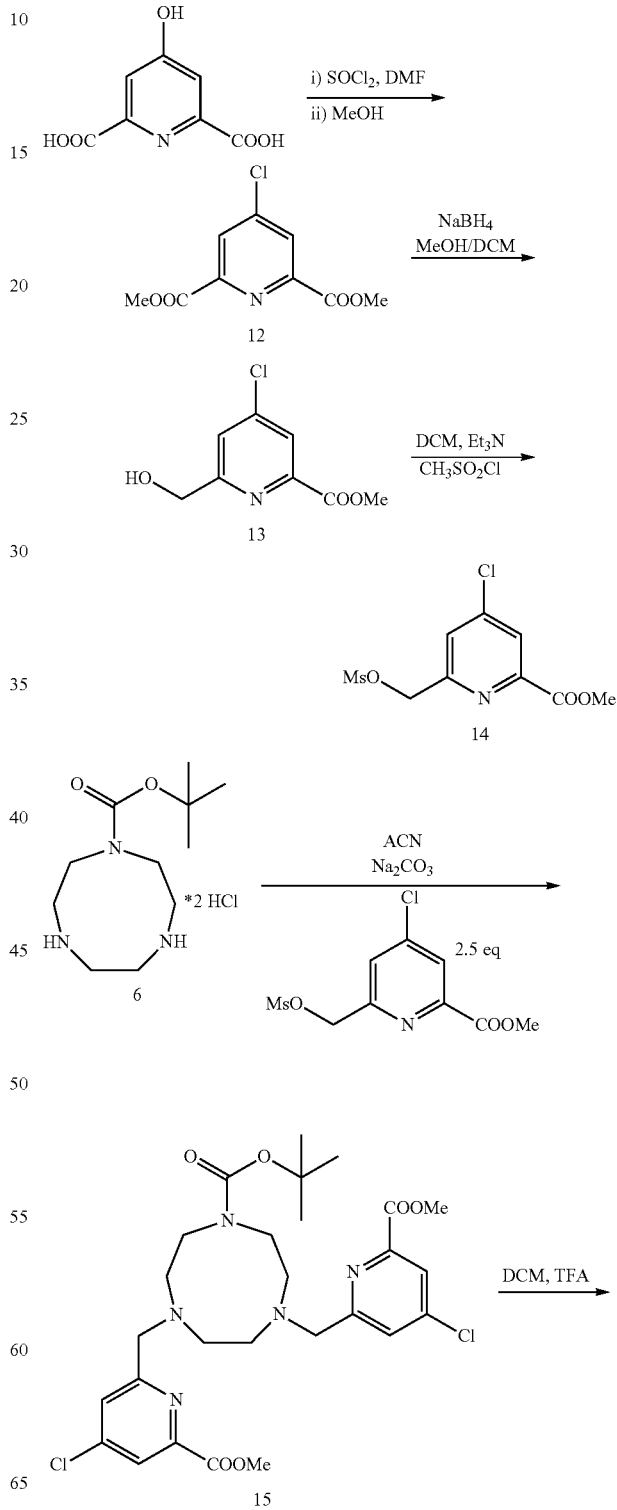

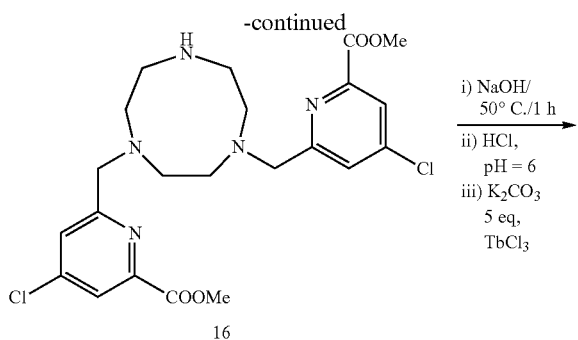

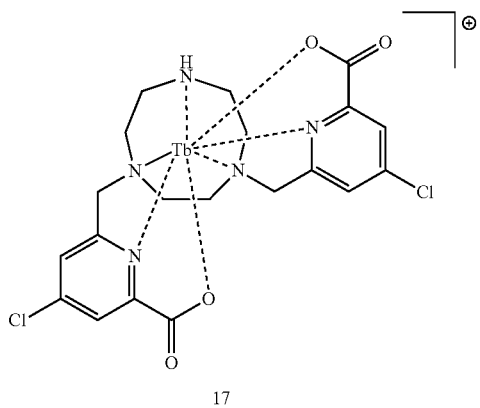

B1) Preparation of Compound 12

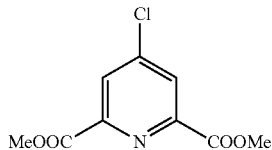 [SMILES: COC(=O)c1cc(Cl)cc(C(=O)OC)n1]

15 g of monohydric chelidamic acid (0.075 mol, 1 eq.) are dissolved in 120 mL of thionyl chloride under argon. The suspension is cooled to 0° C. and 3 mL DMF are added. The reaction mixture is then stirred for 12 hours with reflux. Volatiles are evaporated after several toluene additions to remove the last traces of $SOCl_2$. The resulting yellowish solid is then dissolved in methanol and the mixture is refluxed for 12 hours to complete the reaction. After evaporation of the solvent, the residue is taken up by dichloromethane and washed successively with a saturated solution of $NaHCO_3$, water and brine. The organic phase is then dried on $Na_2SO_4$, filtered and evaporated. Pure compound 12 is obtained by recrystallization in methanol to obtain 8.3 g of white crystalline powder. (R=44%).

$^1$H-NMR (300 MHz, $CDCl_3$) δ (ppm)=8.29 (s, 2H), 4.03 (s, 6H).

B2) Preparation of Compound 13

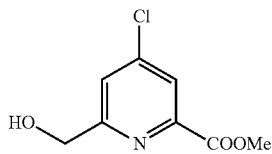 [SMILES: COC(=O)c1cc(Cl)cc(CO)n1]

6 g of compound 12 (0.026 mol, 1 eq.) are dissolved in 250 mL of a DCM/methanol mixture (150/100, v/v) and the solution is cooled to 0° C. Then, 1.09 g of $NaBH_4$ (0.029 mol, 1.1 eq.) are added in one step before stirring the mixture for 30 min at 0° C. and 30 min at RT. The reaction is stopped by the addition of 50 mL hydrochloric acid (1M) and 100 mL of water. The organic phase is then washed with water to a pH=7, then washed in brine, dried on $Na_2SO_4$ and evaporated. The reaction crude is then purified on silica gel (eluent: DCM/acOEt 1/1 v/v) to obtain after evaporation 1.5 g of a white powder of compound 13 (R=30%).

$^1$H-NMR (300 MHz, $CDCl_3$) δ (ppm)=8.00 (bd, 1H), 7.60 (bd, 1H), 4.85 (d, J=7 Hz, 2H), 3.99 (s, 3H) 3.48 (t, J=7 Hz, 1H).

B3) Preparation of Compound 14

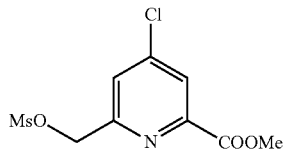

1.5 g of compound 13 (7.4 mmol, 1 eq.) are dissolved in 200 mL dichloromethane and 3 mL triethylamine are added (22.2 mmol, 3 eq.). Then 0.87 mL of mesyl chloride is added (11.1 mmol, 1.5 eq.) slowly and a progressive yellow coloring of the mixture is observed. The reaction progress is followed by CCM and stopped after 30 min. 100 mL of a saturated solution of $NaHCO_4$ are added and the organic phase is washed with water (up to pH=7) and brine. The organic solution is then dried on Na2S04 and evaporated to give 2 g of a yellow oil of compound 14 used without further purification (quantitative yield).

$^1$H-NMR (300 MHz, $CDCl_3$) δ (ppm)=8.1 (s, 1H), 7.68 (s, 1H), 5.40 (s, 2H), 4.01 (s, 3H), 3.17 (s, 3H).

B4) Preparation of Compound 15

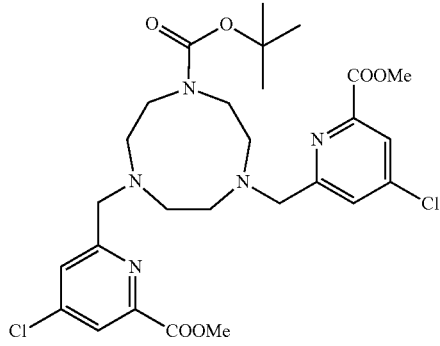 [SMILES: COC(=O)c1cc(Cl)cc(CN2CCN(Cc3cc(Cl)cc(C(=O)OC)n3)CCN(C(=O)OC(C)(C)C)CC2)n1]

200 mg of triazacyclononane mono-boc (0.7 mmol, 1 eq.) are suspended in 100 mL of dry acetonitrile with 420 mg of anhydrous sodium carbonate. 463 mg of compound 3.3 (1.75 mmol, 2.5 eq.) are then added. After cooling, the mixture is sintered to remove the carbonate before evaporation of the solvent. The residue is taken up in dichloromethane and purified by alumina column chromatography (activity III, eluent: dichloromethane and ethyl acetate). 250 mg of a yellow solid of compound 15 (R=63%).

$^1$H-NMR (300 MHz, $CDCl_3$) δ (ppm)=8.00 ppm (d, J=1 Hz, 1H), 7.99 (d, J=1 Hz, 1H), 7.89 (d, J=1 Hz, 1H), 7.72 (d, J=1 Hz, 1H), 3.99 (m, 10H), 3.39 (m, 4H), 3.03 (m, 4H), 2.67 (m, 4H), 1.48 (s, 9H). LC-MS: [M+H]$^+$=596.2 m/z.

B5) Preparation of Compound 16

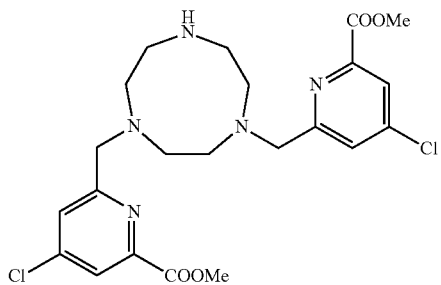 [SMILES: COC(=O)c1cc(Cl)cc(CN2CCNCCN(Cc3cc(Cl)cc(C(=O)OC)n3)CC2)n1]

3 mL trifluoroacetic acid is added to a 110 mg solution of compound 15 in 60 mL of dichloromethane, The mixture is then stirred for 12 hours at room temperature. The solvent is then evaporated and the TFA is evaporated by several additions of a methanol/toluene mixture. The residue is then taken up by 50 mL of dichloromethane and washed with water to pH=7. The organic phase is then dried on $Na_2SO_2$ and evaporated to obtain 100 mg of white powder of compound 16. (R–95%).

$^1$H-NMR (300 MHz, $CDCl_3$) δ (ppm)=7.97 (d, J=1 Hz, 2H), 7.54 (d, 7=1 Hz, 2H), 4.04 (s, 6H), 4.03 (s, 4H), 3.35 (m, 4H), 3.00 (m, 4H), 2.76 (s, 4H).

$^{13}$C-NMR (75 MHz, $CDCl_3$) δ (ppm)=163.91, 160 (q, J=40 Hz), 147.58, 146.99, 126.49, 125.22, 60.37, 53.80, 53.56, 53.28, 45.39.

HR-MS: [M+H]$^+$=496.1501 m/z, theor. for $C_{22}H_{28}Cl_2N_4O_4$ is 496.1513 m/z.

B6) Preparation of Compound 17

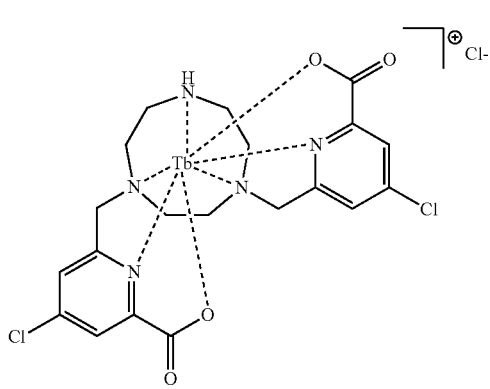

100 mg of compound 16 (0.2 mmol, 1 eq.) are suspended in 30 mL of water and 32 mg of sodium hydroxide (0.81 mmol, 4 eq.) are added. The mixture is then stirred at 60° C. during one hour. The complete hydrolysis of the ester functions is confirmed by LC-MS. The solution is then cooled and its pH is adjusted to 5 with a progressive addition of a hydrochloric acid solution (1M). 5 mL of methanol is then added before introducing 42 mg of sodium carbonate to the solution. 91 mg of $TbCl_3$, $6H_2O$ are added before stirring the mixture at 50° C. for 12 hours. After return to ambient temperature, the insoluble salts are filtered on sintered glass before evaporation of the solvents to obtain 300 mg of raw product. The complex is purified by steric exclusion chromatography (Sephadex® LH20, eluent: water) to finally obtain 55 mg of a colorless crystalline product (yield=44%).

$^1$H-NMR (300 MHz, $D_2O$) δ (ppm)=121.1, 83.90, 69.15, 52.71, 46.23, 29.58, 26.06, −0.96, −11.39, −20.2, −33.57, −36.26, −44.20, −70.35, −91.19, −92.47, −120.84.

HR-MS: M$^+$=624.0213 m/z, theor. for $C_{20}H_{21}Cl_2N_5O_4Tb$ 624.0219 m/z.

C) Preparation of a Third Series of Triazacyclononane-Based Ligands (TACN)

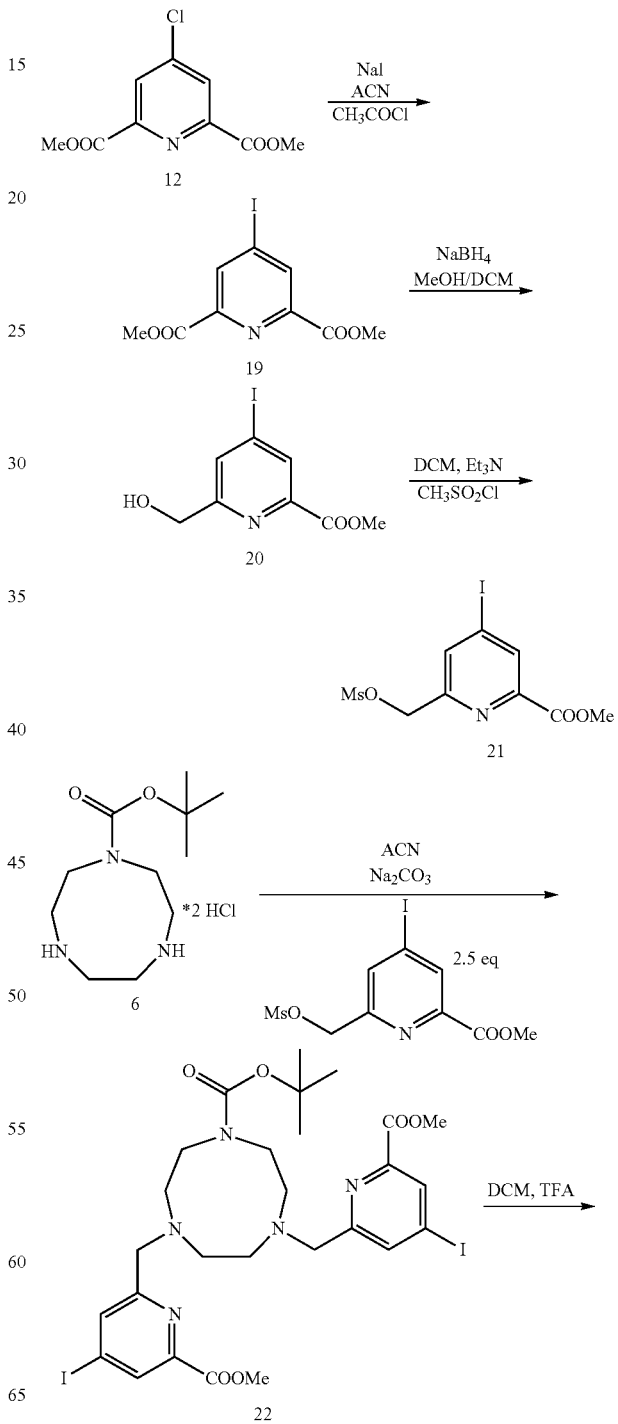

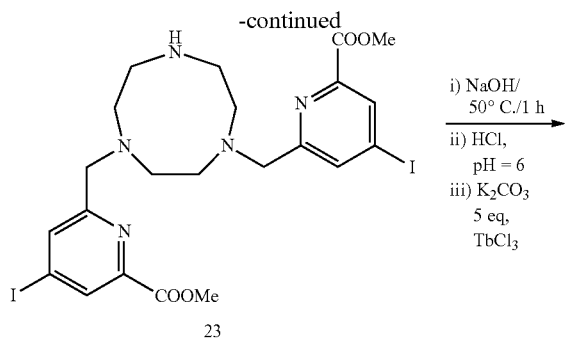

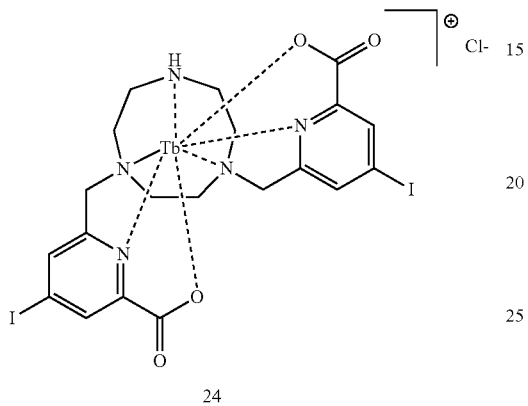

C1) Preparation of Compound 19

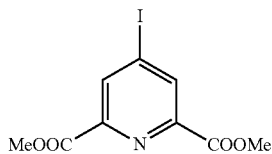 [SMILES: COC(=O)c1cc(I)cc(C(=O)OC)n1]

8.3 g of compound 12 (36 mmol, 1 eq.) are dissolved in 200 mL acetonitrile and 54 g sodium iodide are added (0.36 me, 10 eq.) and 10 mL acetyl chloride (0.108 mol, 3 eq.). The suspension is then placed in an ultrasonic bath for 3 hours. Then 200 mL of dichloromethane are added and the organic phase is washed with a saturated solution of sodium hydrogen carbonate. The organic phase is then washed with water up to pH=7, dried on sodium sulfate and evaporated to obtain 10.7 g of off-white solid of compound 19, used without further purification (R=92%).

$^1$H-NMR (300 MHz, CDCl$_3$) δ (ppm)=8.65 (s, 2H), 4.02 (s, 6H).

C2) Preparation of Compound 20

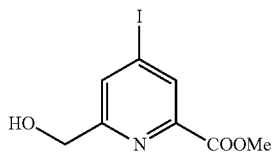 [SMILES: COC(=O)c1cc(I)cc(CO)n1]

1.39 g sodium borohydride (36.6 mol, 1.1 eq.) are added to a solution of 10.7 g (33.3 mmol, 1 eq.) of compound 19 in 200 ml of a mixture of methanol/dichloromethane (140/60) and cooled to 0° C. The mixture is then stirred for 30 min at 0° C. and 30 min at room temperature. The reaction is then stopped by adding 50 mL of an hydrochloric acid solution (1M). The organic phase is then washed with water up to pH=7, dried on Na$_2$SO$_4$ and evaporated. The raw product is then purified on silica gel (eluent: dichloromethane with progressive addition of methanol (0 to 10%)) to obtain 5 g of a white powder of compound 20. (R=51%).

$^1$H-NMR (300 MHz, CDCl$_3$) δ (ppm)=8.39 (bd, 1H), 7.97 (bd, 1H), 4.82 (d, J=5 Hz, 2H), 3.99 (s, 3H) 3.04 (t, J=7 Hz, 1H).

C3) Preparation of Compound 21

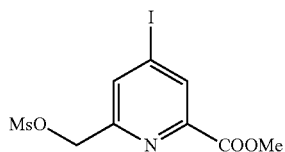 [SMILES: COC(=O)c1cc(I)cc(COS(C)(=O)=O)n1]

To a solution of 1 g of compound 20 (3.4 mmol, 1 eq.) and 1.4 mL of triethylamine (10.2 mmol, 3 eq.) in 120 mL of dichloromethane are added 0.4 mL of mesyl chloride (5.1 mmol, 1.5 eq.). After 30 minutes of stirring (reaction followed by TLC), 100 mL of a saturated solution of NaHC03 is added. The organic phase is then washed with water, dried on Na$_2$SO$_4$ and evaporated. 1.1 g of yellow oil of compound 21 is obtained and used without further purification (R=95%).

$^1$H-NMR (300 MHz, CDCl$_3$) δ (ppm)=8.46 (s, 1H), 8.04 (s, 1H), 5.36 (s, 2H), 4.00 (s, 3H), 3.16 (s, 3H).

C4) Preparation of Compound 22

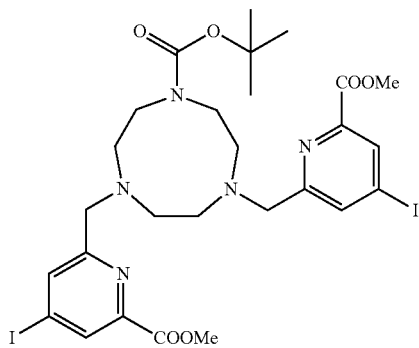 [SMILES: COC(=O)c1cc(I)cc(CN2CCN(Cc3cc(I)cc(C(=O)OC)n3)CCN(C(=O)OC(C)(C)C)CC2)n1]

60 mg of triazacyclononane mono-boc 6 (0.2 mmol, 1 eq.) are suspended in 50 mL of dry acetonitrile under argon with 140 mg of anhydrous Na$_2$CO$_3$ (1.2 mmol, 6 eq.). A solution of 184 mg of compound 21 (0.5 mmol, 2.5 eq.) in dry acetonitrile is then added and the mixture is stirred for 12 hours at 60° C. under argon. After cooling, the mixture is filtered on sintered and evaporated. The residue is taken up by dichloromethane and purified on an alumina column (activity III; eluent: dichloromethane followed by ethyl acetate) to obtain 110 mg of pure compound 22 in the form of a white pasty solid (R=71%). $^1$H-NMR (300 MHz, CDCl$_3$) δ (ppm)=8.34 (s, 2H), 8.22 (s, 1H), 8.11 (s, 1H), 3.97 (s, 6H), 3.94 (s, 4H), 3.4-2.58 (m, 12H), 1.47 (s, 9H).

$^{13}$C-NMR (75 MHz, CDCl$_3$) δ (ppm)=164.6, 162 (d, J=14 Hz), 155.61, 147.6 (d, J=14 Hz), 135.3 (d, J=14 Hz), 132.7, 106.6, 79.5, 63.1, 56.6, 54.9, 54.4, 53.1, 50.8, 50.2, 28.7. LC-MS: [M+H]$^+$=780.0 m/z.

C5) Preparation of Compound 23

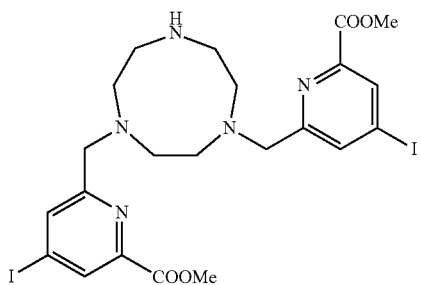 [SMILES: COC(=O)c1cc(I)cc(CN2CCNCCN(Cc3cc(I)cc(C(=O)OC)n3)CC2)n1]

110 mg of compound 22 (0.14 mmol, 1 eq.) are dissolved in 50 mL of dichloromethane, then an excess of trifluoroacetic acid is added (3 mL). The mixture is then stirred at room temperature for 12 hours. The solvent is then evaporated and a mixture of 20 mL of dichloromethane and 10 mL of water is added. The aqueous phase is neutralized by adding a saturated solution of $NaHCO_3$ and extracted with dichloromethane. All the organic phases are dried on sodium sulfate and evaporated. The result is 100 mg of white solid (quantitative yield) of compound 23, which is used without further purification.

[71]H-NMR (300 MHz, $CDCl_3$) δ (ppm)=8.23 (s, 2H), 7.83 (s, 2H), 3.92 (s, 10H), 3.27 (s, 4H), 2.92 (s, 4H), 2.67 (s, 4H).
$^{13}$C-NMR (75 MHz, $CDCl_3$) δ (ppm)=164, 159.98, 147.81, 134.86, 133.14, 107.08, 59.85, 5336, 52.65, 49.87, 45.33.
HR-MS: $[M+H]^+$=680 m/z, theor. for $C_{22}I_2H_{28}N_2O_5$ 680.0225 m/z.

C6) Preparation of Compound 24

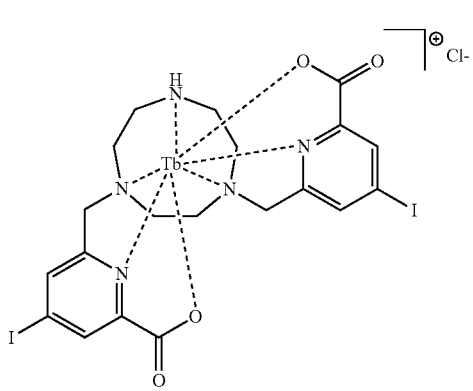

100 mg of compound 23 (0.15 mmol, 1 eq.) are suspended in 30 mL of water and 24 mg of sodium hydroxide (0.81 mmol, 4 eq.) are added. The mixture is then stirred at 60° C. for one hour. The complete hydrolysis of the ester functions is confirmed by LC-MS. The solution is then cooled, and its pH is adjusted to 5 with a progressive addition of a hydrochloric acid solution (1M). 5 mL of methanol are then added before introducing 42 mg of sodium carbonate to the solution. 66 mg of $TbCl_3$, $6H_2O$ (0.18 mmol, 1.2 eq) are added before stirring the mixture at 50° C. for 12 hours, after return to ambient temperature, the insoluble salts are filtered on sintered glass before evaporation of the solvents to obtain 200 mg of raw product. The complex is purified by steric exclusion chromatography (Sephadex® LH20, eluent: water) to obtain 36 mg of a colorless crystalline product (30% yield).

$^1$H-NMR (300 MHz, $D_2O$) δ (ppm)=122.8, 84.95, 82.17, 70.62, 49.22, 25.03, 20.8, −0.89, −8.54, −19.41, −33.05, −41.19, −67.6, −88.49, −90.57, −125.1.
HR-MS: $[M+H]^+$=807.8921 m/z, theor. for $C_{20}H_{21}I_2N_5O_4Tb$ 807.8931 m/z.

D) Preparation of a Fourth Series of Triazacyclononane-Based Ligands (TACH)

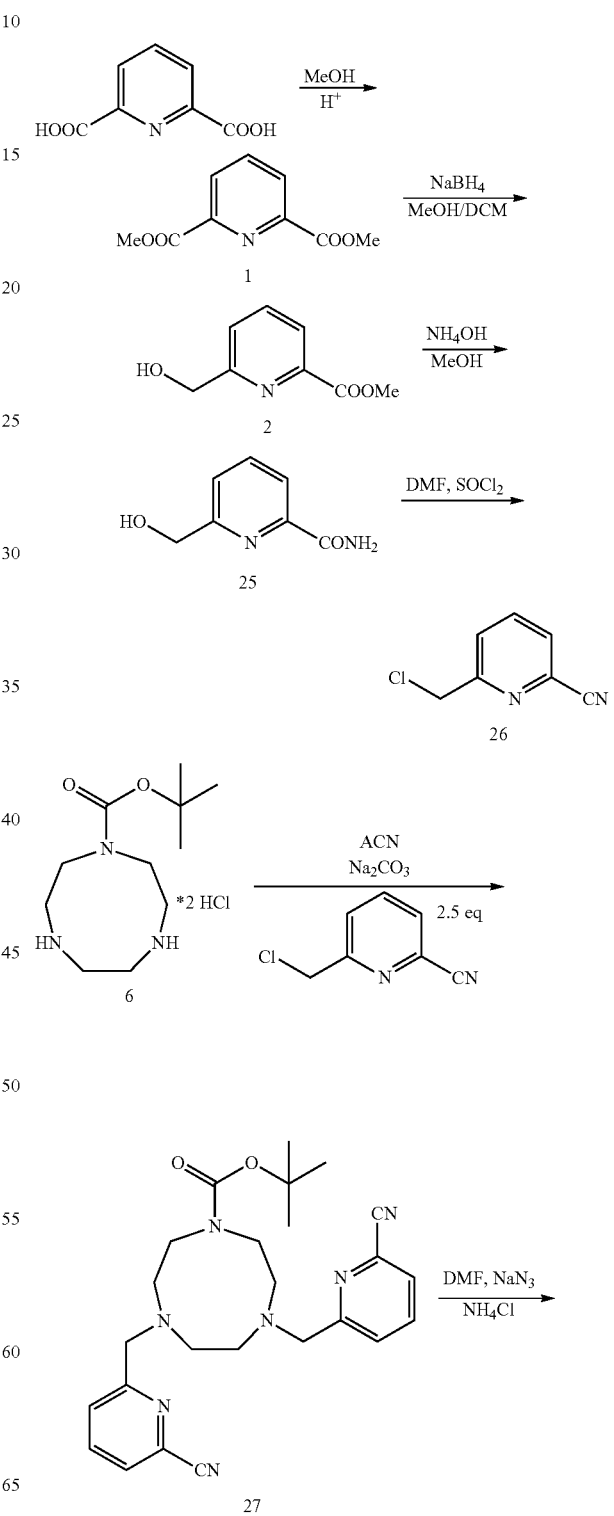

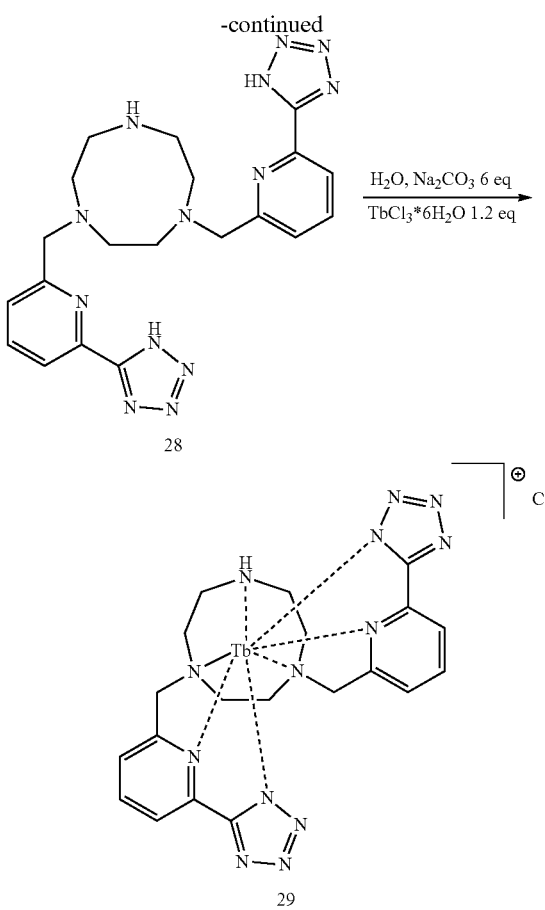

28

29

D1) Preparation of Compound 25

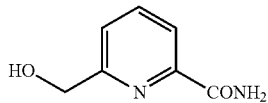

1 g of compound 2 (6 mmol, 1 eq.) is dissolved in 100 mL methanol and 8 mL of a 30% aqueous ammonia solution (60 mmol, 10 eq.). This mixture is stirred at room temperature for 12 hours. The solvents are then evaporated to give 900 mg of a white solid of the pure compound 25 (=quantitative).

$^1$H-NMR (300 MHz, $C_2D_6SO$) δ (ppm)=8.14 (bs, 1H), 7.96 (t, J=8 Hz, 1H), 7.88 (d, J=8 Hz, 1H), 7.61 (bd, J=8 Hz, 2H), 4.64 (s, 2H).

LC-MS: $[M+H]^+$=153.2 m/z.

D2) Preparation of Compound 26

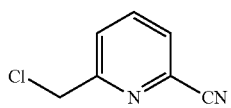

To 1 g of compound 25 (6.6 mmol, 1 eq.) in 20 mL DMF at 0° C., 4 mL thionyl chloride (53 mmol, 8 eq.) are added. The mixture is stirred for 2 hours, before being allowed to return to room temperature in 15 minutes. 150 mL water is then added before extracting the product with 30 mL dichloromethane. The organic phase is then washed with water to pH=7, washed in brine, dried on $Na_2SO_4$ and evaporated. The resulting residue is purified by silica gel chromatography (eluent: dichloromethane) and leads to the production of 720 mg of a white solid of compound 26 (R=55%).

$^1$H-NMR (300 MHz, $CDCl_3$) δ (ppm)=7.89 (t, J=8 Hz, 1H), 7.75 (d, J=8 Hz, 1H), 7.65 (d, J=8 Hz, 1H), 4.69 (s, 2H).

LC-MS: $[M+H]^+$=153.3.

D3) Preparation of Compound 27

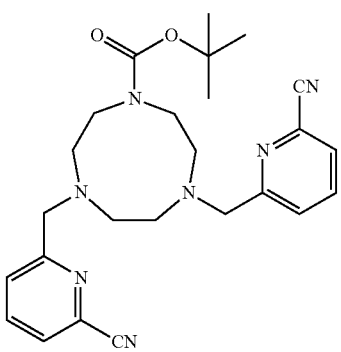 [SMILES: CC(C)(C)OC(=O)N1CCN(Cc2cccc(C#N)n2)CCN(Cc2cccc(C#N)n2)CC1]

120 mg of triazacyclononane protected by a mono-Boc (0.4 mmol, 1 eq.) are dissolved in 50 mL of dry acetonitrile under argon with 252 mg of anhydrous anhydrous $Na_2CO_3$ (2.4 mmol, 6 eq.). A 151 mg solution of compound 26 (1 mmol, 2.5 eq.) in dry acetonitrile is then added and the mixture is stirred for 12 hours at 60° C. under argon. After cooling, the mixture is filtered on sintered and evaporated. The residue is taken up by dichloromethane and purified on an alumina column (activity III; eluent: dichloromethane followed by ethyl acetate) to give 160 mg of compound 27 in the form of a white pasty solid (R=83%).

$^1$H-NMR (300 MHz, $CDCl_3$) δ (ppm)=7.79 (dt, $^3$J=8 Hz, $^4$J=1 Hz, 2H), 7.70 (bd, J=8 Hz, 2H), 7.57 (dt, $^3$J=8 Hz, $^4$J=1 Hz, 2H), 3.91 (s, 4H), 3.36 (m, 4H), 3.03 (m, 4H), 2.66 (m, 4H), 1.47 (s, 9H).

LC-MS: $[M+H]^+$=462.2 m/z.

D4) Preparation of Compound 28

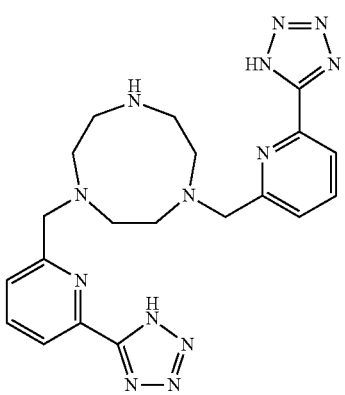 [SMILES: c1cc(CN2CCNCCN(Cc3cccc(-c4nnn[nH]4)n3)CC2)nc(-c2nnn[nH]2)c1]

225 mg of $NaN_3$ (3.5 mmol, 10 eq.) and 185 mg of dry $NH_4Cl$ are added to a 160 mg solution of compound 27 (0.35 mmol, 1 eq.) in 40 mL of dry DMF under argon. The mixture is stirred at 120° C. for 12 hours. After cooling, sintered filtration and evaporation of the solvents, a residue is obtained, which is taken up by 50 mL hydrochloric acid (1M) and placed in an ultrasonic bath for 2 hours. HR-MS [M+H+]: 604.1439 th 604.1447

D5) Preparation of Compound 29

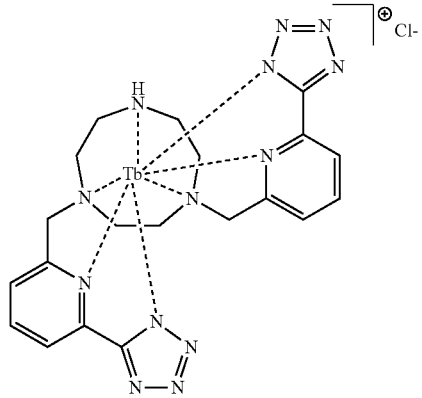

155 mg of compound 28 (0.35 mmol, 1 eq.) are suspended in 10 mL of water with 220 mg Na$_2$CO$_3$ (2.08 mmol, 6 eq.). After 10 min of stirring, 155 mg TbCl$_3$*6H$_2$O (0.42 mmol, 1.2 eq.) are added. The solution is then stirred for 12 hours at room temperature. After evaporation of solvents, the raw product is purified on a steric exclusion column. (Sephadex® LH20 in water) to finally obtain 40 mg of crystalline white solid (yield=20%).

HR-MS: [M+H]$^+$=604.1439 m/z, theor. for C$_{20}$H$_{23}$N$_{13}$Tb 604.1427 m/z.

E) Preparation of a First Series of Ligands Based on 1,7-dioxa-4,10-Diazacyclododecane

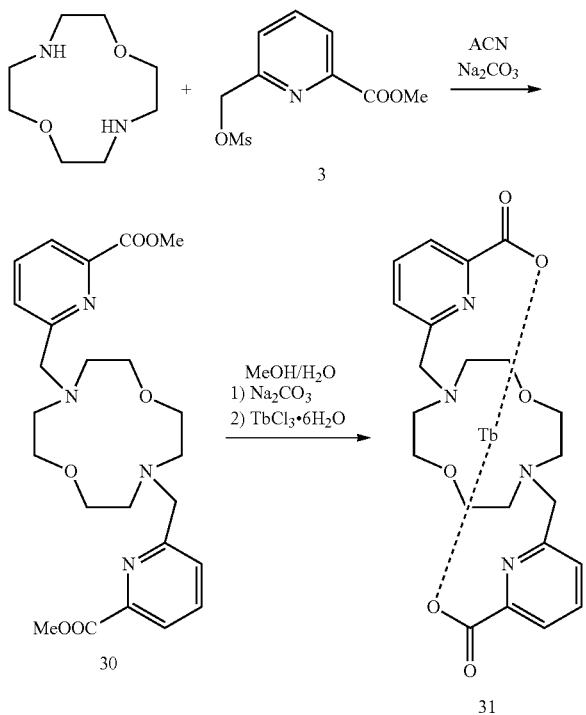

Compound 31 is prepared according to the method previously reported (M. Mato-Iglesias, Adrián Roca-Sabio, Z. Pálinkás, D. Esteban-Gómez, C. Platas-Iglesias, E. Tóth, A. de Blas, T. Rodríguez-Blas, Inorg. Chem., 2008, 47, 7840).

Part II: Crystallographic Studies

A) Model Proteins Studied 5 proteins, of which three commercial proteins were selected. The structure of these five proteins was known. These five proteins were chosen because of their physico-chemical differences. They belong to various organisms, have broad thermal properties and an oligomeric state ranging from monomer to hexamer. Tests with proteins of unknown structure were also carried out.

a. Commercial Proteins

The three commercial proteins selected are chicken's egg white lysozyme (HEWL), Thaumatococcus danielli Thaumatin and Tritirachium album Proteinase K. These three proteins are model proteins for crystallogenesis. They are purchased under freeze-dried form. They were solubilized in milliQ water just prior to crystallogenesis experiments at the desired concentration. These are presented in Table 1 below.

TABLE 1

Commercial proteins used and associate supplier

| Proteins | Number of amino acids | Supplier product reference | Sequence |
| --- | --- | --- | --- |
| HEWL | 129 | 10 837 059 001 Roche | SEQ ID No 1 |
| Thaumatine | 207 | T7638 Sigma | SEQ ID No 2 |
| Proteinase K | 384 | 03 115 879 001 Roche | SEQ ID No 3 |

The conditions of native crystallization (i.e., without addition of complexes depending on the invention) of these proteins are known and described in Table 2 below. These conditions were used to characterize the effect of lanthanide complexes on the crystallogenesis of these commercial proteins.

TABLE 2

Usual crystallization conditions for commercial proteins

| Proteins | Buffer | Salt |
| --- | --- | --- |
| HEWL | 100 mM sodium acetate pH 4.6 | 0; 5 to 2M NaCl |
| Thaumatine | 100 mM Bis tris propane pH 6.5 | 0.9 to 1.4M Tartrate twice of Na+ and K+ |
| Proteinase K | 100 mM sodium cacodylate pH 6.5 | 0.9 to 1.5M ammonium sulfate | a. Non-Commercial Proteins

The two non-commercial proteins (known structures) are *Pyrococcus horikoshii* Protease 1 and *Pyrococcus furiosus* reductase Glyoxylate hydroxypyruvate reductase. These two proteins have been purified according to the protocols described in the references below:

Protease 1 protein purification protocol of *P. horikoshii*: Xinlin Du et al. Crystal structure of an intracellular protease from *Pyrococcus horikoshii* at 2-A resolution. 2000. Flight 97. N° 26. PNAS.

Protocol for purification of *P. furiosus* Glyoxylate reductase protein: Thesis of Louise Lassalle, defended on 19 Dec. 2014 in Grenoble: Molecular bases of piezophilic adaptation: structural and biochemical studies of key enzymes of metabolism coming from archaeas and bacteria isolated in the seabed. Link: http://www.theses.fr/s98711.

The technical details concerning these proteins are given in Table 3 below:

TABLE 3

Characteristics of non-commercial proteins used

| Name | Organism | Vector | Size (amino acids) | Physico-chemical characteristic | Link to sequence | Biological unit |
|---|---|---|---|---|---|---|
| GRHPR | P. furiosus | pET41 | 336 | Hyperthermophilic | 1 | dimeric |
| Protease 1 | P. horikoshii | pET41c | 166 | Thermophilic | 2 | hexameric |

Sequence of GRHPR: SEQ ID No 4
Sequence of protease 1: SEQ ID No 5

The crystallization conditions for these two proteins are described in Table 4 below. These conditions allow the proteins to crystallize in their native form and are extracted from the same references as purification protocols.

TABLE 4

Crystallization conditions of the non-commercial proteins used

| Proteins | Buffer | Salt | Precipitating agent |
|---|---|---|---|
| GRHPR | 100 mM sodium acetate pH 5.2 | 100 mM NaCl | 14 to 24% |
| Protease 1 | PEG 400 | | |

The five proteins described above are the reference proteins for characterizing the effects of lanthanide complexes.

c. Unknown Proteins

The specificities of the three proteins with unknown structure are described in Table 5 below. The structure of the MDH-ANC80 protein was determined using the lanthanide 17 complex. The individual steps will be described individually in a separate section.

TABLE 5

Characteristics of proteins of unknown structure on which lanthanide complexes according to the invention have been tested

| Name | Organism | Vector | Size AA | characteristics | Name | Organism |
|---|---|---|---|---|---|---|
| pb6 | Phage T5 | pET41 | 464 | Viral protein | 1 | monomer |
| MDH-ANC80 | The sequence was generated bio-informatically | pET41c | 309 | Halophilic | 2 | Tetramer |

Sequence of Pb6: SEQ ID No 6
Sequence of MDH: SEQ ID No 7

No crystallisation conditions were published for these two proteins. Sequence SEQ ID N° 1 to 7 are presented in ANNEXE1.

The ANC80 Malate Dehydrogenase (MDH) purification protocol is described in the literature (Madern et al. 1995 230 (3): 1088-95 Eur. J. Biochem).

The protocol for the purification of pb6 was established by Cécile Breyton's team from the M&P group of the Institut de Biologie Structurale and is as follows:

Pb6 Purification Protocol:
Expression system=E. coli BL21 (DE3) transformed with LIM1 (Kan R) His tag with cleavage site "Tobacco Etch Virus".
Preculture medium LB classic medium with 50 g/ml of kanamicyne
Classical culture in LB medium: Seeding with an optical density of 0.1 and 50 µg/ml of Kanamicyne.
After 6 hours of culture, centrifugation 30 minutes 4000 rpm
Bacteria freezing at −80° C.
Breakage
Recovery in lysis buffer 50 mM Tris pH 8, 150 mM NaCl, 2 mM MgCl2 in the presence of antiprotease and DNase
Microfluidizer Bacteria Lysis 6×12000 psi
Centrifugation: 20 minutes at 14,000 rpm
Nickel affinity column
Balancing buffer=20 mM Tris pH 8, 250 mM NaCl, 15 mM Imidazole
Elution buffer—20 mM Tris pH 8, 200 mM Imidazole
Flow rate=1 ml/min
Dilution of the elution fractions to the fifth with distilled water to reduce conductivity.
Ion exchange column (HT Q 1 ml)
Balancing buffer=20 mM Tris pH 8
Elution buffer=20 mM Tris pH 8 1M NaCl
Emission by linear gradient
Flow rate=1 ml/min
Concentrator concentrate with 30 kDa diaphragm
Desalination by gel filtration in a pH 8 20 Mm sorting buffer B) Automated Crystallization/Stability of Lanthanide Complexes a. The HTXIab Platform.

To determine the crystallization conditions of a protein, the HTXIab platform was used to screen a wide range of crystallization conditions. These conditions are all described in the Tables in Appendix 2A and 2B and derived from https://embl.fr/htxlab/
index.php?option=com_content&view=article&id=38&Itemid=172.

A conventional screening consists of 6 crystallization plates of 96 wells each, representing 576 conditions.

The studies conducted on MDH-ANC80 and Pb6 used the conditions described in Appendix 2A.

The studies carried out on the other proteins were carried out under the conditions described in Appendix 2B, due to a change due to the supplier.

Complex Stability

The stability studies were performed under the conditions described in Appendix 2A. Lanthanide complexes based on tris-dipicolinate (DPA) [Ln(DPA)$_3$]$^{3-}$ have been shown to exhibit" self-crystallization "for certain crystallization conditions. In particular, the presence of divalent cations, high salt concentrations, the presence of MPD caused the self-crystallization of this type of complex (Doctoral thesis of R. Talon defended in Grenoble on Jun. 6, 2012). Two concentrations of Ln(DPA)$_3^{3-}$ have been evaluated (25 and 100 mM). Thus, out of 576 conditions, more than a quarter of the conditions lead to self-crystallization/precipitate formation of Ln(DPA)$_3^{3-}$ at 100 mM and of the order of 8% when used at 25 mM.

Equally, the stability of complex 10 was evaluated at 3 different concentrations (10, 50 and 100 mM). Complex 10, even at a concentration of 100 mM, exhibits increased stability. Indeed, no crystal of the complex was observed, as detailed below where only precipitates were detected.

Summary of the screening of the 6 classical plates for 100 mM of complex 10:

Plaque Hampton 3

Slight precipitation observed in the presence of NaHPO$_4$ or KHPO$_4$.

Plaque Hampton 5

Mostly PEGs in this case 100% of the drops are clear.

Plaque Hampton 4

Mostly salts. Some conditions are redundant with the Hampton 3 plate. Similar effect in the presence of HPO$_4^-$ with slight observed precipitation.

Plaque Qiagen 1

Mixture of PEGs, salts and metals. A slight precipitate is observed in the presence of cadmium acetate.

Plaque Hampton 6

Slight precipitate observed in the presence of a mixture of metals (cadmium, zinc, cobalt).

Plaque Hampton 2

Slight precipitate in the presence of NaF and (NH$_4$)$_2$PO$_4$

Below is a detailed description of the conditions that lead to these precipitates: With 100 mM of Complex 10 added to the standard conditions:

Hampton Plate 4: 21 precipitated conditions No. A7, B7, C7, C7, A8, B8, ABCD 9, 10, 11 and 12 (mainly ammonium phosphate)

Hampton Plate 5: No precipitate

Quiagen Plate 1: 6 precipitated conditions No. D6, B9, F9, F9, F9, D10, E10

Hampton 6 plate: 4 precipitated conditions No. A3, B3, C3, H8

Hampton Plate 2: 7 precipitated conditions No. C2, C5, B6, A7, C7, C7, A12, B12

Hampton Plate 3: 4 precipitated conditions No. H3, E4, A6, E5

This represents a total of 42 precipitated conditions. On a screening of 576 conditions this is equivalent to 7.3%;

No false positives like with DPA.

With 10 mM of complex 10 added to the standard conditions:

Hampton Plate 4: No precipitate marked as observed with some 100 mM, some trace of precipitate for ABCD line 12

Qiagen Plate 1: a slightly precipitated condition for E10

Wizard plate I and II rigaku 5 precipitated conditions No. E6, C7, B9, C10, H11

JCSG plate: 3 precipitated conditions No. D2 G5, A6

PACT Qiagen Plate: 5 precipitated conditions No. E1, A5, A6, E11, C12

PEGs Qiagen Plate: No precipitated condition

A total of 18 conditions with slight traces of precipitation. (3.2% of the screening) considering that drops with some traces of precipitate were described as "precipitated". The amount and number of precipitating assays have nothing to do with the observed precipitates at 100 mM of complex 10, nor at 25 mM of (DPA)$_3^{3-}$.

It should be noted that the presence of these precipitates is not incompatible with the appearance of protein crystals. In fact, manual crystallization tests of the *C. aurantiacus* MDH protein in the presence of cadmium have made it possible to obtain crystals in the presence of 50 mM of complex 10.

C) Screening of New Crystallization Conditions

To carry out a screening of six plates at the HTXIab platform, 100 µl of protein solution are required. In order to have a direct comparison, the native protein (without lanthanide complex) and the protein in the presence of 10 mM complex 10 were screened in parallel in the same crystallization plates.

a. Protocol for the Preparation of Protein Samples Containing Lanthanide Complex.

Lanthanide complexes were stored under powder form at 4° C. The mass corresponding to 10 mM per 100 µl of protein solution was weighed on a precision scale. The powder was centrifuged to form a pellet. This pellet was taken up by 100 µl of the protein solution. A two-minute centrifugation was carried out to eliminate any aggregates. The solution was then changed to a new tube. This protocol has been applied for all proteins sent to the robot.

b. Determination of New Conditions for Unknown Protein pb6

The most interesting conditions in terms of crystallogenesis and allowing the crystallization of pb6 are listed in Table 6. The conditions under which crystals were formed only in the presence of 10 mM of complex 10 are indicated in bold (they are pb6-I and pb6-4).

TABLE 6

Crystallization conditions for pb6 protein obtained in the HTX robot in the absence or presence of complex 10

| Condition reference | Native/ complex 10 | Buffer | Salt | Precipitating agent |
|---|---|---|---|---|
| pb6-1 | 10 mM complex 10 | 0.1M HEPES pH 7 | 0 | 10% PEG 6K |
| pb6-2 | Native | 0.1M sodium acetate pH 4.6 | 0 | 8% PEG 4K |
| pb6-3 | Native | 0.1M MES pH 6 | 0 | 15% PEG 5KMME |
| pb6-4 | 10 mM complex 10 | 0.1M Bis tris pH 6.5 | 0.2M ammonium acetate | 45% MPD |

The pb6-I condition was reproduced manually in the laboratory and also gave crystals. The use of complexes according to the invention makes it possible to double the number of conditions that led to crystallization.

c. Determination of New Conditions for Unknown Protein MDH-ANC80

The most interesting conditions in terms of crystallogenesis and allowing the crystallization of protein ANC80 are listed in Table 7. The conditions which allowed the crystals to be generated only in the presence of 10 mM of complex 10 are mentioned in bold (they are ANC-1 and ANC-2).

TABLE 7

Crystallization conditions for the ANC80 protein obtained at the HTX robot in absence or in the presence of complex 10

| Condition reference | Native/complex 10 | Buffer | Salt | Precipitating agent |
|---|---|---|---|---|
| ANC-1 | 10 mM complex 10 | 0.1M MES pH 6 | 0 | 65% MPD |
| ANC-2 | 10 mM complex 10 | 0.1M HEPES pH 7.5 | 0.2M $MgCl_2$ | 30% PEG 400 |
| ANC-3 | Native | 0.1M MES pH 6.5 | 0.01M zinc sulfate | 25% PEG 550MME |
| ANC-4 | Native and 10 mM complex 10 | 0.1M MES pH 6 | 1M lithium chloride | PEG 6K 30% |

The ANC-1 condition was replicated in the laboratory and allowed crystal growth (Paragraph D. a). The use of complexes according to the invention makes it possible to triple the number of conditions that led to a crystallization.

d. Statistics on the Crystals of the Different Proteins Studied on the HTXIab Platform Table 8 below presents the number of conditions that led to crystals after conventional screening (576 commercial conditions for complex 10 and 480 for complex 31) at the HTXIab platform for the different proteins studied. The values indicated correspond to an observation of the crystallization plates after 85 days. The column "unique conditions" corresponds to the number of conditions that lead to crystallization in the presence of complexes, but no crystallization under the same conditions in the absence of complex (called natives).

Complex 10, like complexes 17 and 31, have all a nucleating effect. However, complexes 17 and 31 are less effective than complex 10. For example, complex 31 appears to be less effective than complex 10 for proteinase K. However, the 4 conditions leading to crystallization in the presence of complex 31 are different from those leading to native crystals. Those crystals are potentially of better quality. Obtaining new conditions leading to crystallization is therefore a step forward.

D) Hand-Held Laboratory Crystallizations

Commercial proteins (Paragraph A.a.) were manually crystallized according to known customary crystallization conditions (Table 2). The crystallization conditions described in Table 2 were therefore reproduced in the presence of 10 or 17 complexes at a concentration of 10 mM. To achieve these manual crystallization ranges, the crystallization drops were prepared according to the following scheme: 1.5 μl protein solution +1.5 μl complex solution at a concentration of 10 mM+1.5 μl precipitant solution. In order to highlight a potential effect of lanthanide complexes on crystallization, the precipitating agent range has been adjusted to be at the edge of the crystallization zone and eventually extended beyond when an effect was observed.

Thus, in the case of the lysozyme protein, a marked nucleating effect was observed. The nucleating effect should be understood here as the growth of crystals in the presence of the lanthanide complex at low concentrations of precipitating agents, concentrations which do not allow the formation of native crystals. In order to clearly highlight this nucleation phenomenon induced by complexes according to

TABLE 8

| Protein | Protein concentration (mg/ml) | Organism | Commercial protein | Complex | Complex concentration (mM) | Total conditions | Native hits * |
|---|---|---|---|---|---|---|---|
| Lysozyme (HEWL) | 20 | *Gallus* | yes | 10 | 10 | 576 | 17 |
| Proteinase K | 20 | *T. Album* | yes | 10 | 10 | 576 | 22 |
| Pho Protease 1 | 11.5 | *P. Horikoshii* | no | 10 | 10 | 576 | 82 |
| Pho Protease 1 | 11.5 | *P. Horikoshii* | no | 17 | 10 | 576 | 82 |
| Glyoxylate hydroxyl pyruvate reductase | 10 | *P. Furiosus* | no | 10 | 10 | 576 | 38 |
| Glyoxylate hydroxyl pyruvate reductase | 10 | *P. Furiosus* | no | 17 | 10 | 576 | 38 |
| Thaumatin | 20 | *T. Daniellii* | yes | 10 | 10 | 576 | 4 |
| Lysozyme (HEWL) | 20 | *Gallus* | yes | 31 | 10 | 480 | 9 |
| Proteinase K | 20 | *T. Album* | yes | 31 | 10 | 480 | 16 |

\* Condition leading to crystallization in the absence of complex (native conditions)
\*\* Condition leading to crystallization with addition of complex The conditions leading to crystallization correspond to conditions leading to the appearance of crystals potentially exploitable for diffraction experiments. Complex 10 thus allows a significant increase in the number of crystallization conditions for the following proteins: HEWL and Pho protease I. While its effect may appear to be less effective in the case of Proteinase K and Thaumatin, that is not the case. Indeed, the introduction of Complex 10 does not lead to a significant increase in the number of lanthanide hits, but the conditions obtained are largely different from native conditions (21 for Proteinase K and 2 for Thaumatin). We increase then the number of potential conditions for obtaining crystals of the protein of interest, It should be noted that in the case of the Protease I protein with complex 10, gaining 113 conditions is covering a wide range of different crystallization conditions. This proves once again that complex 10 is compatible with all the physico-chemical conditions that can be found in commercial crystallization kits.

the invention, phase diagrams have been made by determining the ranges of concentration of precipitating agents and of protein that allow the crystals to be obtained.

a. Phase Diagrams for Native Chicken's Egg White Lysozyme and in the Presence of 10 mM Complex 10 or Complex 17

Phase diagrams of the lysozyme protein obtained after 2 days and 15 days of growth are shown in FIG. 5:

Each crystallization condition was made in triplicate. After only two days of crystal growth, a clear difference was observed. In the presence of complex 10 or 17, crystals were obtained at both low concentrations of protein (5 mg/ml) and precipitating agent.

After 20 days of crystalline growth in the presence of complex 10 or 17 at 10 mM, crystals were obtained over the entire range evaluated. In particular, crystals have appeared for 5 mg/ml of lysozyme and for a precipitating concentration of 500 mM. By comparison, the absence of lanthanide complex only allows the formation of crystals up to 500 mM of NaCl and for concentrations of 20 mg/ml of protein.

For comparison purposes:

MRI complexes, which do not induce nucleating effects, are typically used at concentrations in the range of 50-300 mM.

Lanthanide tris-dipicolinate produced a new crystalline form of lysozyme only when used at concentrations above 50 mM.

The MIPs proposed by Naomi E. Chayen (Saridakis, E., Khurshid, S., Govada, L., Phan, Q., Hawkins, D., Crichlow, G. V., Lolis, E., Reddy, S. M., & Chayen, N. E. (2011). Proceedings of the National Academy of Sciences. 108,11081-11086) lead to crystallization zone offsets of only one to two precipitating agent concentration units. The associated nucleating effects are obtained only for conventional concentrations of lysozyme in the order of 30 mg/ml (Khurshid et al., Automating the application of smart materials for protein crystallization, (2014) Acta cryst D). According to Saridakis et al. (Saridakis, E., Khurshid, S., Govada, L, Phan, Q., Hawkins, D., Crichlow, G. V., Lolis, E., Reddy, S. M., & Chayen, N. E. (2011). Proceedings of the National Academy of Sciences. 108,11081-11086.), the range of crystallization of lysozyme in the presence of their nucleating agents starts from 480 mM of NaCl at a protein concentration of 20 mg/mL. No lysozyme crystal was observed below 460 mM of NaCl. Concerning the thaumatin protein (30 mg/ml) no crystal is observed below 0.2 M tartrate. In the presence of their nucleating agents, they obtain crystals for 0.3 and 0.4 M tartrate (idem complex 10) and native crystals for 0.5 M tartrate.

POM complexes have a nucleating effect only with high concentrations of lysozyme (about 100 mg/ml), which poses solubility problems for most proteins. (A. Bijelic et al Chicken's Egg-White Lysozyme Crystallisation: Protein Stacking and Structure Stability Enhanced by a Tellurium (VI)-Centred Polyoxotungstate Chem Bio Chem 2015, 16,233-241).

b. Phase Diagram for Native Chicken's Egg White Lysozyme and in the Presence of 10 mM Complex 11 (Eu)

The phase diagram obtained in the presence of complex 11 (FIG. 6) is equivalent to that obtained in the presence of complex 10. The nature of lanthanide present within the complex does not influence the observed nucleating effect.

c. Phase Diagrams for Protein of Unknown Structure pb6

The protein pb6 has been purified according to the protocol described above. The condition pb6-1 (Paragraph Cb) obtained at the HTXlab robot was reproduced manually. Phase diagrams were determined. They are shown in FIG. 7. As with lysozyme, the nucleating effect is very important. The crystals obtained in the presence of the lanthanide complex according to the invention are very promising (see FIG. 8) for a crystallographic study.

Crystals obtained in the presence of 10 mM complex 10 are perfectly exploitable for diffraction experiments. Native crystals are too small, too thin and poorly organized. Thus, in the case of the protein pb6, a nucleating and crystallizing effect is observed induced by compound 10.

d. Crystallizing Effect of Lanthanide Complexes 10

If an improvement of crystallization (number of crystals, crystal size, diffraction improvement) is observed with the addition of lanthanide complexes, this is referred to a crystallization effect.

In the case of the crystallization of the Protease 1 protein of *P. horikoshil*, a crystallizing effect was also observed linked to the addition of complex 10. Indeed, the crystals obtained in the presence of 10 mM of complex 10 appeared on average 2.5 times larger than the crystals obtained under the same conditions, but without complex (average size evaluated on 10 crystals present in a photographed drop).

This crystallizing effect is therefore of great interest for X-ray crystallography since the diffraction intensity is proportional to the volume of the irradiated sample. This can thus provide a higher resolution for diffraction data.

E) Luminescence Properties and Applications.

The coordination complexes of terbium and europium (III) are known to have very particular luminescence properties, due to the f-f transitions that result in fine and characteristic emission lines of each element and long lifetimes (ps-ms). It is difficult to induce this luminescence by direct irradiation of the metal ion, because these f-f transitions are prohibited and therefore have very low molecular absorption coefficients. On the other hand, it is possible to sensitize this luminescence by an indirect process, called antenna effect, which consists in exciting an organic ligand containing a chromophore (typically an aromatic group) and transferring this energy to the metal ion (Luminescence of Lanthanide Ions in Coordination Compounds and Nanomaterials, Ed. A. De Bettencourt-Dias, Wiley 2014).

These luminescence properties of the proposed lanthanide complexes can be used in two steps in determining the structure of a protein: a) crystal detection during crystallization and b) crystal centering during the diffraction experiment.

a. Crystal Detection During Crystallization

Detection of crystals can sometimes be complicated, for example when the crystals are small, drowned into a precipitate or obtained at the edge of a crystallization drop. In the particular case of membrane proteins, we can also mention the problem of detecting crystals obtained by the crystallization technique of lipidic cubic phase.

To improve the crystals detection, many suppliers offer microscopes with a UV source, allowing the intrinsic fluorescence of aromatic amino acids, especially tryptophan. Examples include the UV source proposed by Molecular Dimension (http://www.moleculardimensions.com/applications/upload/Xtalight"100.pdf) or the UVEX microscope (http://www.moleculardimensions.com/shopdisplayproducts.asp?id=299&cat=UVEX+UV+Fluorescence+Imaging+systems) offered by the same company.

The use of lanthanide complexes luminescence can help to solve many of the problems mentioned above.

The luminescence of lanthanide complexes according to the invention has therefore been studied, using a UV source currently being marketed by NatXray on a conventional microscope and an external OceanOptics LED UV source (FIG. 9; Excitation wavelength 365 nm; Model LLS-365; http://oceanoptics.com/product/lls-family/) (lysozyme crystals obtained in the presence of 10 mM of complex 10 or MDH ANC80 protein crystals obtained in the presence of 50 mM of complex 17).

Using the NatX-ray system, the crystals obtained in the absence of Complex 10 appear blue (on the left). Conversely, those obtained with this complex appear green (on the right) which results in a contrast increase between the crystals and the surrounding solution. This can also be observed with the system using a UV LED source, since the crystals obtained in the presence of Complex 17 and under UV illumination are easier to identify than when observed in white light. For example, a small crystal is indicated by a white arrow (FIG. 9).

It should also be noted that luminescence is observable at two excitation wavelengths (280 nm and 365 nm).

b. Crystal Centering Aid

This part was evaluated using the IBS-ESRF CRYOBENCH instrument (http://www.isbg.fr/analyses-structurales/cryobench/) and the ESRF FIP-BM30A light line.

The crystals used (lysozyme crystals obtained in the presence of 10 mM of complex 10 or crystals of the protein MDH ANC80 obtained in the presence of 50 mM of complex 17) were conventionally frozen at 100 K on nylon loops.

To take pictures, the same external UV LED light source from OceanOptics was used. The quality of the photos obtained makes it possible to consider different ways for facilitating centering:

- a direct centering through luminescence,
- the use of a spectrophotometer to accurately measure luminescence and search for areas with the highest intensities corresponding to the presence of a crystal. The idea would be to scan the loop with a rather thin UV beam.
- Pre-positioning using luminescence, supplemented by precise centering using the so-called Raster Scanning technique (Aishima et al, Acta D (2010), D66,1032-1035), especially in the case of small crystals or fine needle type crystals.

F) Phasing Potential of Lanthanide Complexes According to the Invention a. Methodology Used The evaluation of the phasing potential of lanthanide complexes according to the invention was carried out in a conventional manner, using different de novo phase-determining methods, representing a panel of commonly used techniques for the determination of biological macromolecular structures. This shows that the use of complexes according to the invention allows a habitual use of phasing methods.

The tested methods are:

The SAD method, which has the advantage of requiring a single crystal and performing a single diffraction recording, The MAD method, which has the advantage of requiring a single crystal, which presupposes recording at several wavelengths and which theoretically produces phases of better quality than the SAD method, The SIRAS method, which involves recording on a protein crystal in the absence of complex and recording on a protein crystal in the presence of complex. This method assumes an excellent isomorphism of both crystals and therefore requires that they have the same crystalline form.

Diffraction data were integrated and scaled with the XDS, SCALA and TRUNCATE programs.

The AutoSharp program (https://www.globalphasing.com/sharp/) has been used. This program automatically searches for the position of heavy atoms, refines them, determines the initial phases and improves them. The program was used with the default settings. The result of the phasing is evaluated on the basis of the merit figures (FOM for "Figure of Merit"), before and after phase improvement.

In a second step, the quality of the phasing was evaluated by automatically reconstructing the model of the protein under consideration. The number of residues modelled is then available compared to the expected number of residues. The Buccaneer program (http://www.ccp4.ac.uk/dist/html/cbuccaneer.html) was used with the default settings and with 10 rebuild cycles.

The diffraction data are conventionally recorded on a synchrotron light line. In order to determine the precise absorption threshold of lanthanide LIII of the lanthanide used, a fluorescence measurement was performed and processed using the Chooch program (http://www.gwyndafevans.co.uk/chooch.html). The recording wavelengths are thus obtained, in order to optimize the use of the lanthanide anomalous signal (SAD and MAD methods). In the case of the SIRAS method and in addition to recording at the LIII threshold of the lanthanide on the derivative crystal, a native crystal recording was made at the wavelength of 0.9798 Å. The results are shown in FIG. 10.

For each of the phasing methods evaluated, the recordings were made at the wavelengths indicated in Table 9:

TABLE 9

Phasing methods used and associated recording energies.

| Phasing methods | Recordings made at energies corresponding to: |
|---|---|
| SAD | pk |
| MAD | pk, inf, rm |
| SIRAS | pk + native at 0.9798 Å | b. Crystallized Protein Diffraction Test in the Presence of 10 mM of Complex 10 or 17

Crystals of co-crystallized proteins in the presence of 10 mM of complex 10 or 17 (nucleating effect conditions of the lanthanide complex) were evaluated in terms of diffraction. The results of this assessment are summarized in Table 10:

TABLE 10

Results of diffraction tests obtained on different crystallized proteins in the presence of lanthanide complexes

| Protein | Resolution (Å) |
|---|---|
| HEWL 10m Complex 10 | >1.5 |
| Thaumatin 10 mM Complex 10 | >1.5 |
| Proteinase K 10 mM Complex 10 | >1.5 |
| Protease1 10 mM Complee 10 | 1.7 |
| PfuGR 10 mM Complex 10 | 2.0 |
| pb6-1 10 mM Complex 10 | 2.6 |
| ANC80-1 10 mM Complex 17 | 1.7 |

In the case of Protease 1 protein, the crystallizing effect manifests itself both by an increase in the average crystal size, as indicated above, and by the resolution obtained for diffraction. The diffraction data recorded on a crystal obtained in the presence of 10 mM of complex 10 has a resolution of 1.7 Å. The best model currently available in the Protein Data Bank is at 2.0 Å (PDB code: 1G2I Publication reference: idem protocol part 1b).

c. De Novo Phasing of Model Proteins

The structures of the different model proteins were determined according to the different methods explained in paragraph F.a.

In addition, phasing attempts were carried out on crystals obtained under nucleating conditions of the complex (i.e. at 10 mM), but the possibility of soaking a crystal obtained in the presence of 10 mM of complex 10 or 17 in a solution similar to the crystallization condition and containing 100 mM of the lanthanide complex was also studied. This was intended to eventually increase the protein's tagging rate and thus facilitating the determination of its structure. The soaking time was about one minute. It should be noted that this soaking technique can also be applied to native crystals (obtained in the absence of lanthanide complex).

To summarize, the following three crystal preparation methods were evaluated for a de novo phasing using lanthanide complexes according to the invention:

co-crystallized crystal in the presence of 10 mM of complex (nucleating condition), co-crystallized crystal in the presence of 10 mM of complex and soaked in a solution containing 100 mM of the same complex, native crystal soaked in a 100 mM solution of the lanthanide complex.

The diffraction data set was obtained in accordance with the methodology explained in paragraph F. a. The results are presented in Table 11 below.

TABLE 11

Results of de novo phasing for model proteins

| Protein | Complex | Concentration | Method | Resolution (Å) | FOM after SHARP | FOM after SOLOMON | Buccanneer % of rebuilt model |
|---|---|---|---|---|---|---|---|
| Hewl | 10 | 10 mM | SAD | 1.8 | 0.428 | 0.881 | 79.1 |
| Hewl | 17 | 10 mM | SAD | 1.8 | 0.314 | 0.839 | 46.5 |
| Protease1 | 17 | Soaking * | SAD | 2.0 | 0.389 | 0.955 | 95 |
| PfuGR | 17 | Soaking* of native crystal | SIRAS | 2.5 | 0.043 | 0.943 | 68 |
| PfuGR | 10 | Soaking * | SAD | 2.5 | 0.184 | 0.923 | 84.5 |

* Soaking: In a cryoprotectant solution containing 100 mM of complex

The high phasing power of the complex objects of the present invention is reflected in the percentage of model reconstructed without manual intervention. The more the quality of the phase determination (depending on the phasing method used, the occupancy of the complex fixing sites, the data quality, etc.), the more the experimental electronic density map can be interpreted by automatic reconstruction programs (such as the Buccaneer program). In the evaluated cases, models automatically rebuilt from 50% to almost 100% of the final model have been obtained.

d. Examples of Electronic Density Obtained After Phasing and Solvent Flattening

An example of experimental electron density obtained using the methods described above for glyoxylate reductase protein and Protease 1 protein are shown in FIG. 11. The glyoxylate reductase crystals were obtained under the conditions described in Table 4 in the presence of 10 mM of complex 10. The Protease 1 protein crystals were obtained under the conditions described in Table 4 in the presence of 10 mM of complex 10 and then soaked in a cryoprotective solution containing 100 mM of complex 10.

In both cases, given the quality of phase determination, easily interpretable experimental electronic density maps are obtained, where one can distinguish side chains of amino acids. A tyrosine for the glyoxylate reductase map and a tryptophan for the Protease 1 Protein map. The images were produced using the coot software.

G) Application of the Technology to the Determination of the Structure of the MDH ANC80 Protein a. Nucleating and Crystallizing Effect: the Case of MDH ANC80

The MDH ANC80 protein concentrated at 10 mg/ml was sent to the crystallization robot for a conventional screening of the 576 conditions. The most promising crystallization condition is the condition ANC-1 in Table 7. The photos obtained in the crystallization robot for this condition are shown in FIG. 12.

This condition was reproduced manually in the laboratory. Crystals appeared in the presence of 10 mM of complex 17 and 10 mM of complex 10 in 7 days. The same condition in native condition (without lanthanide complex) was also performed. After about 3 weeks, crystals of different shapes appeared (not shown).

The native crystals have been tested for diffraction. The resolution is in the order of 2.5 Å. Those crystals have a different symmetry from that obtained for crystals obtained in the presence of complex 10 or 17 (Space group F222) with mesh parameters of 81,140 and 395 Å respectively for a, b, and c. This is compared to the space group obtained for crystals in the presence of complex and the resolution obtained for diffraction data. The crystals in the presence of 10 mM of lanthanide complex diffract at 1.7 Angstrom. Thus, the nucleating and crystallizing effects are properly observed in the case of this protein.

The structure of the ANC80 MDH was determined using the MAD method. Three datasets were recorded on the same crystal at the terbium absorption threshold LIII. An additional dataset was measured at the selenium absorption threshold K to obtain the best possible resolution. The statistics, after integration across all the data collected, are presented in Table 12 below.

TABLE 12

Data collection, phasing and refinement statistics

| | ANC80 10 mM complex 17 | ANC80 10 mM complex 17 |
|---|---|---|
| Data collection | Se threshold K Line id23-2 (ESRF) | Tb threshold $L_{III}$ Line BM30A (ESRF) |
| Space group | R3 | R3 |
| Mesh parameters | | |
| a, b, c (Å) | a = b = 217.5 c = 86.3 | a = b = 217.5 c = 86.3 |

TABLE 12-continued

| Data collection, phasing and refinement statistics | | | | |
|---|---|---|---|---|
| | | pk* | inf | rm |
| Wavelength | 0.8726 | 1.650237 | 1.65087 | 1.64766 |
| Resolution (Å) | 1.85 | 2 | 2 | 2 |
| $R_{merge}$ | 0.093 (0.850) | 0.126 (0.617) | 0.117 (1.035) | 0.116 (1.111) |
| I/sigma(I) | 7.3 (1.3) | 6.8 (2.1) | 7 (1.5) | 7.6 (1.3) |
| Completeness (%) | 98.9 (97.6) | 99.5 (96.8) | 99.6 (97.0) | 99.5 (96.5) |
| Multiplicity | 3.9 (3.9) | 5.5 (5.2) | 5.5 (5.1) | 5.5 (5.0) |
| Automatic rebuilt (Buccaneer) | | 99.2% of the model rebuilt at 2.0 Angström | | |

*according to FIG. 8

The refinement of the model leads to very good quality factors with a R and Rfree factor of 19.2% and 21.2%.

The following luminescent complexes have also been tested at 10 mM and do not have any effect on crystallization:

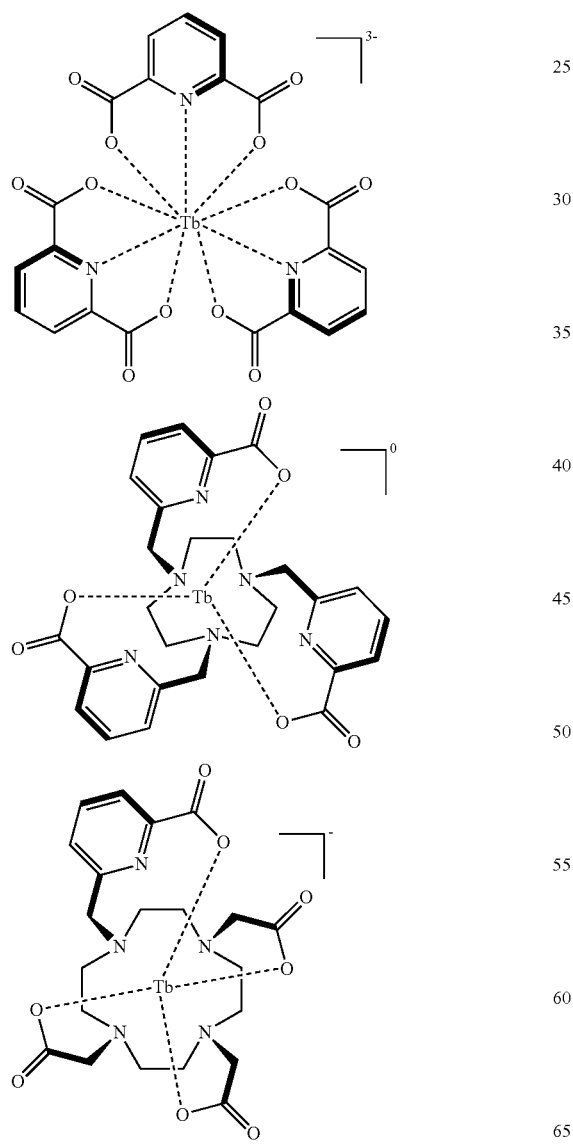

ANNEXE 1

Amino acid sequence of the different proteins tested

Lysozyme (*Gallus gallus*) HEWL: SEQ ID No 1
KVFGRCELAAAMKRHGLDNYRGYSLGNWVCAAKFESNFNTQATNRNTDGSTDYGILQINSR
WWCNDGRTPGSRNLCNIPCSALLSSDITASVNCAKKIVSDGNGMNAWVAWRNRCKGTDVQ
AWIRGCRL Thaumatine (*T. danielli*): SEQ ID No 2
ATFEIVNRCSYTVWAAASKGDAALDAGGRQLNSGESWTINVEPGTNGGKIWARTDCYFDDS
GSGICKTGDCGGLLRCKRFGRPPTTLAEFSLNQYGKDYIDISNIKGFNVPMNFSPTTRGCRGVR
CAADIVGQCPAKLKAPGGGCNDACTVFQTSEYCCTTGKCGPTEYSRFFKRLCPDAFSYVLDKP
TTVTCPGSSNYRVTFCPTA Proteinase K (*Tritirachium Album*): SEQ ID No 3
AAQTNAPWGLARISSTSPGTSTYYYDESAGQGSCVYVIDTGIEASHPEFEGRAQMVKTYYYSS
RDGNGHGTHCAGTVGSRTYGVAKKTQLFGVKVLDDNGSGQYSTIIAGMDFVASDKNNRNCP
KGWASLSLGGGYSSSVNSAAARLQSSGVMVAVAAGNNNADARNYSPASEPSVCTVGASDRY
DRRSSFSNYGSVLDIFGPGTDILSTWIGGSTRSISGTSMATPHVAGLAAYLMTLGKTTAASACR
YIADTANKGDLSNIPFGTVNLLAYNNYQA Glyoxylate and Hydroxypyruvate Reductase (*P. furiosus*): SEQ ID No 4
MKPKVFITRAIPENGINMLEEEFEVEVWEEEREIPREKLLEKVKDVDALVTMLSERIDQEVFENA
PRLRIVANYAVGYDNIDVEEATRRGIYVTNTPDVLTNATADHAFALLLATARHVVKGDKFVRS
GEWKRKGIAWHPKWFLGYELYGKTIGIVGFGRIGQAIARRAKGFNMRILYYSRTRKSQAEKEL
GAEYRPLEEVLKESDFVILAVPLTKEIMYMINEERLKLMKPTAILVNIARGKVVDTKALIKALKE
GWIAGAGLDVFEEEPYYNEELFSLDNVVLTPHIGSATFEAREAMAELVARNLIAFKRGEIPPTLV
NKEVIKIRKPGFNEQ Protease 1 (*P. horikoshii* OT3): SEQ ID No 5
MKVLPLTANEFEDVELIYPYHRLKEEGHEVYIASFERGTITGKHGYSVKVDLTFDKVNPEEFDAL
VLPGGRAPERVRLNEKAVSIARKMFSEGKPVASICHGPQILISAGVLRGRKGTSYPGIKDDMIN
AGVEWVDAEVVVDGNWVSSRVPADLYAWMREFVKLLK Pb6 major protein of the phage T5 tail : SEQ ID No 6
MSLQLLRNTRIFVSTVKTGHNKTNTQEILVQDDISWGQDSNSTDITVNEAGPRPTRGSKRFN
DSLNAAEWSFSTYILPYKDKNTSKQIVPDYMLWHALSSGRAINLEGTTGAHNNATNFMVNFK
DNSYHELAMLHIYILTDKTWSYIDSCQINQAEVNVDIEDIGRVTWSGNGNQLIPLDEQPFDPD
QIGIDDETYMTIQGSYIKNKLTILKIKDMDTNKSYDIPITGGTFTINNNITYLTPNVMSRVTIPIG
SFTGAFELTGSLTAYLNDKSLGSMELYKDLIKTLKVVNRFEIALVLGGEYDDERPAAILVAKQAH
VNIPTIETDDVLGTSVEFKAIPSDLDAGDEGYLGFSSKYTRTFINNLIVNGDGATDAVTAITVKS
AGNVTTLNRSATLQMSVEVTPSSARNKEVTWAITAGDAATINATGLLRADASKTGAVTVEATA
KDGSGVKGTKVITVTAGG ANC80 Malate Dehydrogenase (synthetic protein): SEQ ID No 7
MTKVSWGAAGIVGAAAGYNLALRDIADELVFVDIPDQEDVTIGQAADTNHGVAYDSNTIVR
QGGYEDTAGSDVVVITAGIPRQPGQTRIDLAGDNAPIMEDIGSSLAEHNDDFVTITTSNPVDL
LNRHLYETGDRAREKVIGFGGRLDSARFRYVLSQRFDAPVQNVEATILGEHGDAQVPVFSKVR
VDGTDPEFSADEKEEILGDLQESAMDVIERKGATQWGPATGVAHMVEAVLHDTGEVLPGSVV
LDGEFGHEDTAFGVPVKLGSNGVEEVVEWDLDDYEQDLMDDAAEKLSDQYDKIA

ANNEXE 2A

ANNEXE: 'QUIAGEN" plate

| Well | C | U | Salt | C | U | Buffer | pH | C | U | Precipitant | C | U | Additive |
|---|---|---|---|---|---|---|---|---|---|---|---|---|---|
| B09 |  | M | Ammonium phosphate | 0.1 | M | TRIS | 8.5 | 50 | % (v/v) | MPD |  |  |  |
| B05 | 0.2 | M | Ammonium acetate | 0.1 | M | tri-Sodium citrate | 5.6 | 30 | % (v/v) | MPD |  |  |  |
| B08 | 0.5 | M | Ammonium sulfate | 0.1 | M | HEPES | 7.5 | 30 | % (v/v) | MPD |  |  |  |
| B06 | 0.2 | M | Magnesium acetate | 0.1 | M | Sodium cocaylate | 6.5 | 10 | % (w/v) | MPD |  |  |  |
| G08 |  |  |  |  |  |  |  | 10 | % (w/v) | PEG 1000 | 10 | % (w/v) | PEG 8000 |
| H11 |  |  |  |  |  |  |  | 20 | % (w/v) | PEG | 8 | % (v/v) | Ethylene glycol |
| G09 |  |  |  |  |  | HEPES | 7.5 | 30 | % (w/v) | PEG 1500 |  |  |  |
| G11 | 0.2 | M | Ammonium sulfate | 0.1 | M | Sodium acetate | 4.6 | 30 | % (w/v) | PEG 2000 MME |  |  |  |
| G10 | 0.01 | M | Nickel chloride |  |  | TRIS | 8.5 | 20 | % (w/v) | PEG 2000 MME |  |  |  |
| H12 |  | M | Calcium chloride | 0.1 | M | MES | 6.5 | 12 | % (w/v) | PEG 20000 |  |  |  |
| G02 | 0.2 | M |  | 0.1 | M | HEPES sodium salt | 7.5 | 28 | % (w/v) | PEG 400 |  |  |  |
| G04 | 0.2 | M | Magnesium chloride | 0.1 | M | HEPES sodium salt | 7.5 | 30 | % (v/v) | PEG 400 |  |  |  |
| G05 | 0.2 | M | tri-Sodium citrate | 0.1 | M | TRIS HCL | 8.5 | 30 | % (v/v) | PEG 400 |  |  |  |
| G01 | 2 | % (v/v) | PEG 400 | 0.1 | M | HEPES sodium salt | 7.5 | 2 | M | Ammonium sulfate |  |  |  |
| G03 | 0.1 | M | Cadmium chloride | 0.1 | M | Sodium acetate | 4.6 | 30 | % (w/v) | PEG 400 |  |  |  |
| H02 | 0.2 | M | Ammonium sulfate | 0.1 | M | Sodium acetate | 4.6 | 30 | % (v/v) | PEG 4000 |  |  |  |
| H01 | 0.2 | M | Ammonium sulfate | 0.1 | M | Sodium acetate | 4.6 | 25 | M | PEG 4000 |  |  |  |
| H05 | 0.2 | M | Lithium sulfate | 0.1 | M | TRIS HCL | 8.5 | 30 | % (w/v) | PEG 4000 |  |  |  |
| H04 | 0.2 | M | Sodium acetate | 0.1 | M | TRIS HCL | 8.5 | 30 | % (w/v) | PEG 4000 |  |  |  |
| H03 | 0.2 | M | Ammonium acetate | 0.1 | M | tri-Sodium citrate | 5.6 | 30 | % (w/v) | PEG 4000 |  |  |  |
| H07 | 0.2 | M | Ammonium sulfate |  |  |  |  | 30 | % (w/v) | PEG 4000 |  |  |  |
| G12 |  |  | Magnesium chloride | 0.1 | M | Sodium acetate | 4.6 | 8 | % (w/v) | PEG 4000 |  |  |  |
| H08 | 0.2 | M | Ammonium sulfate | 0.1 | M | TRIS HCL | 8.5 | 30 | % (w/v) | PEG 4000 |  |  |  |
| G06 | 0.1 | M | Sodium chloride | 0.1 | M | MES | 6.5 | 30 | % (w/v) | PEG 4000 |  |  |  |
| G07 | 0.01 | M | Zinc sulfate | 0.1 | M | BICINE | 9 | 20 | M | PEG 5000 MME |  |  |  |
| H09 |  |  |  | 0.1 | M | MES | 6.5 | 25 | M | PEG 550 MME |  |  |  |
| H10 | 10 | (w/v) | PEG 6000 | 0.1 | M | HEPES | 7.5 | 10 | % (v/v) | PEG 6000 | 5 | % (v/v) | MPD |
| F04 |  |  |  |  |  |  |  | 2 | M | Sodium chloride |  |  |  |
| F06 | 0.2 | M | Zinc acetate | 0.1 | M | HEPES | 7.5 | 10 | % (w/v) | PEG 8000 |  |  |  |
| F10 | 0.2 | M | Ammonium sulfate | 0.1 | M | MES | 6.5 | 18 | % (w/v) | PEG 8000 |  |  |  |
| F07 | 0.2 | M | Calcium acetate | 0.1 | M | MES | 6.5 | 30 | % (w/v) | PEG 8000 |  |  |  |
| F08 | 0.2 | M | Magnesium acetate | 0.1 | M | MES | 6.5 | 18 | % (w/v) | PEG 8000 |  |  |  |
| F11 | 0.2 | M | Sodium acetate | 0.1 | M | MES | 6.5 | 20 | % (w/v) | PEG 8000 |  |  |  |
| F12 | 0.2 | M | Ammonium sulfate |  | M |  |  | 30 | % (w/v) | PEG 8000 |  |  |  |
| F05 | 0.5 | M | Lithium sulfate |  |  |  |  | 30 | % (w/v) | PEG 8000 |  |  |  |
| F09 | 0.05 | M | Potassium phosphate |  |  |  |  | 15 | % (w/v) | PEG 8000 |  |  |  |
| F03 |  |  |  | 0.1 | M | Tris HCl | 8.5 | 20 | % (w/v) | PEG 8000 |  |  |  |
| D03 |  |  |  | 0.1 | M | HEPES | 7.5 | 8 | M | Sodium acetate |  |  |  |
| D02 |  |  |  | 0.1 | M | Imidazole | 6.5 | 1 | M | Sodium acetate |  |  |  |
| D04 | 0.05 | M | Cadmium sulfate | 0.1 | M | MES | 6.5 | 1.4 | M | Sodium acetate |  |  |  |

-continued

ANNEXE 2A

| | | | | | | | | | |
|---|---|---|---|---|---|---|---|---|---|
| D07 | 0.1 | M | Sodium phosphate | 0.1 | M | HEPES | 7.5 | 4.3 | M | Sodium chloride |
| D06 | | | | 0.1 | M | MES | 6.5 | 2 | M | Sodium chloride |
| D05 | | | | 0.1 | M | Sodium acetate | 4.6 | 2 | M | Sodium chloride |
| D11 | | | | 0.1 | M | Sodium acetate | 4.6 | 2 | M | Sodium formate |
| D12 | | | | | | | | 4 | M | Sodium formate |
| D10 | 0.1 | M | HEPES sodium salt | | | | 7.5 | 0.8 | % (w/v) | Sodium phosphate |
| B11 | 0.1 | M | TRIS | | | | 8.5 | 25 | % (v/v) | tert-Butanol |
| B12 | 0.1 | M | tri-Sodium citrate | | | | 5.6 | 35 | % (v/v) | tert-Butanol |
| D08 | | | | 0.1 | M | HEPES sodium salt | 7.5 | 1.4 | M | tri-Sodium citrate |
| D09 | | | | | | | | 1.6 | M | tri-Sodium citrate pH6.5 |
| A03 | 0.2 | M | Magnesium chloride | 0.1 | M | TRIS | 8.5 | 3.4 | M | 1,6-Hexanediol |
| A02 | | | | 0.1 | M | Tri-Sodium citrate | 5.6 | 2.5 | M | 1,6-Hexanediol |
| A01 | 0.01 | M | Cobalt chloride | 0.1 | M | Sodium acetate | 4.6 | 1 | M | 1,6-Hexanediol |
| C04 | | | | 0.1 | M | HEPES | 7.5 | 2 | M | Ammonium formate |
| C03 | | | | 0.1 | M | TRIS HCL | 8.5 | 2 | M | Ammonium phosphate |
| C02 | | | | 0.1 | M | Tri-Sodium citrate | 5.6 | 1 | M | Ammonium phosphate |
| C01 | | | | | | | | 0.4 | M | Ammonium phosphate |
| C08 | 0.1 | M | Sodium chloride | 0.1 | M | HEPES | 7.5 | 1.6 | M | Ammonium sulfate |
| C09 | 0.01 | M | Cobalt chloride | 0.1 | M | MES | 6.5 | 1.8 | M | Ammonium sulfate |
| C05 | | | | 0.1 | M | Sodium acetate | 4.6 | 2 | M | Ammonium sulfate |
| C06 | | | | 0.1 | M | TRIS.HCL | 8.5 | 2 | M | Ammonium sulfate |
| C10 | 0.2 | M | K/Na tartrate | 0.1 | M | Tri-Sodium citrate | 5.6 | 2 | M | Ammonium sulfate |
| C07 | | | | | M | | | 0.01 | M | CTAB |
| E06 | 0.5 | M | Sodium chloride, | 0.1 | M | MES | 6.5 | 1.6 | M | Ammonium sulfate |
| E02 | 10 | % (v/v) | Dioxane, | | | | 9.0 | 35 | % (v/v) | Dioxane |
| E03 | 2 | % (v/v) | Dioxane, | | | | | 10 | % (w/v) | PEG 20000 |
| E01 | 10 | % (v/v) | ethanol | | | | | | M | Sodium chloride |
| A12 | | | | 0.1 | M | BICINE | 9.0 | 1.5 | % (v/v) | Ethanol |
| B01 | | | | 0.1 | M | TRIS | 8.5 | 20 | % (v/v) | Ethylene glycol |
| B02 | | | | | | | | 25 | | Ethylene imine polymer |
| E04 | 0.5 | M | Sodium chloride, | 0.1 | M | tri-Sodium citrate | 5.6 | 2 | M | Ammonium sulfate |
| E05 | 12 | (v/v) | Glycerol, | 0.1 | M | TRIS | 8.5 | 1.5 | M | |

| | | |
|---|---|---|
| D07 | 0.1 | Sodium phosphate |
| E06 | 0.01 | M Magnesium chloride |
| D10 | 0.1 | Potassium phosphate |
| B11 | 0.8 | M |

ANNEXE 2A -continued

| | | | | | | | | | |
|---|---|---|---|---|---|---|---|---|---|
| C11 | | | | | | 7.0 | 1 | M | Imidazole |
| A10 | 0.2 | M | Magnesium chloride | | | 7.5 | 30 | % (v/v) | Isopropanol |
| A08 | 0.2 | M | tri-Sodium citrate | | | 7.5 | 20 | % (v/v) | Isopropanol |
| A05 | 10 | % (v/v) | Isopropanol, | | | 7.5 | 20 | % (w/v) | PEG 9000 |
| A06 | 0.2 | M | Calcium chloride | 0.1 | M | Sodium acetate | 4.6 | 20 | % (v/v) | Isopropanol |
| A09 | 0.2 | M | tri-sodium citrate | 0.1 | M | MES | 6.5 | 30 | % (v/v) | Isopropanol |
| A11 | 0.2 | M | ammonium acetate | 0.1 | M | TRIS HCL | 8.5 | 30 | % (v/v) | Isopropanol |
| A07 | 20 | % (v/v) | isopropanol | 0.1 | M | Tri-sodium citrate | 5.6 | 20 | % (w/v) | PEG 4000 |
| A04 | 5 | % (v/v) | isopropanol | | | | 2 | M | Ammonium sulfate |
| E08 | | | | 0.1 | M | HEPES | 7.5 | 20 | % (v/v) | Jeffamine M-600 |
| E07 | 0.01 | M | ferric chloride | 0.1 | M | Tri_sodium citrate | 5.6 | 10 | % (v/v) | Jeffamine M-600 |
| D01 | | | | 0.1 | M | HEPES sodium salt | 7.5 | 0.8 | M | K/Na tartare |
| C12 | | | | | | | 0.4 | M | K/Na tartare |
| E11 | | | | 0.1 | M | HEPES sodium salt | 7.5 | 1.5 | M | Lithium sulfate |
| E10 | 0.01 | M | nickel chloride | 0.1 | M | TRIS | 8.5 | 1 | M | Lithium sulfate |
| E09 | 0.5 | M | | 0.1 | M | Tri-sodium citrate | 5.6 | 1 | M | Lithium sulfate |
| E12 | | | | 0.1 | M | BICINE | 9 | 2 | M | Magnesium chloride |
| F01 | | | | | | | 0.2 | M | Magnesium formate |
| F02 | | | | 0.1 | M | MES | 6.5 | 1.6 | M | Magnesium sulfate |
| B10 | | | | 0.1 | M | HEPES | 7.5 | 70 | % (v/v) | MPD |
| B07 | 0.2 | M | tri-sodium citrate | 0.1 | M | HEPES sodium salt | 7.5 | 30 | % (v/v) | MPD |
| B03 | 0.02 | M | clacium chloride | 0.1 | M | Sodium acetate | 4.6 | 30 | % (v/v) | MPD |
| B04 | 0.2 | M | sodium chloride | 0.1 | M | Sodium acetate | 4.6 | 30 | % (w/v) | MPD |

ANNEXE: "Hampton 2" plate

| | | | | | | | | | |
|---|---|---|---|---|---|---|---|---|---|
| A01 | 0.02 | M | calcium chloride dihydrate | 0.1 | M | Sodium acetate trihydrate | 4.6 | 15 | % (v/v) | MPD |
| A02 | 0.2 | M | ammonium acetate | 0.1 | M | Tri-Sodium citrate dihydrate | 5.6 | 15 | % (w/v) | PEG 4000 |
| A03 | 0.2 | M | lithium sulfate monohydrate | 0.1 | M | TRIS HCL | 8.5 | 15 | % (w/v) | PEG 4000 |
| A04 | | | | 0.1 | M | Imidazole | 6.5 | 0.5 | M | Sodium acetate trihydrate |
| A05 | | | | | | | 2 | M | Sodium formate |
| A06 | 5 | % (v/v) | iso-propanol | 0.1 | M | HEPES sodium salt | 7.5 | 10 | % (w/v) | PEG 4000 |
| A07 | 0.2 | M | sodium fluoride | | | | 7.1 | 20 | % (w/v) | PEG 3350 |
| A08 | 0.2 | M | ammonium chloride | | | | 6.3 | 20 | % (w/v) | PEG 3350 |

ANNEXE 2A -continued

| | | | | | | | | |
|---|---|---|---|---|---|---|---|---|
| A09 | 0.2 | M | sodium nitrate | | | 6.8 | 20 | % (w/v) | PEG 3350 |
| A10 | 0.2 | M | magnesium acetate tetrahydrate | | | 7.7 | 20 | % (w/v) | PEG 3350 |
| A11 | 0.2 | M | sodium sulfate decahydrate | | | 6.6 | 20 | % (w/v) | PEG 3350 |
| A12 | 0.2 | M | potassium dihydrogen phosphate | | | 4.7 | 20 | % (w/v) | PEG 3350 |
| B01 | | | | | | | 0.2 | M | Potassium/ sodium tartrate tetrahydrate |
| B02 | 0.2 | M | ammonium acetate | 0.1 | Sodium acetate trihydrate | 4.6 | 15 | % (w/v) | PEG 4000 |
| B03 | 0.2 | M | magnesium acetate tetrahydrate | 0.1 | Sodium cacodylate | 6.5 | 10 | % (w/v) | PEG 8000 |
| B04 | 0.2 | M | ammonium acetate | 0.1 | Tri-Sodium citrate dihydrate | 5.6 | 15 | % (v/v) | MPD |
| B05 | | | | 0.1 | Sodium acetate trihydrate | 4.6 | 1 | M | sodium formate |
| B06 | 0.05 | M | potassium dihydrogen phosphate | | | | 10 | % (w/v) | PEG 8000 |
| B07 | 0.2 | M | potassium fluoride | | | 7.2 | 20 | % (w/v) | PEG 3350 |
| B08 | 0.2 | M | sodium iodide | | | 6.9 | 20 | % (w/v) | PEG 3350 |
| B09 | 0.2 | M | potassium nitrate | | | 6.9 | 20 | % (w/v) | PEG 3350 |
| B10 | 0.2 | M | zinc acetate dihydrate | | | 6.3 | 20 | % (w/v) | PEG 3350 |
| B11 | 0.2 | M | potassium sulfate | | | 6.7 | 20 | % (w/v) | PEG 3350 |
| B12 | 0.2 | M | di-potassium hydrogen phosphate | | | 9.2 | 20 | % (w/v) | PEG 3350 |
| C01 | | | | | | | 0.2 | M | Ammonium dihydrogen phosphate |
| C02 | | | | 0.1 | Tri-Sodium citrate dihydrate | 5.6 | 0.5 | M | Ammonium dihydrogen phosphate |
| C03 | 0.2 | M | ammonium acetate | 0.1 | TRIS HCL | 8.5 | 15 | % (v/v) | Iso-propanol |
| C04 | 0.2 | M | tri-Sodium citrate dihydrate | 0.1 | HEPES sodium salt | 7.5 | 10 | % (v/v) | iso-propanol |
| C05 | | | | 0.1 | HEPES sodium salt | 7.5 | 0.4 | M | sodium dihydrogen phosphate |
| C06 | | | | | | | 15 | % (w/v) | PEG 1500 |
| C07 | 0.2 | M | ammonium fluoride | | | 6.2 | 20 | % (w/v) | PEG 3350 |
| C08 | 0.2 | M | potassium iodide | | | 6.8 | 20 | % (w/v) | PEG 3350 |
| C09 | 0.2 | M | ammonium nitrate | | | 6.3 | 20 | % (w/v) | PEG 3350 |
| C10 | 0.2 | M | sodium acetate trihydrate | | | 7.9 | 20 | % (w/v) | PEG 3350 |
| C11 | 0.2 | M | ammonium sulfate | | | 6 | 20 | % (w/v) | PEG 3350 | 0.4 | M | Potassium dihydrogen phosphate |

ANNEXE 2A -continued

| ID | | | | | | | pH | | | |
|---|---|---|---|---|---|---|---|---|---|---|
| C12 | 0.2 | M | ammonium dihydrogen phosphate | | | | 4.6 | 20 | % (w/v) | PEG 3350 |
| D01 | | | | | | | 8.5 | 1 | M | ammonium sulfate |
| D02 | 0.2 | M | magnesium chloride hexahydrate | 0.1 | M | TRIS HCL | 7.5 | 15 | % (v/v) | iso-propanol |
| D03 | 0.2 | M | ammonium sulfate | 0.1 | M | HEPES sodium salt | 4.6 | 12.5 | % (w/v) | PEG 4000 |
| D04 | 0.2 | M | sodium acetate trihydrate | 0.1 | M | Sodium acetate trihydrate | 6.5 | 15 | % (w/v) | PEG 8000 |
| D05 | | | | 0.1 | M | Sodium cacodylate | 8.5 | 4 | % (w/v) | PEG 8000 |
| D06 | | | | | | TRIS HCL | | 0.1 | M | magnesium formate |
| D07 | 0.2 | M | lithium chloride anhydrous | | | | 6.7 | 20 | % (w/v) | PEG 3350 |
| D08 | 0.2 | M | ammonium iodide | | | | 6.2 | 20 | % (w/v) | PEG 3350 |
| D09 | 0.2 | M | magnesium formate | | | | 5.9 | 20 | % (w/v) | PEG 3350 |
| D10 | 0.2 | M | calcium acetate hydrate | | | | 7.3 | 20 | % (w/v) | PEG 3350 |
| D11 | 0.2 | M | di-sodium tartrate dihydrate | | | | 7.2 | 20 | % (w/v) | PEG 3350 |
| D12 | 0.2 | M | di-ammonium hydrogen phosphate | | | | 7.9 | 20 | % (w/v) | PEG 3350 |
| E01 | 0.2 | M | tri-sodium citrate dihydrate | 0.1 | M | HEPES sodium salt | 7.5 | 15 | % (v/v) | MPD |
| E02 | 0.2 | M | tri-sodium citrate dihydrate | 0.1 | M | TRIS HCl | 8 | 15 | % (v/y) | PEG 400 |
| E03 | 0.2 | M | magnesium acetate tetrahydrate | 0.1 | M | sodium cacodylate | 6.5 | 15 | % (v/v) | MPD |
| E04 | | | | 0.1 | M | HEPES sodium salt | 7.5 | 0.4 | M | potassium/sodium tartrate tetrahydrate |
| E05 | | | | 0.1 | M | sodium acetate trihydrate | 4.6 | 4 | % (w/v) | PEG 4000 |
| E06 | 0.2 | M | zinc acetate dihydrate | 0.1 | M | sodium cacodylate | 6.5 | 9 | % (w/v) | PEG 8000 |
| E07 | 0.2 | M | magnesium chloride hexahydrate | | | | 5.8 | 20 | % (w/v) | PEG 3350 |
| E08 | 0.2 | M | sodium thiocyanate | | | | 6.9 | 20 | % (w/v) | PEG 3350 |
| E09 | 0.2 | M | sodium formate | | | | 7.2 | 20 | % (w/v) | PEG 3350 |
| E10 | 0.2 | M | potassium acetate | | | | 7.8 | 20 | % (w/v) | PEG 3350 |
| E11 | 0.2 | M | potassium sodium tartrate tetrahydrate | | | | 7.2 | 20 | % (w/v) | PEG 3350 |
| E12 | 0.2 | M | tri-lithium citrate tetrahydrate | | | | 8.1 | 20 | % (w/v) | PEG 3350 |
| F01 | 0.2 | M | magnesium chloride hexahydrate | 0.1 | M | TRIS HCl | 8.5 | 15 | % (w/v) | PEG 4000 |
| F02 | 0.2 | M | calcium chloride dihydrate | 0.1 | M | HEPES sodium salt | 7.5 | 14 | % (v/v) | PEG 400 |

-continued

ANNEXE 2A

| | | | | | | | | |
|---|---|---|---|---|---|---|---|---|
| F03 | 0.2 | M | sodium acetate trihydrate | 0.1 | M | TRIS HCl | 8.5 | 15 | % (w/v) | PEG 4000 |
| F04 | 0.2 | M | ammonium sulfate | | | | 7.5 | 15 | % (w/v) | PEG 8000 |
| F05 | | | | 0.1 | M | HEPES sodium salt | 7.5 | 0.7 | M | tri-sodium citrate dihydrate |
| F06 | 0.2 | M | calcium acetate hydrate | 0.1 | M | Sodium cacodylate | 6.5 | 9 | % (w/v) | PEG 8000 |
| F07 | 0.2 | M | sodium chloride | | | | 6.9 | 20 | % (w/v) | PEG 3350 |
| F08 | 0.2 | M | potassium thiocyanate | | | | 7 | 20 | % (w/v) | PEG 3350 |
| F09 | 0.2 | M | potassium formate | | | | 7.3 | 20 | % (w/v) | PEG 3350 |
| F10 | 0.2 | M | ammonium acetate | | | | 7.1 | 20 | % (w/v) | PEG 3350 |
| F11 | 0.2 | M | di-ammonium tartrate | | | | 6.6 | 20 | % (w/v) | PEG 3350 |
| F12 | 0.2 | M | tri-sodium citrate dihydrate | | | | 8.2 | 20 | % (w/v) | PEG 3350 |
| G01 | | | | 0.1 | M | Sodium cacodylate | 6.5 | 0.7 | M | sodium acetate trihydrate |
| G02 | 0.2 | M | ammonium sulfate | 0.1 | N | Sodium cacodylate | 6.5 | 15 | % (w/v) | PEG 8000 |
| G03 | 0.2 | M | magnesium chloride hexahydrate | 0.1 | M | HEPES sodium salt | 7.5 | 15 | % (v/v) | PEG 400 |
| G04 | 0.2 | M | ammonium sulfate | 0.1 | M | HEPES sodium salt | 7.5 | 15 | % (w/v) | PEG 4000 |
| G05 | 2 | % (v/v) | PEG 400 | | | | | 1 | M | Ammonium sulfate |
| G06 | | | | 0.1 | M | Sodium acetate trihydrate | 4.6 | 1 | M | Ammonium sulfate |
| G07 | 0.2 | M | Calcium chloride dihydrate | | | | 5.1 | 20 | % (w/v) | PEG 3350 |
| G08 | 0.2 | M | Lithium nitrate | | | | 7.1 | 20 | % (w/v) | PEG 3350 |
| G09 | 0.2 | M | Ammonium formate | | | | 6.6 | 20 | % (w/v) | PEG 3350 |
| G10 | 0.2 | M | Lithium sulfate monohydrate | | | | 5.4 | 20 | % (w/v) | PEG 3350 |
| G11 | 0.2 | M | Sodium dihydrogen phosphate monohydrate | | | | 4.5 | 20 | % (w/v) | PEG 3350 |
| G12 | 0.2 | M | Tri-potassium citrate monohydrate | | | | 8.3 | 20 | % (w/v) | PEG 3350 |
| H01 | 0.2 | M | Tri-sodium citrate dihydrate | | | | 6.5 | 15 | % (v/v) | iso-propanol |
| H02 | | | | 0.1 | M | HEPES sodium salt | 7.5 | 0.75 | M | lithium sulfate monohydrate |
| H03 | 0.2 | M | Calcium chloride dihydrate | 0.1 | M | Sodium acetate trihydrate | 4.6 | 10 | % (v/v) | iso-propanol |
| H04 | | | | | | | | 1 | M | ammonium sulfate |
| H05 | 10 | % (v/v) | Iso-propanol | 0.1 | M | Tri-sodium citrate dihydrate | 5.6 | 10 | % (w/v) | PEG 4000 |
| H06 | | | | 0.1 | M | TRIS HCl | 8.5 | 1 | M | Ammonium dihydrogen phosphate |

-continued

ANNEXE 2A

| | | | | | | | | | |
|---|---|---|---|---|---|---|---|---|---|
| H07 | 0.2 | M | Potassium chloride | | | 6.9 | 20 | % (w/v) | PEG 3350 |
| H08 | 0.2 | M | Magnesium nitrate hexahydrate | | | 5.8 | 20 | % (w/v) | PEG 3350 |
| H09 | 0.2 | M | Lithium acetate dihydrate | | | 7.8 | 20 | % (w/v) | PEG 3350 |
| H10 | 0.2 | M | Magnesium sulfate heptahydrate | | | 5.9 | 20 | % (w/v) | PEG 3350 |
| H11 | 0.2 | M | Di-sodium hydrogen phosphate dihydrate | | | 9.1 | 20 | % (w/v) | PEG 3350 |
| H12 | 0.2 | M | Di-ammonium hydrogen citrate | | | 5 | 20 | % (w/v) | PEG 3350 |

ANNEXE: 'Hampton 3" plate

| | | | | | | | | | | | |
|---|---|---|---|---|---|---|---|---|---|---|---|
| A01 | 0.1 | M | Sodium chloride | 0.1 | M | Sodium acetate trihydrate | 4.6 | 12 | % (v/v) | MPD | |
| A02 | 0.1 | M | Lithium sulfate monohydrate | 0.1 | M | Sodium acetate trihydrate | 4.6 | 1 | M | ammonium dihydrogen phosphate | |
| A03 | 0.1 | M | Sodium chloride | 0.1 | M | Tri-sodium citrate dihydrate | 5.6 | 12 | % (w/v) | PEG 4000 | |
| A04 | 0.1 | M | Magnesium chloride hexahydrate | 0.1 | M | ADA | 6.5 | 12 | % (w/v) | PEG 6000 | |
| A05 | 0.1 | M | Ammonium sulfate | 0.1 | M | HEPES sodium salt | 7.5 | 18 | % (v/v) | PEG 400 | |
| A06 | 0.1 | M | Di-ammonium hydrogen phosphate | 0.1 | M | TRIS HCl | 8.5 | 0.5 | M | di-sodium hydrogen phosphate | 0.5 M Di-potassium hydrogen phosphate |
| A07 | 0.05 | M | Magnesium chloride hexahydrate | 0.05 | M | MES | 5.6 | 2 | M | lithium sulfate monohydrate | |
| A08 | 0.05 | M | Potassium chloride | 0.05 | M | MES | 6 | 10 | % (v/v) | PEG 400 | 0.01 M Magnesium chloride hexahydrate |
| A09 | 0.05 | M | Potassium chloride | 0.05 | M | Sodium cacodylate | 6 | 1 | % (w/v) | PEG 4000 | 0.01 M Calcium chloride dihydrate |
| A10 | 0.2 | M | Magnesium acetate tetrahydrate | 0.05 | M | Sodium cacodylate | 6.5 | 30 | % (v/v) | PEG 400 | 0 |
| A11 | 0.08 | M | Ammonium chloride | 0.05 | M | HEPES sodium salt | 7 | 30% | % (w/v) | 1,6-hexanediol | 0.01 M Magnesium chloride hexahydrate |
| A12 | 0.2 | M | Potassium chloride | 0.05 | M | TRIS HCl | 7.5 | 10 | % (v/v) | PEG monomethyl ether 550 | 0.015 M Magnesium chloride hexahydrate |
| B01 | 0.1 | M | Zinc acetate dihydrate | 0.1 | M | Sodium acetate trihydrate | 4.6 | 12 | % (w/v) | PEG 4000 | |
| B02 | 0.1 | M | Sodium chloride | 0.1 | M | Sodium acetate trihydrate | 4.6 | 12 | % (w/v) | PEG 6000 | |
| B03 | 0.1 | M | Lithium sulfate monohydrate | 0.1 | M | Tri-sodium citrate dihydrate | 5.6 | 12 | % (w/v) | PEG 6000 | |
| B04 | 0.1 | M | | 0.1 | M | ADA | 6.5 | 12 | % (v/v) | MPD | |
| B05 | 0.1 | M | Ammonium sulfate | 0.1 | M | HEPES sodium salt | 7.5 | 10 | % (w/v) | PEG 4000 | |
| B06 | | | | 0.1 | M | TRIS HCl | 8.5 | 0.1 | M | sodium acetate trihydrate | |
| B07 | 0.01 | M | Magnesium acetate | 0.05 | M | MES | 5.6 | 2.5 | M | ammonium | |

-continued

ANNEXE 2A

| ID | | | | pH | | | | | | |
|---|---|---|---|---|---|---|---|---|---|---|
| B08 | 0.005 | M | Magnesium sulfate tetrahydrate | 6 | 5 | % (w/v) | PEG 4000 | 0 | | |
| B09 | 0.01 | M | Magnesium acetate tetrahydrate | 6.5 | 1.3 | M | lithium sulfate monohydrate | 0 | | |
| B10 | 0.2 | M | Potassium chloride | 6.5 | 10 | % (w/v) | PEG 8000 | 0.1 | M | Magnesium acetate tetrahydrate |
| B11 | 0.1 | M | Potassium chloride | 7 | 15 | % (v/v) | MPD | 0.005 | M | Magnesium sulfate aq. |
| B12 | 0.01 | M | Magnesium acetate tetrahydrate | 7.5 | 5 | % (v/v) | iso-propanol | 0 | | |
| C01 | 0.2 | M | Ammonium sulfate | 4.6 | 10 | % (w/v) | PEG 4000 | | | |
| C02 | 0.1 | M | Magnesium chloride hexahydrate | 4.6 | 12 | % (w/v) | PEG 600 | | | |
| C03 | 0.1 | M | Magnesium chloride hexahydrate | 5.6 | 4 | % (v/v) | MPD | | | |
| C04 | 0.1 | M | Lithium sulfate monohydrate | 6.5 | 1 | M | magnesium sulfate hydrate | | | |
| C05 | 0.1 | M | tri-sodium citrate dihydrate | 7.5 | 12 | % (v/v) | MPD | 0 | | |
| C06 | 0 | | 0 | 8.5 | 0.1 | M | sodium chloride | 0 | | |
| C07 | 0.1 | M | magnesium acetate tetrahydrate | 5.6 | 20 | % (v/v) | MPD | | | |
| C08 | 0.01 | M | magnesium chloride hexahydrate | 6 | 1 | M | lithium sulfate monohydrate | | | |
| C19 | 0.01 | M | magnesium sulfate hexahydrate | 6.5 | 2 | M | ammonium sulfate | | | |
| C10 | 0.2 | M | ammonium acetate | 6.5 | 30 | % (w/v) | PEG 8000 | 0.01 | M | magnesium acetate tetrahydrate |
| C11 | 0.1 | M | potassium chloride | 7 | 5 | % (v/v) | PEG 400 | 0.01 | M | magnesium chloride hexahydrate |
| C12 | 0.05 | M | ammonium acetate | 7.5 | 10 | % (v/v) | MPD | 0.01 | M | magnesium chloride hexahydrate |
| D01 | 0.1 | M | sodium chloride | 4.6 | 12 | % (v/v) | iso-propanol | | | |
| D02 | 0.1 | M | sodium chloride | 5.6 | 18 | % (w/v) | PEG 400 | | | |
| D03 | 0.1 | M | 0 | 5.6 | 0.1 | M | sodium chloride | | | |
| D04 | 0.3 | M | lithium sulfate monohydrate | 6.5 | 4 | % (w/v) | PEG 400 | | | |
| D05 | 0 | | 0 | 7.5 | 1 | M | tri-sodium citrate dihydrate | | | |
| D06 | 0.1 | M | di-ammonium hydrogen phosphate | 8.5 | 12 | % (w/v) | PEG 6000 | | | |
| D07 | 0.2 | M | potassium chloride | 5.6 | 10 | % (v/v) | PEG 400 | 0.01 | M | magnesium sulfate |
| D08 | 0.01 | M | magnesium sulfate | 6 | 1.8 | M | lithium sulfate monohydrate | 0 | | |
| D09 | 0.1 | M | ammonium acetate | 6.5 | 10 | % (v/v) | iso-propanol | 0.015 | M | magnesium acetate tetrahydrate |

-continued

ANNEXE 2A

| ID | | | | | | | pH | | | | | | |
|---|---|---|---|---|---|---|---|---|---|---|---|---|---|
| D10 | 0.05 | M | Magnesium sulfate aq. | 0.05 | M | HEPES sodium salt | 7 | 1.6 | M | Lithium sulfate monohydrate | 0 | | 0 |
| D11 | 0.1 | M | Potassium chloride | 0.05 | M | HEPES sodium salt | 7 | 10 | % (w/v) | PEG 400 | 0.01 | M | Calcium chloride dihydrate |
| D12 | 0.2 | M | Potassium chloride | 0.05 | M | TRIS HCl | 7.5 | 10 | % (w/v) | PEG 4000 | 0.05 | M | Magnesium chloride hexahydrate |
| E01 | 0 | | 0 | 0.1 | M | sodium acetate trihydrate | 4.6 | 12 | % (w/v) | PEG 9000 | | | |
| E02 | 0.1 | M | Lithium sulfate monohydrate | 0.1 | M | tri-sodium citrate dihydrate | 5.6 | 12 | % (v/v) | PEG 4000 | | | |
| E03 | 0.1 | M | Lithium sulfate monohydrate | 0.1 | M | tri-sodium citrate dihydrate | 5.6 | 4 | % (v/v) | PEG 400 | | | |
| E04 | 0.1 | M | Ammonium sulfate | 0.1 | M | HEPES sodium salt | 7.5 | 0.5 | M | DI-SODIUM HYDROGEN PHOSPHATE | 0.5 | M | Di-potassium hydrogen phosphate |
| E05 | 0.6 | M | Magnesium sulfate hydrate | 0.1 | M | HEPES sodium salt | 7.5 | 9 | % (v/v) | PEG 400 | | | |
| E06 | 0.1 | M | Potassium/sodium tartrate tetrahydrate | 0.1 | M | TRIS HCl | 8.5 | 0.4 | M | Magnesium sulfate hydrate | | | |
| E07 | 0.2 | M | Potassium chloride | 0.05 | M | MES | 5.6 | 5 | % (w/v) | Peg 8000 | 0.01 | M | Magnesium chloride hexahydrate |
| E08 | 0.015 | M | Magnesium acetate tetrahydrate | 0.05 | M | Sodium cacodylate | 6 | 1.7 | M | Ammonium sulfate | 0 | | 0 |
| E09 | 0.2 | M | Potassium chloride | 0.05 | M | Sodium cacodylate | 6.5 | 10 | % (v/v) | 1,6-hexanediol | 0.005 | M | Magnesium chloride hexahydrate |
| E10 | 0.01 | M | Magnesium chloride hexahydrate | 0.05 | M | HEPES sodium salt | 7 | 4 | M | Lithium chloride | 0 | | 0 |
| E11 | 0.2 | M | Potassium chloride | 0.05 | M | HEPES sodium salt | 7 | 20 | % (v/v) | PEG 200 | 0.025 | M | Magnesium sulfate aq. |
| E12 | 0.025 | M | Magnesium sulfate aq. | 0.05 | M | TRIS HCl | 8.5 | 1.8 | M | Ammonium sulfate | 0 | | 0 |
| F01 | 0 | | 0 | 0.1 | M | Sodium acetate trihydrate | 4.6 | 1 | M | Ammonium sulfate | | | |
| F02 | 0.1 | M | Tri-sodium citrate dihydrate | 0.1 | M | Tri-sodium citrate dihydrate | 5.6 | 10 | % (v/v) | Iso-propanol | | | |
| F03 | 0 | | 0 | 0.1 | M | ADA | 6.5 | 1 | M | Ammonium sulfate | | | |
| F04 | 0.1 | M | Sodium chloride | 0.1 | M | HEPES sodium salt | 7.5 | 10 | % (w/v) | PEG 4000 | | | |
| F05 | 0.6 | M | Magnesium sulfate hydrate | 0.1 | M | HEPES sodium salt | 7.5 | 4 | % (v/v) | MPD | | | |
| F06 | 0 | | 0 | 0.1 | M | TRIS HCl | 8.5 | 0.2 | M | Lithium sulfate monohydrate | | | |
| F07 | 0.1 | M | Ammonium sulfate | 0.05 | M | MES | 5.6 | 20 | % (w/v) | PEG 8000 | 0.01 | M | Magnesium chloride hexahydrate |
| F08 | 0.1 | M | Potassium chloride | 0.05 | M | Sodium cacodylate | 6 | 15 | % (v/v) | Iso-propanol | 0.025 | M | Magnesium chloride hexahydrate |
| F09 | 0.08 | M | Magnesium acetate tetrahydrate | 0.05 | M | Sodium cacodylate | 6.5 | 15 | % (v/v) | PEG 400 | 0 | | 0 |
| F10 | 0.01 | M | Magnesium chloride hexahydrate | 0.05 | M | HEPES sodium salt | 7 | 1.6 | M | Ammonium sulfate | 0 | | 0 |

ANNEXE 2A -continued

| ID | Conc | Unit | Salt | Conc | Unit | Buffer | pH | Conc | Unit | Precipitant | Conc | Unit | Additive |
|---|---|---|---|---|---|---|---|---|---|---|---|---|---|
| F11 | 0.2 | M | Ammonium acetate | 0.05 | M | HEPES sodium salt | 7 | 5 | % (w/v) | PEG 4000 | 0.15 | M | Magnesium acetate tetrahydrate 0 |
| F12 | 0.005 | M | Magnesium sulfate aq. 0 | 0.05 | M | TRIS HCl | 8.5 | 35 | % (w/w) | 1,6-hexanediol | 0 | | |
| G01 | 0 | | | 0.1 | M | Sodium acetate trihydrate | 4.6 | 1 | M | Magnesium sulfate heptahydrate | | | |
| G02 | 0.1 | M | Sodium chloride | 0.1 | M | Tri-sodium citrate dihydrate | 5.6 | 12 | % (v/v) | MPD | | | |
| G03 | 0.1 | M | Lithium sulfate monohydrate | 0.1 | M | ADA | 6.5 | 12 | % (w/v) | PEG 4000 | 2 | % (v/v) | Iso-propanol |
| G04 | 0.1 | M | Magnesium chloride hexahydrate | 0.1 | M | HEPES sodium salt | 7.5 | 18 | % (v/v) | PEG 400 | | | |
| G05 | 0.1 | M | Lithium sulfate monohydrate | 0.1 | M | HEPES sodium salt | 7.5 | 0.1 | M | Potassium/sodium tartrate tetrahydrate | | | |
| G06 | 0 | | 0 | 0.1 | M | TRIS HCl | 8.5 | 0.5 | M | Ammonium sulfate | | | |
| G07 | 0.02 | M | Magnesium chloride hexahydrate | 0.05 | M | MES | 6 | 15 | % (v/v) | iso-propanol | 0 | | 0 |
| G08 | 0.04 | 14 | Magnesium chloride hexahydrate | 0.05 | M | Sodium cacodylate | 6 | 5 | % (v/v) | MPD | 0 | | 0 |
| G09 | 0.2 | M | Potassium chloride | 0.05 | M | Sodium cacodylate | 6.5 | 10 | % (w/v) | PEG 4000 | 0.01 | M | Magnesium chloride hexahydrate |
| G10 | 0.005 | M | Magnesium chloride hexahydrate | 0.05 | M | HEPES sodium salt | 7 | 25 | % (v/v) | PEG monomethyl ether 550 | 0 | | 0 |
| G11 | 0.1 | M | Ammonium acetate | 0.05 | M | HEPES sodium salt | 7 | 5 | % (w/v) | PEG 8000 | 0.02 | M | Magnesium chloride hexahydrate |
| G12 | 0.1 | M | Potassium chloride | 0.05 | M | TRIS HCl | 8.5 | 30 | % (v/v) | PEG 400 | 0.01 | M | Magnesium chloride hexahydrate |
| H01 | 0.1 | M | Magnesium chloride hexahydrate | 0.1 | M | Sodium acetate trihydrate | 4.6 | 18 | % (v/v) | PEG 400 | | | |
| H02 | 0 | | 0 | 0.1 | M | Tri-sodium citrate dihydrate | 5.6 | 1 | M | Magnesium sulfate heptahydrate Di-ammonium hydrogen phosphate | | | |
| H03 | 0 | | | 0.1 | M | ADA | 6.5 | 1 | M | Potassium/sodium tartrate tetrahydrate | | | |
| H04 | 0 | | 0 | 0.1 | M | HEPES sodium salt | 7.5 | 1 | M | MPD | | | |
| H05 | 0.1 | M | Lithium sulfate monohydrate | 0.1 | M | TRIS HCl | 8.5 | 12 | % (v/v) | PEG 400 | | | |
| H06 | 0.1 | M | Tri-sodium citrate dihydrate | 0.1 | M | TRIS HCl | 8.5 | 5 | % (v/v) | MPD | | | |
| H07 | 0.1 | M | Ammonium acetate | 0.05 | M | MES | 6 | 0.6 | M | Sodium chloride | 0.005 | M | Magnesium sulfate |
| H08 | 0.04 | M | Magnesium acetate tetrahydrate | 0.05 | M | Sodium cacodylate | 6 | 30 | % (v/v) | MPD | 0 | | 0 |
| H09 | 0.2 | M | Ammonium acetate | 0.05 | M | Sodium cacodylate | 6.5 | 10 | % (w/v) | PEG 4000 | 0.01 | M | Calcium chloride dihydrate |
| H10 | 0.2 | M | Potassium chloride | 0.05 | M | HEPES sodium salt | 7 | 20% | % (w/v) | 1,6-hexanediol | 0.01 | M | Magnesium chloride hexahydrate |

-continued

ANNEXE 2A

| | C | U | | C | U | | | pH | C | % (w/v) | M | | | | |
|---|---|---|---|---|---|---|---|---|---|---|---|---|---|---|---|
| H11 | 0.01 | M | Magnesium chloride hexahydrate | 0.05 | M | | | 7.5 | 1.6 | | M | Ammonium sulfate PEG 4000 | 0 | 0.01 | M | 0 | Calcium chloride dihydrate |
| H12 | 0.2 | M | Ammonium chloride | 0.05 | M | TRIS HCl | | 8.5 | 30 | % (w/v) | | | | | |

ANNEXE: 'Hampton 4" plate

| Well | Buffer | C | U | pH | C | U | Precipitant |
|---|---|---|---|---|---|---|---|
| A01 | CITRIC ACID | 0.1 | M | 4 | 0.8 | M | Ammonium sulfate |
| A02 | CITRIC ACID | 0.1 | M | 5 | 0.8 | M | Ammonium sulfate |
| A03 | MES | 0.1 | M | 6 | 0.8 | M | Ammonium sulfate |
| A04 | HEPES | 0.1 | M | 7 | 0.8 | M | Ammonium sulfate |
| A05 | TRIS | 0.1 | M | 8 | 0.8 | M | Ammonium sulfate |
| A06 | NONE | 0.1 | M | 9 | 0.8 | M | Ammonium sulfate |
| B01 | CITRIC ACID | 0.1 | M | 4 | 1.6 | M | Ammonium sulfate |
| B02 | CITRIC ACID | 0.1 | M | 5 | 1.6 | M | Ammonium sulfate |
| B03 | MES | 0.1 | M | 6 | 1.6 | M | Ammonium sulfate |
| B04 | HEPES | 0.1 | M | 7 | 1.6 | M | Ammonium sulfate |
| B05 | TRIS | 0.1 | M | 8 | 1.6 | M | Ammonium sulfate |
| B06 | BICINE | 0.1 | M | 9 | 1.6 | M | Ammonium sulfate |
| C01 | CITRIC ACID | 0.1 | M | 4 | 2.4 | M | Ammonium sulfate |
| C02 | CITRIC ACID | 0.1 | M | 5 | 2.4 | M | Ammonium sulfate |
| C03 | MES | 0.1 | M | 6 | 2.4 | M | Ammonium sulfate |
| C04 | HEPES | 0.1 | M | 7 | 2.4 | M | Ammonium sulfate |
| C05 | TRIS | 0.1 | M | 8 | 2.4 | M | Ammonium sulfate |
| C06 | BICINE | 0.1 | M | 9 | 2.4 | M | Ammonium sulfate |
| D01 | CITRIC ACID | 0.1 | M | 4 | 3 | M | Ammonium sulfate |
| D02 | CITRIC ACID | 0.1 | M | 5 | 3 | M | Ammonium sulfate |
| D03 | MES | 0.1 | M | 6 | 3 | M | Ammonium sulfate |

-continued

ANNEXE 2A

| Well | C | U | Buffer | pH | C | U | Precipitant | C | U | Additive |
|---|---|---|---|---|---|---|---|---|---|---|
| D04 | 0.1 | M | HEPES | 7 | 3 | M | Ammonium sulfate | | | |
| D05 | 0.1 | M | TRIS | 8 | 3 | M | Ammonium sulfate | | | |
| D06 | 0.1 | M | BICINE | 9 | 3 | M | Ammonium sulfate | | | |
| E01 | | | | 4 | 1 | M | Malonate | | | |
| E02 | | | | 4 | 1.5 | M | Malonate | | | |
| E03 | | | | 4 | 1.9 | M | Malonate | | | |
| E04 | | | | 4 | 2.4 | M | Malonate | | | |
| E05 | | | | 4 | 2.9 | M | Malonate | | | |
| E06 | | | | 4 | 3.4 | M | Malonate | | | |
| F01 | | | | 5 | 1 | M | Malonate | | | |
| F02 | | | | 5 | 1.5 | M | Malonate | | | |
| F03 | | | | 5 | 1.9 | M | Malonate | | | |
| F04 | | | | 5 | 2.4 | M | MALONATE | | | |
| F05 | | | | 5 | 2.9 | M | MALONATE | | | |
| F06 | | | | 5 | 3.4 | M | MALONATE | | | |
| G01 | | | | 6 | 1 | M | MALONATE | | | |
| G02 | | | | 6 | 1.5 | M | MALONATE | | | |
| G03 | | | | 6 | 1.9 | M | MALONATE | | | |
| G04 | | | | 6 | 2.4 | M | MALONATE | | | |
| G05 | | | | 6 | 2.9 | M | MALONATE | | | |
| G06 | | | | 6 | 3.4 | M | MALONATE | | | |
| H01 | | | | 7 | 1 | M | MALONATE | | | |
| H02 | | | | 7 | 1.5 | M | MALONATE | | | |
| H03 | | | | 7 | 1.9 | M | MALONATE | | | |
| H04 | | | | 7 | 2.4 | M | malonate | | | |
| H05 | | | | 7 | 2.9 | M | malonate | | | |
| H06 | | | | 7 | 3.4 | M | malonate | | | |
| A07 | 0.8 | M | Sodium/potassium phosphate | 5 | 0.78 | M | Sodium dihydrogen phosphate monohydrate | 0.016 | M | Di-potassium hydrogen phosphate |
| A08 | 0.8 | M | Sodium/potassium phosphate | 5.6 | 0.72 | M | Sodium dihydrogen phosphate monohydrate | 0.08 | M | Di-potassium hydrogen phosphate |
| A09 | 0.8 | M | Sodium/potassium phosphate | 6.3 | 0.52 | M | Sodium dihydrogen phosphate monohydrate | 0.28 | M | Di-potassium hydrogen phosphate |
| A10 | 0.8 | M | Sodium/potassium phosphate | 6.9 | 0.28 | M | Sodium dihydrogen phosphate monohydrate | 0.52 | M | Di-potassium hydrogen phosphate |
| A11 | 0.8 | M | Sodium/potassium phosphate | 7.5 | 0.12 | M | Sodium dihydrogen | 0.68 | M | Di-potassium hydrogen |

ANNEXE 2A -continued

| | | | | | | | | |
|---|---|---|---|---|---|---|---|---|
| | | | | | | | | phosphate monohydrate |
| A12 | 0.8 | M | Sodium/potassium phosphate | 8.2 | 0.032 | M | Sodium dihydrogen phosphate monohydrate | 0.768 | M | Di-potassium hydrogen phosphate |
| B07 | 1 | M | Sodium/Potassium phosphate | 5 | 0.98 | M | Sodium dihydrogen phosphate monohydrate | 0.02 | M | Di-potassium hydrogen phosphate |
| B08 | 1 | M | Sodium/potassium phosphate | 5.6 | 0.9 | M | Sodium dihydrogen phosphate monohydrate | 0.1 | M | Di-potassium hydrogen phosphate |
| B09 | 1 | M | Sodium/potassium phosphate | 6.3 | 0.65 | M | Sodium dihydrogen phosphate monohydrate | 0.35 | M | Di-potassium hydrogen phosphate |
| B10 | 1 | M | Sodium/potassium phosphate | 6.9 | 0.35 | M | Sodium dihydrogen phosphate monohydrate | 0.65 | M | Di-potassium hydrogen phosphate |
| B11 | 1 | M | Sodium/potassium phosphate | 7.5 | 0.15 | M | Sodium dihydrogen phosphate monohydrate | 0.85 | M | Di-potassium hydrogen phosphate |
| B12 | 1 | M | Sodium/potassium phosphate | 8.2 | 0.04 | M | Sodium dihydrogen phosphate monohydrate | 0.96 | M | Di-potassium hydrogen phosphate |
| C07 | 1.4 | M | Sodium/potassium phosphate | 5 | 1.372 | M | Sodium dihydrogen phosphate monohydrate | 0.028 | M | Di-potassium hydrogen phosphate |
| C08 | 1.4 | M | Sodium/potassium phosphate | 5.6 | 1.26 | M | Sodium dihydrogen phosphate monohydrate | 0.19 | M | Di-potassium hydrogen phosphate |
| C09 | 1.4 | M | Sodium/potassium phosphate | 6.3 | 0.91 | M | Sodium dihydrogen phosphate monohydrate | 0.49 | M | Di-potassium hydrogen phosphate |
| C10 | 1.4 | M | Sodium/potassium phosphate | 6.9 | 0.99 | M | Sodium dihydrogen phosphate monohydrate | 0.91 | M | Di-potassium hydrogen phosphate |
| C11 | 1.4 | M | Sodium/potassium phosphate | 7.5 | 0.21 | M | Sodium dihydrogen phosphate monohydrate | 1.19 | M | Di-potassium hydrogen phosphate |

-continued

ANNEXE 2A

| ID | | | | | | | | | | |
|---|---|---|---|---|---|---|---|---|---|---|
| C12 | 1.4 | M | Sodium/potassium phosphate | 8.2 | 0.056 | M | Sodium dihydrogen phosphate monohydrate | 1.344 | M | Di-potassium hydrogen phosphate |
| D07 | 1.8 | M | Sodium/potassium phosphate | 5 | 1.764 | M | Sodium dihydrogen phosphate monohydrate | 0.036 | M | Di-potassium hydrogen phosphate |
| D08 | 1.8 | M | Sodium/potassium phosphate | 5.6 | 1.62 | M | Sodium dihydrogen phosphate monohydrate | 0.18 | M | Di-potassium hydrogen phosphate |
| D09 | 1.8 | M | Sodium/potassium phosphate | 6.3 | 1.17 | M | Sodium dihydrogen phosphate monohydrate | 0.63 | M | Di-potassium hydrogen phosphate |
| D10 | 1.8 | M | Sodium/potassium phosphate | 6.9 | 0.63 | M | Sodium dihydrogen phosphate monohydrate | 1.17 | M | Di-potassium hydrogen phosphate |
| D11 | 1.8 | M | Sodium/potassium phosphate | 7.5 | 0.27 | M | Sodium dihydrogen phosphate monohydrate | 1.53 | M | Di-potassium hydrogen phosphate |
| D12 | 1.8 | M | Sodium/potassium phosphate | 8.2 | 0.072 | M | Sodium dihydrogen phosphate monohydrate | 1.728 | M | Di-potassium hydrogen phosphate |
| E07 | 0.1 | M | CITRIC ACID | 4 | 0.8 | M | Sodium formate ph4 | | | |
| E08 | 0.1 | M | CITRIC ACID | 5 | 0.8 | M | Sodium formate ph5 | | | |
| E09 | 0.1 | M | MES | 6 | 0.8 | M | Sodium formate ph6 | | | |
| E10 | 0.1 | M | HEPES | 7 | 0.8 | M | Sodium formate ph7 | | | |
| E11 | 0.1 | M | TRIS | 8 | 0.8 | M | Sodium formate ph8 | | | |
| E12 | 0.1 | M | BICINE | 9 | 0.8 | M | Sodium formate ph9 | | | |
| F07 | 0.1 | M | CITRIC ACID | 4 | 1.6 | M | Sodium formate ph4 | | | |
| E08 | 0.1 | M | CITRIC ACID | 5 | 1.6 | M | Sodium formate ph5 | | | |
| F09 | 0.1 | M | MES | 6 | 1.6 | M | Sodium formate ph6 | | | |
| F10 | 0.1 | M | HEPES | 7 | 1.6 | Fl | Sodium formate ph7 | | | |
| F11 | 0.1 | M | TRIS | 8 | 1.6 | M | Sodium formate ph8 | | | |

ANNEXE 2A - continued

| Well | C | U | Salt | C | U | Buffer | pH | C | U | Precipitant |
|---|---|---|---|---|---|---|---|---|---|---|
| F12 | 0.1 | M | BICINE | 9 | 1.6 | M | Sodium formate ph9 | | | |
| G07 | 0.1 | M | CITRIC ACID | 4 | 2.4 | M | Sodium formate ph4 | | | |
| G08 | 0.1 | M | CITRIC ACID | 5 | 2.4 | M | Sodium formate ph5 | | | |
| G09 | 0.1 | M | MES | 6 | 2.4 | M | Sodium formate ph6 | | | |
| G10 | 0.1 | M | HEPES | 7 | 2.4 | M | Sodium formate ph7 | | | |
| G11 | 0.1 | M | TRIS | 8 | 2.4 | M | Sodium formate ph8 | | | |
| G12 | 0.1 | M | BICINE | 9 | 2.4 | M | Sodium formate ph9 | | | |
| H07 | 0.1 | M | CITRIC ACID | 4 | 3.2 | M | Sodium formate ph4 | | | |
| H08 | 0.1 | M | CITRIC ACID | 5 | 3.2 | M | Sodium formate ph5 | | | |
| H09 | 0.1 | M | MES | 6 | 3.2 | M | Sodium formate ph6 | | | |
| H10 | 0.1 | M | HEPES | 7 | 3.2 | M | Sodium formate ph7 | | | |
| H11 | 0.1 | M | TRIS | 8 | 3.2 | M | Sodium formate ph8 | | | |
| H12 | 0.1 | M | BICINE | 9 | 3.2 | M | Sodium formate ph9 | | | |

ANNEXE: 'Hampton 5" plate

| Well | C | U | Buffer | pH | C | U | Precipitant |
|---|---|---|---|---|---|---|---|
| A01 | 0.1 | M | CITRIC ACID | 4 | 5 | % (w/v) | PEG 6000 |
| A02 | 0.1 | M | CITRIC ACID | 5 | 5 | % (w/v) | PEG 6000 |
| A03 | 0.1 | M | MES | 6 | 5 | % (w/v) | PEG 6000 |
| A04 | 0.1 | M | HEPES | 7 | 5 | % (w/v) | PEG 6000 |
| A05 | 0.1 | M | TRIS | 8 | 5 | % (w/v) | PEG 6000 |
| A06 | 0.1 | M | BICINE | 9 | 5 | % (w/v) | PEG 6000 |
| B01 | 0.1 | M | CITRIC ACID | 4 | 10 | % (w/v) | PEG 6000 |
| B02 | 0.1 | M | CITRIC ACID | 5 | 10 | % (w/v) | PEG 6000 |
| B03 | 0.1 | M | MES | 6 | 10 | (w/v) | PEG 6000 |
| B04 | 0.1 | M | HEPES | 7 | 10 | % (w/v) | PEG 6000 |
| B05 | 0.1 | M | TRIS | 8 | 10 | % (w/v) | PEG 6000 |
| B06 | 0.1 | M | BICINE | 9 | 10 | % (w/v) | PEG 6000 |
| C01 | 0.1 | M | CITRIC ACID | 4 | 20 | % (w/v) | PEG 6000 |
| C02 | 0.1 | M | CITRIC ACID | 5 | 20 | % (w/v) | PEG 6000 |
| C03 | 0.1 | M | MES | 6 | 20 | % (w/v) | PEG 6000 |
| C04 | 0.1 | M | HEPES | 7 | 20 | % (w/v) | PEG 6000 |
| C05 | 0.1 | M | TRIS | 8 | 20 | % (w/v) | PEG 6000 |
| C06 | 0.1 | M | BICINE | 9 | 20 | % (w/v) | PEG 6000 |
| D01 | 0.1 | M | CITRIC ACID | 4 | 30 | % (w/v) | PEG 6000 |
| D02 | 0.1 | M | CITRIC ACID | 5 | 30 | % (w/v) | PEG 6000 |

ANNEXE 2A -continued

| Well | | | | | | Buffer | pH | | | Precipitant |
|---|---|---|---|---|---|---|---|---|---|---|
| D03 | | | | 0.1 | M | MES | 6 | 30 | % (w/v) | PEG 6000 |
| D04 | | | | 0.1 | M | HEPES | 7 | 30 | % (w/v) | PEG 6000 |
| D05 | | | | 0.1 | M | TRIS | 8 | 30 | % (w/v) | PEG 6000 |
| D06 | | | | 0.1 | M | BICINE | 9 | 30 | % (w/v) | PEG 6000 |
| E01 | | | | 0.1 | M | CITRIC ACID | 4 | 10 | % (v/v) | 2-Methyl-2,4-pentanediol |
| E02 | | | | 0.1 | M | Sodium acetate trihydrate | 5 | 10 | % (v/v) | 2-Methyl-2,4-pentanediol |
| E03 | | | | 0.1 | M | MES | 6 | 10 | % (v/v) | 2-Methyl-2,4-pentanediol |
| E04 | | | | 0.1 | M | HEPES | 7 | 10 | % (v/v) | 2-Methyl-2,4-pentanediol |
| E05 | | | | 0.1 | M | TRIS | 8 | 10 | % (v/v) | 2-Methyl-2,4-pentanediol |
| E06 | | | | 0.1 | M | BICINE | 9 | 10 | % (v/v) | 2-Methyl-2,4-pentanediol |
| F01 | | | | 0.1 | M | CITRIC ACID | 4 | 20 | % (v/v) | 2-Methyl-2,4-pentanediol |
| F02 | | | | 0.1 | M | Sodium acetate trihydrate | 5 | 20 | % (v/v) | 2-Methyl-2,4-pentanediol |
| F03 | | | | 0.1 | M | MES | 6 | 20 | % (v/v) | 2-Methyl-2,4-pentanediol |
| F04 | | | | 0.1 | M | HEPES | 7 | 20 | % (v/v) | 2-Methyl-2,4-pentanediol |
| F05 | | | | 0.1 | M | TRIS | 8 | 20 | % (v/v) | 2-Methyl-2,4-pentanediol |
| F06 | | | | 0.1 | M | BICINE | 9 | 20 | % (v/v) | 2-Methyl-2,4-pentanediol |
| G01 | | | | 0.1 | M | CITRIC ACID | 4 | 40 | % (v/v) | 2-Methyl-2,4-pentanediol |
| G02 | | | | 0.1 | M | Sodium acetate trihydrate | 5 | 40 | % (v/v) | 2-Methyl-2,4-pentanediol |
| G03 | | | | 0.1 | M | MES | 6 | 40 | % (v/v) | 2-Methyl-2,4-pentanediol |
| G04 | | | | 0.1 | M | HEPES | 7 | 40 | % (v/v) | 2-Methyl-2,4-pentanediol |
| G05 | | | | 0.1 | M | TRIS | 8 | 40 | % (v/v) | 2-Methyl-2,4-pentanediol |
| G06 | | | | 0.1 | M | BICINE | 9 | 40 | % (v/v) | 2-Methyl-2,4-pentanediol |
| H01 | | | | 0.1 | M | CITRIC ACID | 4 | 65 | % (v/v) | 2-Methyl-2,4-pentanediol |
| H02 | | | | 0.1 | M | Sodium acetate trihydrate | 5 | 65 | % (v/v) | 2-Methyl-2,4-pentanediol |
| H03 | | | | 0.1 | M | MES | 6 | 65 | % (v/v) | 2-Methyl-2,4-pentanediol |
| H04 | | | | 0.1 | M | HEPES | 7 | 65 | % (v/v) | 2-Methyl-2,4-pentanediol |
| H05 | | | | 0.1 | M | TRIS | 8 | 65 | % (v/v) | 2-Methyl-2,4-pentanediol |
| H06 | | | | 0.1 | M | BICINE | 9 | 65 | % (v/v) | 2-Methyl-2,4-pentanediol |
| A07 | 1 | M | Lithium chloride | 0.1 | M | CITRIC ACID | 4 | | | |
| A08 | 1 | M | Lithium chloride | 0.1 | M | CITRIC ACID | 5 | | | |
| A09 | 1 | M | Lithium chloride | 0.1 | M | MES | 6 | | | |
| A10 | 1 | M | Lithium chloride | 0.1 | M | HEPES | 7 | | | |
| A11 | 1 | M | Lithium chloride | 0.1 | M | TRIS | 8 | | | |
| A12 | 1 | M | Lithium chloride | 0.1 | M | BICINE | 9 | | | |
| B07 | 1 | M | Lithium chloride | 0.1 | M | CITRIC ACID | 4 | 10 | % (w/v) | PEG 6000 |
| B08 | 1 | M | Lithium chloride | 0.1 | M | CITRIC ACID | 5 | 10 | % (w/v) | PEG 6000 |
| B09 | 1 | M | Lithium chloride | 0.1 | M | MES | 6 | 10 | % (w/v) | PEG 6000 |
| B10 | 1 | M | Lithium chloride | 0.1 | M | HEPES | 7 | 10 | % (w/v) | PEG 6000 |
| B11 | 1 | M | Lithium chloride | 0.1 | M | TRIS | 8 | 10 | % (w/v) | PEG 6000 |
| B12 | 1 | M | Lithium chloride | 0.1 | M | BICINE | 9 | 10 | % (w/v) | PEG 6000 |
| C07 | 1 | M | Lithium chloride | 0.1 | M | CITRIC ACID | 4 | 20 | % (w/v) | PEG 6000 |
| C08 | 1 | M | Lithium chloride | 0.1 | M | CITRIC ACID | 5 | 20 | % (w/v) | PEG 6000 |
| C09 | 1 | M | Lithium chloride | 0.1 | M | MES | 6 | 20 | % (w/v) | PEG 6000 |
| C10 | 1 | M | Lithium chloride | 0.1 | M | HEPES | 7 | 20 | % (w/v) | PEG 6000 |
| C11 | 1 | M | Lithium chloride | 0.1 | M | TRIS | 8 | 20 | % (w/v) | PEG 6000 |
| C12 | 1 | M | Lithium chloride | 0.1 | M | BICINE | 9 | 20 | % (w/v) | PEG 6000 |
| D07 | 1 | M | Lithium chloride | 0.1 | M | CITRIC ACID | 4 | 30 | % (w/v) | PEG 6000 |

ANNEXE 2A

| | | | | | | | | |
|---|---|---|---|---|---|---|---|---|
| D08 | 1 | M | Lithium chloride | 0.1 | M | CITRIC ACID | 5 | 30 | % (w/v) | PEG 6000 |
| D09 | 1 | M | Lithium chloride | 0.1 | M | MES | 6 | 30 | % (w/v) | PEG 6000 |
| D10 | 1 | M | Lithium chloride | 0.1 | M | HEPES | 7 | 30 | % (w/v) | PEG 6000 |
| D11 | 1 | M | Lithium chloride | 0.1 | M | TRIS | 8 | 30 | % (w/v) | PEG 6000 |
| D12 | 1 | M | Lithium chloride | 0.1 | M | BICINE | 9 | 30 | % (w/v) | PEG 6000 |
| E07 | | | | 0.1 | M | CITRIC ACID | 4 | 5 | % (v/v) | PEG MME 5000 |
| E08 | | | | 0.1 | M | CITRIC ACID | 5 | 5 | % (v/v) | PEG MME 5000 |
| E09 | | | | 0.1 | M | MES | 6 | 5 | % (v/v) | PEG MME 5000 |
| E10 | | | | 0.1 | M | HEPES | 7 | 5 | % (v/v) | PEG MME 5000 |
| E11 | | | | 0.1 | M | TRIS | 8 | 5 | % (v/v) | PEG MME 5000 |
| E12 | | | | 0.1 | M | BICINE | 9 | 5 | % (v/v) | PEG MME 5000 |
| F07 | | | | 0.1 | M | CITRIC ACID | 4 | 10 | % (v/v) | PEG MME 5000 |
| F08 | | | | 0.1 | M | CITRIC ACID | 5 | 10 | % (v/v) | PEG MME 5000 |
| F09 | | | | 0.1 | M | MES | 6 | 10 | % (v/v) | PEG MME 5000 |
| F10 | | | | 0.1 | M | HEPES | 7 | 10 | % (v/v) | PEG MME 5000 |
| F11 | | | | 0.1 | M | TRIS | 8 | 10 | % (v/v) | PEG MME 5000 |
| F12 | | | | 0.1 | M | BICINE | 9 | 10 | % (v/v) | PEG MME 5000 |
| G07 | | | | 0.1 | M | CITRIC ACID | 4 | 15 | % (v/v) | PEG MME 5000 |
| G08 | | | | 0.1 | M | CITRIC ACID | 5 | 15 | % (v/v) | PEG MME 5000 |
| G09 | | | | 0.1 | M | MES | 6 | 15 | % (v/v) | PEG MME 5000 |
| G10 | | | | 0.1 | M | HEPES | 7 | 15 | % (v/v) | PEG MME 5000 |
| G11 | | | | 0.1 | M | TRIS | 8 | 15 | % (v/v) | PEG MME 5000 |
| G12 | | | | 0.1 | M | BICINE | 9 | 15 | % (v/v) | PEG MME 5000 |
| H07 | | | | 0.1 | M | CITRIC ACID | 4 | 20 | % (v/v) | PEG MME 5000 |
| H08 | | | | 0.1 | M | CITRIC ACID | 5 | 20 | % (v/v) | PEG MME 5000 |
| H09 | | | | 0.1 | M | MES | 6 | 20 | % (v/v) | PEG MME 5000 |
| H10 | | | | 0.1 | M | HEPES | 7 | 20 | % (v/v) | PEG MME 5000 |
| H11 | | | | 0.1 | M | TRIS | 8 | 20 | % (v/v) | PEG MME 5000 |
| H12 | | | | 0.1 | M | BICINE | 9 | 20 | % (v/v) | PEG MME 5000 |

ANNEXE: 'Hampton 6" plate

| | | | | | | | | |
|---|---|---|---|---|---|---|---|---|
| A01 | | | | 0.1 | M | CITRIC ACID | 3.5 | 2 | M | ammonium sulfate |
| A02 | | | | 0.1 | M | BIS-TRIS | 5.5 | 3 | M | sodium chloride |
| A03 | | | | | | | 5.6 | 1.4 | M | sodium/potassium phosphate |
| A04 | | | | | | | 7 | 3.5 | M | sodium formate pH 7.0 |
| A05 | 1.1 | M | Sodium malonate ph 7.0 | 0.1 | M | HEPES | 7 | 0.5 | % (v/v) | jeffamine ED-2001 reagent pH 7.0 |
| A06 | | | | 0.1 | M | SODIUM ACETATE TRIHYDRATE | 4.5 | 25 | % (v/v) | PEG 3350 |
| A07 | 0.2 | M | Calcium chloride | 0.1 | M | BIS-TRIS | 6.5 | 45 | % (v/v) | 2-methyl-2,4-pentanediol |
| A08 | 0.05 | M | Ammonium sulfate | 0.1 | M | BIS-TRIS | 6.5 | 30 | % (v/v) | pentaerythritol ethoxylate (15/4 EO/OH) |
| A09 | 0.1 | M | Ammonium acetate | 0.1 | M | BIS-TRIS | 5.5 | 17 | % (w/v) | PEG 10,000 |
| A10 | 0.2 | M | Sodium chloride | 0.1 | M | TRIS | 8.5 | 25 | % (w/v) | PEG 3350 |

ANNEXE 2A-continued

| | | | | | | | | | |
|---|---|---|---|---|---|---|---|---|---|
| A11 | 0.2 | M | Ammonium acetate | 0.1 | M | TRIS | 8.5 | 25 | % (w/v) | PEG 3350 |
| A12 | 0.1 | M | Succinic acid ph 7.0 | | | | | 15 | % (w/v) | PEG 3350 |
| B01 | | | | | | Sodium acetate trihydrate | 4.5 | 2 | M | ammonium sulfate |
| B02 | | | | 0.1 | M | BIS-TRIS | 6.5 | 3 | M | sodium chloride |
| B03 | | | | | | | 6.9 | 1.4 | M | sodium/potassium phosphate |
| B04 | | | | | | | 7 | 1.1 | M | di-ammonium tartrate pH 7.0 |
| B05 | 1 | M | Succinic acid ph 7.0 | 0.1 | M | HEPES | 7 | 1 | % (w/v) | PEG MME 2000 |
| B06 | 0.2 | M | Ammonium acetate | 0.1 | M | BIS-TRIS | 5.5 | 25 | % (w/v) | PEG 3350 |
| B07 | | | | 0.1 | M | BIS-TRIS | 5.5 | 45 | % (v/v) | 2-methyl-2,4-pentanediol |
| B08 | 0.2 | M | Ammonium sulfate | 0.1 | M | BIS-TRIS | 6.5 | 45 | % (v/v) | polypropylene glycol P400 |
| B09 | 0.2 | M | Lithium sulfate | 0.1 | M | BIS-TRIS | 5.5 | 25 | % (w/v) | PEG 3350 |
| B10 | 0.2 | M | Magnesium chloride | 0.1 | M | BIS-TRIS | 5.5 | 25 | % (w/v) | PEG 3350 |
| B11 | 0.2 | M | Sodium formate | 0.1 | M | BIS-TRIS | 5.5 | 25 | % (w/v) | PEG 3350 |
| B12 | | | | | | | | 20 | % (w/v) | PEG 3350 |
| C01 | | | | 0.1 | M | BIS-TRIS | 5.5 | 2 | M | ammonium sulfate |
| C02 | | | | 0.1 | M | HEPES | 7.5 | 3 | M | sodium chloride |
| C03 | | | | | | | 8.2 | 1.4 | M | Sodium/potassium phosphate |
| C04 | | | | | | | 7 | 2.4 | M | Sodium malonate ph 7.0 |
| C05 | 1 | M | Ammonium sulfate | 0.1 | M | HEPES | 7 | 0.5 | % (w/v) | PEG 8000 |
| C06 | | | | 0.1 | M | BIS-TRIS | 6.5 | 25 | % (w/v) | PEG 3350 |
| C07 | 0.2 | M | Ammonium acetate | 0.1 | M | BIS-TRIS | 6.5 | 45 | % (v/v) | 2-methyl-2,4-pentanediol |
| C08 | 0.02 | M | Magnesium chloride | 0.1 | M | HEPES | 7.5 | 22 | % (w/v) | Polyacrylic acid 5100 sodium salt |
| C09 | 0.2 | M | Ammonium sulfate | 0.1 | M | BIS-TRIS | 6.5 | 25 | % (w/v) | PEG 3350 |
| C10 | 0.2 | M | Lithium sulfate | 0.1 | M | BIS-TRIS | 6.5 | 25 | % (w/v) | PEG 3350 |
| C11 | 0.2 | M | Magnesium chloride | 0.1 | M | BIS-TRIS | 6.5 | 25 | % (w/v) | PEG 3350 |
| C12 | 0.15 | M | DL-malic acid ph 7.0 | | | | | 20 | % (w/v) | PEG 3350 |
| D01 | | | | 0.1 | M | BIS-TRIS | 6.5 | 2 | M | Ammonium sulfate |
| D02 | | | | 0.1 | M | TRIS | 8.5 | 3 | M | Sodium chloride |
| D03 | | | | 0.1 | M | HEPES | 7.5 | 1.4 | M | Tri-sodium citrate dihydrate |
| D04 | | | | | | | 7 | 35 | % (v/v) | Tacsimate ph 7.0 |
| D05 | 15 | % (w/v) | Tacsimate ph 7.0 | 0.1 | M | HEPES | 7 | 2 | % (w/v) | Peg 3350 |
| D06 | | | | 0.1 | M | HEPES | 7.5 | 25 | % (w/v) | Peg 3350 |

ANNEXE 2A

| Well | C | U | Salt | C | U | Buffer | pH | C | U | Precipitant | ADDITIVE | C | U | ADDITIVE 1 | C | U | ADDITIVE 2 | C | U |
|---|---|---|---|---|---|---|---|---|---|---|---|---|---|---|---|---|---|---|---|
| D07 | 0.2 | M | Ammonium acetate | | | | | | | | | | | | | | | | |
| D08 | 0.1 | M | Cobalt chloride | | | HEPES | 7.5 | 45 | % (v/v) | 2-methyl-2,4-pentanediol | | | | | | | | | |
| D09 | 0.2 | M | Ammonium sulfate | | | TRIS | 8.5 | 20 | % (w/v) | Polyvinylpyrrolidone K15 | | | | | | | | | |
|  |  |  |  |  |  | HEPES | 7.5 | 25 | % (w/v) | PEG 3350 | | | | | | | | | |

ANNEXE: 'Hampton 6" plate

| Well | C | U | Salt | C | U | Buffer | pH | C | U | Precipitant |
|---|---|---|---|---|---|---|---|---|---|---|
| D10 | 0.2 | M | Lithium sulfate | 0.1 | M | Hepes | 7.5 | 25 | % (w/v) | PEG 3350 |
| D11 | 0.2 | M | Magnesium chloride | 0.1 | M | Hepes | 7.5 | 25 | % (w/v) | PEG 3350 |
| D12 | 0.1 | M | Magnesium formate | | | | | 15 | % (w/v) | PEG 3350 |
| E01 | | | | 0.1 | M | Hepes | 7.5 | 2 | M | Ammonium sulfate |
| E02 | | | | 0.1 | M | Bis-tris | 5.5 | 0.3 | M | Magnesium formate |
| E03 | | | | | | | 7 | 1.8 | M | Tri-ammonium citrate ph 7.0 |
| E04 | | | | | | | 7 | 60 | % (w/v) | Tacsimateph 7.0 |
| E05 | | | | | | | | 25 | % (w/v) | PEG 1500 |
| E06 | | | | | | Tris | 8.5 | 25 | % (w/v) | PEG 3350 |
| E07 | 0.2 | M | Ammonium acetate | 0.1 | M | Tris | 8.5 | 95 | % (v/v) | 2-methyl-2,4-pentanediol |
| E08 | 0.2 | M | Proline | 0.1 | M | Hepes | 7.5 | 10 | % (w/v) | PEG 3350 |
| E09 | 0.2 | M | Ammonium sulfate | 0.1 | M | Tris | 8.5 | 5 | % (w/v) | PEG 3350 |
| E10 | 0.2 | M | Lithium sulfate | 0.1 | M | Tris | 8.5 | 25 | % (w/v) | PEG 3350 |
| E11 | 0.2 | M | Magnesium chloride | 0.1 | M | Tris | 8.5 | 25 | % (w/v) | PEG 3350 |
| E12 | 0.05 | M | zinc acetate | 0.1 | M | TRIS | 8.5 | 20 | % (w/v) | PEG 3350 |
| F01 | | | | | | | | 2 | M | Ammonium sulfate |
| F02 | | | | 0.1 | M | BIS-TRIS | 6.5 | 0.5 | M | Magnesium formate |
| F03 | | | | | | | 7 | 0.8 | M | Succinic acid ph 7.0 |
| F04 | 0.1 | M | Sodium chloride | 0.1 | M | BIS-TRIS | 6.5 | 1.5 | M | Ammonium sulfate |
| F05 | | | | 0.1 | M | HEPES | 7 | 30 | % (v/v) | Jeffamine M-600 reagent ph 7.0 |

ANNEXE 2A -continued

| ID | | | | | | | | | |
|---|---|---|---|---|---|---|---|---|---|
| F06 | | | | 0.1 | M | BIS-TRIS | 6.5 | 20 | PEG MME 5000 |
| F07 | 0.05 | M | Calcium chloride | 0.1 | M | BIS-TRIS | 6.5 | 30 | PEG MME 550 |
| F08 | 0.2 | M | Trimethylamine n-oxide | 0.1 | M | TRIS | 8.5 | 20 | PEG MME 2000 |
| F09 | 0.2 | M | Sodium chloride | 0.1 | M | BIS-TRIS | 5.5 | 25 | PEG 3350 |
| F10 | 0.2 | M | Ammonium acetate | 0.1 | M | BIS-TRIS | 5.5 | 25 | PEG 3350 |
| F11 | 0.2 | M | Potassium/sodium tartrate | | | | | 20 | PEG 3350 |
| F12 | 0.2 | M | Tri-sodium citrate | | | | | 20 | PEG 3350 |
| G01 | | | | 0.1 | M | CITRIC ACID | 3.5 | 3 | Sodium chloride |
| G02 | | | | 0.1 | M | HEPES | 7.5 | 0.5 | Magnesium formate |
| G03 | | | | | | | 7 | 2.1 | DL-malic acid pH 7.0 |
| G04 | 0.8 | M | Potassium/sodium tartrate | 0.1 | M | TRIS | 8.5 | 0.5 | PEG MME 5000 |
| G05 | | | | 0.1 | M | HEPES | 7 | 30 | Jeffamine ED-2001 reagent ph 7.0 |
| G06 | 0.05 | M | Magnesium chloride | 0.1 | M | bis-tris | 6.5 | 28 | PEG MME 2000 |
| G07 | | | | 0.1 | M | HEPES | 7.5 | 30 | PEG MME 550 |
| G08 | 5 | % (w/v) | Tacsimate ph 7.0 | 0.1 | M | HEPES | 7 | 10 | PEG MME 550 |
| G09 | 0.2 | M | Sodium chloride | 0.1 | M | BIS-TRIS | 6.5 | 25 | PEG 3350 |
| G10 | 0.2 | M | Ammonium acetate | 0.1 | M | BIS-TRIS | 6.5 | 25 | PEG 3350 |
| G11 | 0.2 | M | Sodium malonate ph 7.0 | | | | | 20 | PEG 3350 |
| G12 | 0.1 | M | Potassium thiocyanate | | | | | 30 | PEG MME 2000 |
| H01 | | | | | | Sodium acetate trihydrate | 4.5 | 3 | Sodium chloride |
| H02 | | | | 0.1 | M | TRIS | 8.5 | 0.3 | Magnesium formate |
| H03 | | | | | | | 7 | 2.8 | Sodium acetate trihydrate ph 7.0 |
| H04 | 1 | M | Ammonium sulfate | 0.1 | M | BIS-TRIS | 5.5 | 1 | PEG 3350 |
| H05 | | | | 0.1 | M | CITRIC ACID | 3.5 | 25 | PEG 3350 |
| H06 | 0.2 | M | Calcium chloride | 0.1 | M | bis-tris | 5.5 | 45 | 2-methyl-2,4-pentanediol |
| H07 | 0.2 | M | Potassium chloride | 0.05 | M | HEPES | 7.5 | 30 | Pentaerythritol propoxylate (5/4 PO/OH) |

-continued

ANNEXE 2A

| | | | | | | | | | | | | | | | |
|---|---|---|---|---|---|---|---|---|---|---|---|---|---|---|---|
| H08 | 0.005 | M | Magnesium chloride | 0.1 | M | HEPES | 7.5 | 12 | % (w/v) | PEG 3350 | 0.005 | N | Nickel (II) chloride | 0.005 | M | Cadmium Chloride | 0.005 | M | Cobalt chloride |
| H09 | 0.2 | M | Sodium chloride | 0.1 | M | HEPES | 7.5 | 25 | % (w/v) | PEG 3350 | | | | | | |
| H10 | 0.2 | M | Ammonium acetate | 0.1 | M | HEPES | 7.5 | 25 | %(w/v) | PEG 3350 | | | | | | |
| H11 | 0.2 | M | Tri-ammonium citrate ph 7.0 | | | | | 20 | % (w/v) | PEG 3350 | | | | | | |
| H12 | 0.15 | M | Potassium bromide | | | | | 30 | % (w/v) | PEG MME 2000 | | | | | | |

ANNEXE 2B
ANNEXE: The "JCSG" plate

| Well | C | U | Salt | C | U | Buffer | pH | C | U | Precipitant | C | U | Precipitant2 |
|---|---|---|---|---|---|---|---|---|---|---|---|---|---|
| D10 | 0.2 | M | Calcium acetate | 0.1 | M | Sodium cacodylate | 6.5 | 40 | % (v/v) | PEG 300 | | | |
| D11 | 0.14 | M | Calcium chloride | 0.07 | M | Sodium acetate | 4.6 | 14 | % (v/v) | Isopropanol | 30 | % (v/v) | Glycerol |
| D12 | 0.04 | M | Potassium phosphate | | M | | | 16 | % (w/v) | PEG 8000 | 20 | % (v/v) | Glycerol |
| E01 | 1 | M | Tri-sodium citrate | 0.1 | M | Sodium cacodylate | 6.5 | | | | | | |
| E02 | 0.2 | M | Sodium chloride | 0.1 | M | Sodium cacodylate | 6.5 | 2 | M | Ammonium sulfate | | | |
| E03 | 0.2 | M | Sodium chloride | 0.1 | M | HEPES | 7.5 | 10 | % (v/v) | Isopropanol | | | |
| E04 | 0.2 | M | Lithium sulfate | 0.1 | M | TRIS | 8.5 | 1.26 | M | Ammonium sulfate | | | |
| E05 | 0.2 | M | Zinc acetate | 0.1 | M | CAPS | 10.5 | 40 | % (v/v) | MPD | | | |
| E06 | 0.2 | M | Zinc acetate | 0.1 | M | Imidazole | 8 | 20 | % (w/v) | PEG 3000 | | | |
| E07 | | | | 0.1 | M | Sodium cacodylate | 6.5 | 10 | % (v/v) | Isopropanol | | | |
| E08 | 1 | M | Di-ammonium phosphate | 0.1 | M | Sodium acetate | 4.5 | | | | | | |
| E09 | 1.6 | M | Magnesium sulfate | 0.1 | M | MES | 6.5 | | | | | | |
| E10 | | | | 0.1 | M | BICINE | 9 | 10 | % (w/v) | PEG 6000 | | | |
| E11 | 0.16 | M | Calcium acetate | 0.08 | M | Sodium cacodylate | 6.5 | 14.4 | % (w/v) | PEG 8000 | 20 | % (v/v) | Glycerol |
| E12 | 0.05 | M | Cesium chloride | 0.1 | M | Imidazole | 8 | 10 | % (w/v) | PEG 8000 | | | |
| F01 | | | | 0.1 | M | MES | 6.5 | 30 | % (w/v) | Jeffamine M-600 | | | |
| F02 | 3.15 | M | Ammonium sulfate | 0.1 | M | Tri-sodium citrate | 5 | | | | | | |
| F03 | | | | 0.1 | M | TRIS | 8 | 20 | % (v/v) | MPD | | | |
| F04 | | | | 0.1 | M | HEPES | 6.5 | 20 | % (w/v) | Jeffamine M-600 | | | |
| F05 | 0.2 | M | Magnesium chloride | 0.1 | M | TRIS | 8.5 | 50 | % (v/v) | Ethylene glycol | | | |
| F06 | | | | 0.1 | M | BICINE | 9 | 10 | % (v/v) | MPD | | | |
| F07 | 0.8 | M | Succinic acid ph 7.0 | | | | | | | | | | |
| F08 | 2.1 | M | DL-Malic acid ph 7.0 | | | | | | | | | | |
| F09 | 2.4 | M | Sodium malonate ph 7.0 | | | | | | | | | | |
| F10 | 1.1 | M | Sodium malonate | | | HEPES | 7 | 0.5 | % (v/v) | Jeffamine ED-2001 | | | |
| F11 | 1 | M | Succinic acid | 0.1 | M | HEPES | 7 | 1 | % (w/v) | PEG MME 2000 | | | |
| F12 | | | | 0.1 | M | HEPES | 7 | 30 | % (v/v) | Jeffamine M-600 ph 7.0 | | | |

ANNEXE 2B-continued

| Well | C | U | Salt | C | U | Buffer | pH | U | Precipitant | C | U |
|---|---|---|---|---|---|---|---|---|---|---|---|
| G01 | | | | 0.1 | M | HEPES | 7 | | Jeffamine ED-2001 ph 7.0 | 30 | % (v/v) |
| G02 | 0.02 | M | magnesium chloride | 0.1 | M | HEPES | 7.5 | | Polyacrylic acid 5100 sodium salt | 22 | % (w/v) |
| G03 | 0.1 | M | Cobalt chloride | 0.1 | M | TRIS | 8.5 | | Polyvinylpyrrolidone K15 | 20 | % (w/v) |
| G04 | 0.2 | M | Trimethylamine N-oxide | 0.1 | M | TRIS | 8.5 | | PEG MME 2000 | 20 | % (w/v) |
| G05 | 0.005 | M | Cobalt chloride | 0.1 | M | HEPES | 7.5 | | PEG 3350 | 12 | % (w/v) |
| G06 | 0.24 | M | Sodium malonate ph 7.0 | | | | | | PEG 3350 | 20 | % (w/v) |
| G07 | 0.1 | M | Succinic acid ph 7.0 | | | | | | PEG 3350 | 15 | % (w/v) |
| G08 | 0.15 | M | DL-Malic acid ph 7.0 | | | | | | PEG 3350 | 20 | % (w/v) |
| G09 | 0.1 | M | Potassium thiocyanate | | | | | | PEG MME 2000 | 30 | % (w/v) |
| G10 | 0.15 | M | Potassium bromide | | | | | | PEG MME 2000 | 30 | % (w/v) |
| G11 | 2 | M | Ammonium sulfate | 0.1 | M | BIS-TRIS | 5.5 | | | | |
| G12 | 3 | M | Sodium chloride | 0.1 | M | BIS-TRIS | 5.5 | | | | |
| H01 | 0.3 | M | Magnesium formate | 0.1 | M | BIS-TRIS | 5.5 | | | | |
| H02 | 1 | M | Ammonium sulfate | 0.1 | M | BIS-TRIS | 5.5 | | PEG 3350 | 1 | % (w/v) |
| H03 | | | | 0.1 | M | BIS-TRIS | 5.5 | | PEG 3350 | 25 | % (w/v) |
| H04 | 0.2 | M | Calcium chloride | 0.1 | M | BIS-TRIS | 5.5 | | MPD | 45 | % (v/v) |
| H05 | 0.1 | M | Ammonium acetate | 0.1 | M | BIS-TRIS | 5.5 | | MPD | 45 | % (v/v) |
| H06 | 0.1 | M | Ammonium sulfate | 0.1 | M | BIS-TRIS | 5.5 | | PEG 10.000 | 17 | % (w/v) |
| H07 | 0.2 | M | Ammonium acetate | 0.1 | M | BIS-TRIS | 5.5 | | PEG 3350 | 25 | % (w/v) |
| H08 | 0.2 | M | Sodium chloride | 0.1 | M | BIS-TRIS | 5.5 | | PEG 3350 | 25 | % (w/v) |
| H09 | 0.2 | M | Lithium sulfate | 0.1 | M | BIS-TRIS | 5.5 | | PEG 3350 | 25 | % (w/v) |
| H10 | 0.2 | M | Ammonium acetate | 0.1 | M | BIS-TRIS | 5.5 | | PEG 3350 | 25 | % (w/v) |
| H11 | 0.2 | M | Magnesium chloride | 0.1 | M | BIS-TRIS | 5.5 | 0.005 M Cadmium chloride | | | |
| H12 | 0.2 | M | Ammonium acetate | 0.1 | M | HEPES | 7.5 | | MPD | 45 | % (v/v) |

ANNEXE : "The PACT" plate

| Well | C | U | Salt | Buffer | pH | Precipitant | C | U |
|---|---|---|---|---|---|---|---|---|
| A01 | 0 | | 0 | SPG buffer | 4 | PEG 1500 | 25 | % (w/v) |
| A02 | 0 | | 0 | SPG buffer | 5 | PEG 1500 | 25 | % (w/v) |
| A03 | 0 | | 0 | SPG buffer | 6 | PEG 1500 | 25 | % (w/v) |
| A04 | 0 | | 0 | SPG buffer | 7 | PEG 1500 | 25 | % (w/v) |
| A05 | 0 | | 0 | SPG buffer | 8 | PEG 1500 | 25 | % (w/v) |
| A06 | 0 | | 0 | SPG buffer | 9 | PEG 1500 | 25 | % (w/v) |
| A07 | 0.2 | | Sodium chloride | Sodium acetate | 5 | PEG 6000 | 20 | % (w/v) |
| A08 | 0.2 | | Ammonium chloride | Sodium acetate | 5 | PEG 6000 | 20 | % (w/v) |
| A09 | 0.2 | | Lithium chloride | Sodium acetate | 5 | PEG 6000 | 20 | % (w/v) |
| A10 | 0.2 | | Magnesium chloride | Sodium acetate | 5 | PEG 6000 | 20 | % (w/v) |
| A11 | 0.01 | | Calcium chloride | Sodium acetate | 5 | PEG 6000 | 20 | % (w/v) |
| A12 | 0 | | Zinc chloride | Sodium acetate | 5 | PEG 6000 | 20 | % (w/v) |
| B01 | 0 | | 0 | MIB buffer | 4 | PEG 1500 | 25 | % (w/v) |

ANNEXE 2B-continued

| | | | | | | | | |
|---|---|---|---|---|---|---|---|---|
| B02 | 0 | | 0.1 | MIB buffer | 5 | 25 | % (w/v) | PEG 1500 |
| B03 | 0 | | 0.1 | MIB buffer | 6 | 25 | % (w/v) | PEG 1500 |
| B04 | 0 | | 0.1 | MIB buffer | 7 | 25 | % (w/v) | PEG 1500 |
| B05 | 0 | | 0.1 | MIB buffer | 8 | 25 | % (w/v) | PEG 1500 |
| B06 | 0 | | 0.1 | MIB buffer | 9 | 25 | % (w/v) | PEG 1500 |
| B07 | 0.2 | Sodium chloride | 0.1 | MES | 6 | 20 | % (w/v) | PEG 6000 |
| B08 | 0.2 | Ammonium chloride | 0.1 | MES | 6 | 20 | % (w/v) | PEG 6000 |
| B09 | 0.2 | Lithium chloride | 0.1 | MES | 6 | 20 | % (w/v) | PEG 6000 |
| B10 | 0.2 | Magnesium chloride | 0.1 | MES | 6 | 20 | % (w/v) | PEG 6000 |
| B11 | 0.2 | Calcium chloride | 0.1 | MES | 6 | 20 | % (w/v) | PEG 6000 |
| B12 | 0.01 | Zinc chloride | 0.1 | MES | 6 | 20 | % (w/v) | PEG 6000 |
| C01 | 0 | | 0.1 | PCB buffer | 4 | 25 | % (w/v) | PEG 1500 |
| C02 | 0 | | 0.1 | PCB buffer | 5 | 25 | % (w/v) | PEG 1500 |
| C03 | 0 | | 0.1 | PCB buffer | 6 | 25 | % (w/v) | PEG 1500 |
| C04 | 0 | | 0.1 | PCB buffer | 7 | 25 | % (w/v) | PEG 1500 |
| C05 | 0 | | 0.1 | PCB buffer | 8 | 25 | % (w/v) | PEG 1500 |
| C06 | 0 | | 0.1 | PCB buffer | 9 | 25 | % (w/v) | PEG 1500 |
| C07 | 0.2 | Sodium chloride | 0.1 | HEPES | 7 | 20 | % (w/v) | PEG 6000 |
| C08 | 0.2 | Ammonium chloride | 0.1 | HEPES | 7 | 20 | % (w/v) | PEG 6000 |
| C09 | 0.2 | Lithium chloride | 0.1 | HEPES | 7 | 20 | % (w/v) | PEG 6000 |
| C10 | 0.2 | Magnesium chloride | 0.1 | HEPES | 7 | 20 | % (w/v) | PEG 6000 |
| C11 | 0.2 | Calcium chloride | 0.1 | HEPES | 7 | 20 | % (w/v) | PEG 6000 |
| C12 | 0.01 | Zinc chloride | 0.1 | HEPES | 7 | 20 | % (w/v) | PEG 6000 |
| D01 | 0 | | 0.1 | MMT buffer | 4 | 25 | % (w/v) | PEG 1500 |
| D02 | 0 | | 0.1 | MMT buffer | 5 | 25 | % (w/v) | PEG 1500 |
| D03 | 0 | | 0.1 | MMT buffer | 6 | 25 | % (w/v) | PEG 1500 |
| D04 | 0 | | 0.1 | MMT buffer | 7 | 25 | % (w/v) | PEG 1500 |
| D05 | 0 | | 0.1 | MMT buffer | 8 | 25 | % (w/v) | PEG 1500 |
| D06 | 0 | | 0.1 | MMT buffer | 9 | 25 | % (w/v) | PEG 1500 |
| D07 | 0.2 | Sodium chloride | 0.1 | TRIS | 8 | 20 | % (w/v) | PEG 6000 |
| D08 | 0.2 | Ammonium chloride | 0.1 | TRIS | 8 | 20 | % (w/v) | PEG 6000 |
| D09 | 0.2 | Lithium chloride | 0.1 | TRIS | 8 | 20 | % (w/v) | PEG 6000 |
| D10 | 0.2 | Magnesium chloride | 0.1 | TRIS | 8 | 20 | % (w/v) | PEG 6000 |
| D11 | 0.2 | Calcium chloride | 0.1 | TRIS | 8 | 20 | % (w/v) | PEG 6000 |
| D12 | 0.01 | Zinc chloride | 0.1 | TRIS | 8 | 20 | % (w/v) | PEG 6000 |
| E01 | 0.2 | Sodium fluoride | 0 | | 0 | 20 | % (w/v) | PEG 3350 |
| E02 | 0.2 | Sodium bromide | 0 | | 0 | 20 | % (w/v) | PEG 3350 |
| E03 | 0.2 | Sodium iodide | 0 | | 0 | 20 | % (w/v) | PEG 3350 |
| E04 | 0.2 | Potassium thiocyanate | 0 | | 0 | 20 | % (w/v) | PEG 3350 |
| E05 | 0.2 | Sodium nitrate | 0 | | 0 | 20 | % (w/v) | PEG 3350 |
| E06 | 0.2 | Sodium formate | 0 | | 0 | 20 | % (w/v) | PEG 3350 |
| E07 | 0.2 | Sodium acetate | 0 | | 0 | 20 | % (w/v) | PEG 3350 |
| E08 | 0.2 | Sodium sulphate | 0 | | 0 | 20 | % (w/v) | PEG 3350 |
| E09 | 0.2 | Potassium/ sodium tartrate | 0 | | 0 | 20 | % (w/v) | PEG 3350 |
| E10 | 0.2 | Sodium/potassium phosphate | 0 | | 0 | 20 | % (w/v) | PEG 3350 |
| E11 | 0.2 | Sodium citrate | 0 | | 0 | 20 | % (w/v) | PEG 3350 |
| E12 | 0.2 | Sodium malonate | 0 | | 0 | 20 | % (w/v) | PEG 3350 |
| F01 | 0.2 | Sodium fluoride | 0.1 | BIS-TRIS PROPANE | 6.5 | 20 | % (w/v) | PEG 3350 |
| F02 | 0.2 | Sodium bromide | 0.1 | BIS-TRIS PROPANE | 6.5 | 20 | % (w/v) | PEG 3350 |

ANNEXE 2B-continued

| | | | | | | | |
|---|---|---|---|---|---|---|---|
| F03 | 0.2 | Sodium iodide | 0.1 | BIS-TRIS PROPANE | 6.5 | 20 | % (w/v) | PEG 3350 |
| F04 | 0.2 | Potassium thiocyanate | 0.1 | BIS-TRIS PROPANE | 6.5 | 20 | % (w/v) | PEG 3350 |
| F05 | 0.2 | Sodium nitrate | 0.1 | BIS-TRIS PROPANE | 6.5 | 20 | % (w/v) | PEG 3350 |
| F06 | 0.2 | Sodium formate | 0.1 | BIS-TRIS PROPANE | 6.5 | 20 | % (w/v) | PEG 3350 |
| F07 | 0.2 | Sodium acetate | 0.1 | BIS-TRIS PROPANE | 6.5 | 20 | % (w/v) | PEG 3350 |
| F08 | 0.2 | Sodium sulphate | 0.1 | BIS-TRIS PROPANE | 6.5 | 20 | % (w/v) | PEG 3350 |
| F09 | 0.2 | Potassium/ sodium tartrate | 0.1 | BIS-TRIS PROPANE | 6.5 | 20 | % (w/v) | PEG 3350 |
| F10 | 0.2 | Sodium/potassium phosphate | 0.1 | BIS-TRIS PROPANE | 6.5 | 20 | % (w/v) | PEG 3350 |
| F11 | 0.2 | Sodium citrate | 0.1 | BIS-TRIS PROPANE | 6.5 | 20 | % (w/v) | PEG 3350 |
| F12 | 0.2 | Sodium malonate | 0.1 | BIS-TRIS PROPANE | 6.5 | 20 | % (w/v) | PEG 3350 |
| G01 | 0.2 | Sodium fluoride | 0.1 | BIS-TRIS PROPANE | 7.5 | 20 | % (w/v) | PEG 3350 |
| G02 | 0.2 | Sodium bromide | 0.1 | BIS-TRIS PROPANE | 7.5 | 20 | % (w/v) | PEG 3350 |
| G03 | 0.2 | Sodium iodide | 0.1 | BIS-TRIS PROPANE | 7.5 | 20 | % (w/v) | PEG 3350 |
| G04 | 0.2 | Potassium thiocyanate | 0.1 | BIS-TRIS PROPANE | 7.5 | 0 | % (w/v) | PEG 3350 |
| G05 | 0.2 | Sodium nitrate | 0.1 | BIS-TRIS PROPANE | 7.5 | 20 | % (w/v) | PEG 3350 |
| G06 | 0.2 | Sodium formate | 0.1 | BIS-TRIS PROPANE | 7.5 | 20 | % (w/v) | PEG 3350 |
| G07 | 0.2 | Sodium acetate | 0.1 | BIS-TRIS PROPANE | 7.5 | 20 | % (w/v) | PEG 3350 |
| G08 | 0.2 | Sodium sulphate | 0.1 | BIS-TRIS PROPANE | 7.5 | 20 | % (w/v) | PEG 3350 |
| G09 | 0.2 | K/Na tartarte | 0.1 | BIS-TRIS PROPANE | 7.5 | 20 | % (w/v) | PEG 3350 |
| G10 | 0.2 | K/Na phosphate | 0.1 | BIS-TRIS PROPANE | 7.5 | 20 | % (w/v) | PEG 3350 |
| G11 | 0.2 | Sodium citrate | 0.1 | BIS-TRIS PROPANE | 7.5 | 20 | % (w/v) | PEG 3350 |
| G12 | 0.2 | Sodium malonate | 0.1 | BIS-TRIS PROPANE | 7.5 | 20 | % (w/v) | PEG 3350 |
| H01 | 0.2 | Sodium fluoride | 0.1 | BIS-TRIS PROPANE | 8.5 | 20 | % (w/v) | PEG 3350 |
| H02 | 0.2 | Sodium bromide | 0.1 | BIS-TRIS PROPANE | 8.5 | 20 | % (w/v) | PEG 3350 |
| H03 | 0.2 | Sodium iodide | 0.1 | BIS-TRIS PROPANE | 8.5 | 20 | % (w/v) | PEG 3350 |
| H04 | 0.2 | Potassium thiocyanate | 0.1 | BIS-TRIS PROPANE | 8.5 | 20 | % (w/v) | PEG 3350 |

ANNEXE 2B-continued

| Well | C | U | Salt | C | U | Buffer | pH | C | U | Main Precipitant | C | U | Additive |
|---|---|---|---|---|---|---|---|---|---|---|---|---|---|
| H05 | 0.2 | M | Magnesium chloride | 0.1 | M | TRIS | 8.5 | 20 | % (w/v) | BIS-TRIS PROPANE | | | Sodium nitrate |
| H06 | 0.2 | | | 0.1 | M | Tri-sodium citrate | 8.5 | 20 | % (w/v) | BIS-TRIS PROPANE | | | Sodium formate |
| H07 | 0.2 | | | 0.1 | M | Sodium acetate | 8.5 | 20 | % (w/v) | BIS-TRIS PROPANE | | | Sodium acetate |
| H08 | 0.2 | | | 0.1 | M | HEPES | 8.5 | 20 | % (w/v) | BIS-TRIS PROPANE | | | Sodium sulphate |
| H09 | 0.2 | | | 0.1 | M | TRIS HCl | 8.5 | 20 | % (w/v) | BIS-TRIS PROPANE | | | K/Na tartrate |
| H10 | 0.2 | | | 0.1 | M | Tri-sodium citrate | 8.5 | 20 | % (w/v) | BIS-TRIS PROPANE | | | K/Na phosphate |
| H11 | 0.2 | | | 0.1 | M | | | 20 | % (w/v) | BIS-TRIS PROPANE | | | Sodium citrate |
| H12 | 0.2 | | | 0.1 | M | | | 20 | % (w/v) | BIS-TRIS PROPANE | | | Sodium malonate |

ANNEXE: Qiagen "Classic suite" plate

| Well | C | U | Salt | C | U | Buffer | pH | C | U | Main Precipitant | C | U | Additive |
|---|---|---|---|---|---|---|---|---|---|---|---|---|---|
| A03 | 0.2 | M | Magnesium chloride | 0.1 | M | TRIS | 8.5 | 3.4 | M | 1,6-hexanediol | | | |
| A02 | | | | | | Tri-sodium citrate | 5.6 | 2.5 | M | 1,6-hexanediol | | | |
| A01 | 0.01 | M | Cobalt chloride | 0.1 | M | Sodium acetate | 4.6 | 1 | M | 1,6-hexanediol | | | |
| C04 | | | | 0.1 | M | HEPES | 7.5 | 2 | M | Ammonium formate | | | |
| C03 | | | | 0.1 | M | TRIS HCl | 8.5 | 2 | M | Ammonium phosphate | | | |
| C02 | | | | 0.1 | M | Tri-sodium citrate | 5.6 | 1 | M | Ammonium phosphate | | | |
| C01 | | | | | | | | 0.4 | M | Ammonium phosphate | | | |
| C08 | 0.1 | M | Sodium chloride | 0.1 | M | HEPES | 7.5 | 1.6 | M | Ammonium sulfate | | | |
| C09 | 0.01 | M | Cobalt chloride | 0.1 | M | MES | 6.5 | 1.8 | M | Ammonium sulfate | | | |
| C05 | 0 | 0 | | 0.1 | M | sodium acetate | 4.6 | 2 | M | Ammonium sulfate | | | |
| C06 | 0 | 0 | | 0.1 | M | TRIS HCl | 8.5 | 2 | M | Ammonium sulfate | | | |
| C10 | 0.2 | M | K/Na tartrate | 0.1 | M | Tri-sodium citrate | 5.6 | 2 | M | Ammonium sulfate | | | |
| C07 | | | | | | | | 2 | M | Ammonium sulfate | | | |
| E06 | 0.5 | M | Sodium chloride | 0.1 | M | MES | 6.5 | 0.01 | M | Ctab | 0.01 | M | Magnesium chloride |
| E02 | | | | | | | | 10 | % (v/v) | Dioxane | 1.6 | M | Ammonium sulfate |
| E03 | | | | 0 | 0 | | 0 | 35 | % (v/v) | Dioxane | | | |
| E01 | | | | 0.1 | M | BICINE | 9 | 2 | % (v/v) | Dioxane | 10 | % (w/v) | PEG 20000 |
| A12 | | | | 0 | 0 | | 0 | 10 | % (v/v) | Ethanol | 1.5 | M | Sodium chloride |
| B01 | | | | 0.1 | M | TRIS | 8.5 | 20 | % (v/v) | Ethanol | | | |
| B02 | | | | | | | | 25 | % (v/v) | Ethylene glycol | | | |
| E04 | 0.5 | M | Sodium chloride | 0.1 | M | Tri-sodium citrate | 5.6 | 2 | % (v/v) | Ethylene imine polymer | | | |
| E05 | | | | 0.1 | M | TRIS | 8.5 | 12 | % (v/v) | Glycerol | 1.5 | M | Ammonium sulfate |
| C11 | | | | | | | | 1 | M | Imidazole pH 7.0 | | | |
| A10 | 0.2 | M | Magnesium chloride | 0.1 | M | HEPES sodium salt | 7.5 | 30 | % (v/v) | Isopropanol | | | |
| A08 | 0.2 | M | Tri-sodium citrate | 0.1 | M | HEPES sodiums alt | 7.5 | 20 | % (v/v) | Isopropanol | | | |
| A05 | | | | 0.1 | M | HEPES sodium salt | 7.5 | 10 | % (v/v) | Isopropanol | 20 | % (w/v) | PEG 4000 |
| A06 | 0.2 | M | Calcium chloride | 0.1 | M | Sodium acetate | 4.6 | 20 | % (v/v) | Isopropanol | | | |
| A09 | 0.2 | M | Tri-sodium citrate | 0.1 | M | Sodium cacodylate | 6.5 | 30 | % (v/v) | Isopropanol | | | |
| A11 | 0.2 | M | Ammonium acetate | 0.1 | M | TRIS HCl | 8.5 | 30 | % (v/v) | Isopropanol | | | |

ANNEXE 2B-continued

| Well | | | | | | | | | |
|---|---|---|---|---|---|---|---|---|---|
| A07 | 0.1 | M | Tri-sodium citrate | 5.6 | | | 20 | % (w/v) | PEG 4000 |
| A04 | 0 | 0 | 0 | 0 | | | 5 | M | Ammonium sulfate |
| E08 | 0.1 | M | | HEPES | 7.5 | % (v/v) | 20 | | Isopropanol |
| E07 | 0.1 | M | Ferric chloride | Tri-sodium citrate | 5.6 | % (v/v) | 10 | | Isopropanol |
| D01 | 0.1 | M | | HEPES sodium salt | 7.5 | M | 0.8 | | Jeffamine M-600 |
| C12 | | | | | | M | 0.4 | | Jeffamine M-600 |
| | | | | | | | | | Potassium/sodium tartrate |
| E11 | 0.1 | M | Nickel chloride | HEPES sodium salt | 7.5 | M | 1.5 | | Potassium/sodium tartrate |
| E10 | 0.01 | M | Nickel chloride | TRIS | 8.5 | M | 1 | | Lithium sulfate |
| E11 | 0.5 | M | Ammonium sulfate | Tri-sodium citrate | 5.6 | M | 1 | | Lithium sulfate |
| E12 | | | | BICINE | 9 | M | 2 | | Lithium sulfate |
| F01 | | | | | | M | 0.2 | | Magnesium chloride |
| F02 | | | | | | M | 1.6 | | Magnesium formate |
| B10 | | | | MES | 6.5 | M | 0.2 | | Magnesium sulfate |
| B07 | 0.2 | M | Tri-sodium citrate | HEPES | 7.5 | % (v/v) | 70 | | MPD |
| B03 | 0.02 | M | Calcium chloride | HEPES sodium salt | 7.5 | % (v/v) | 30 | | MPD |
| B04 | 0.2 | M | Sodium chloride | Sodium acetate | 4.6 | % (v/v) | 30 | | MPD |
| B09 | 0.2 | M | Ammonium phosphate | Sodium acetate | 4.6 | % (v/v) | 50 | | MPD |
| B05 | 0.2 | M | Ammonium acetate | TRIS | 8.5 | % (v/v) | 30 | | MPD |
| B08 | 0.5 | M | Ammonium sulfate | Tri-sodium citrate | 5.6 | % (v/v) | 30 | | MPD |
| B06 | 0.2 | M | Magnesium acetate | HEPES | 7.5 | % (v/v) | 30 | | MPD |
| G08 | | | | Sodium cacodylate | 6.5 | % (w/v) | 10 | | PEG 1000 |
| H11 | 0.1 | M | | HEPES | 7.5 | % (w/v) | 20 | | PEG 10000 |
| G09 | | | | | | % (w/v) | 30 | | PEG 1500 |
| G11 | 0.2 | M | Ammonium sulfate | Sodium acetate | 4.6 | % (w/v) | 30 | | PEG 2000 MME |
| G10 | 0.01 | M | Nickel chloride | TRIS | 8.5 | % (w/v) | 20 | | PEG 2000 MME |
| H12 | | | | MES | 6.5 | % (w/v) | 12 | | PEG 20000 |
| G02 | 0.2 | M | Calcium chloride | HEPES sodium salt | 7.5 | % (w/v) | 28 | | PEG 400 |
| G04 | 0.2 | M | Magnesium chloride | HEPES sodium salt | 7.5 | % (w/v) | 30 | | PEG 400 |
| G05 | 0.2 | M | Tri-sodium citrate | TRIS HCl | 8.5 | % (w/v) | 30 | | PEG 400 |
| G01 | | | | HEPES sodium salt | 7.5 | % (w/v) | 2 | M | PEG 400 |
| G03 | 0.1 | M | Cadmium chloride | Sodium acetate | 4.6 | % (w/v) | 30 | | PEG 400 |
| H02 | 0.2 | M | Ammonium acetate | Sodium acetate | 4.6 | % (w/v) | 30 | | PEG 4000 |
| H01 | 0.2 | M | Ammonium acetate | Sodium acetate | 4.6 | % (w/v) | 25 | | PEG 4000 |
| H05 | 0.2 | M | Lithium sulfate | TRIS HCl | 8.5 | % (w/v) | 30 | | PEG 4000 |
| H06 | 0.2 | M | Sodium acetate | TRIS HCl | 8.5 | % (w/v) | 30 | | PEG 4000 |
| H03 | 0.2 | M | Ammonium acetate | Tri-sodium citrate | 5.6 | % (w/v) | 30 | | PEG 4000 |
| H07 | 0.2 | M | Ammonium sulfate | Sodium acetate | 4.6 | % (w/v) | 8 | | PEG 4000 |
| G12 | | | | TRIS HCl | 8.5 | % (w/v) | 30 | | PEG 4000 |
| H04 | 0.2 | M | Magnesium chloride | MES | 6.5 | % (w/v) | 30 | | PEG 5000 MME |
| H08 | 0.2 | M | Ammonium sulfate | bicine | 9 | % (w/v) | 20 | | PEG 550 MME |
| G06 | 0.1 | M | Sodium chloride | MES | 6.5 | % (w/v) | 25 | | PEG 550 MME |
| G07 | 0.01 | M | Zinc sulfate | HEPES | 7.5 | % (w/v) | 10 | | PEG 6000 |
| H09 | | | | | | % (w/v) | 10 | | PEG 6000 |
| H10 | | | | HEPES | 7.5 | % (w/v) | 10 | | PEG 8000 |
| F04 | | | | Sodium cacodylate | 6.5 | % (w/v) | 18 | % (w/v) | PEG 8000 |
| F06 | 0.2 | M | Zinc acetate | Sodium cacodylate | 6.5 | % (w/v) | 18 | M | Ethylene glycol |
| F10 | 0.2 | M | Ammonium sulfate | Sodium cacodylate | 6.5 | % (w/v) | 30 | | PEG 8000 |
| F07 | 0.2 | M | Calcium acetate | Sodium cacodylate | 6.5 | % (w/v) | 18 | | PEG 8000 |
| F08 | 0.2 | M | Magnesium acetate | Sodium cacodylate | 6.5 | % (w/v) | 20 | | PEG 8000 |
| F11 | 0.2 | M | Sodium acetate | Sodium cacodylate | 6.5 | % (w/v) | 30 | % (v/v) | MPD |
| F12 | 0.2 | M | Ammonium sulfate | Sodium cacodylate | 6.5 | % (w/v) | 30 | M | sodium chloride |

ANNEXE 2B-continued

| Well | C | U | Salt | C | U | Buffer | pH | C | U | Precipitant | C | U | |
|---|---|---|---|---|---|---|---|---|---|---|---|---|---|
| F05 | 0.5 | M | Lithium sulfate | | | | | | | | | | |
| F09 | 0.05 | M | Potassium phosphate | | | TRIS HCl | 8.5 | 15 | % (w/v) | PEG 8000 | | | |
| F03 | | | | | | HEPES | 7.5 | 20 | % (w/v) | PEG 8000 | | | |
| D03 | 0.05 | M | Cadmium sulfate | | | Imidazole | 6.5 | 8 | % (w/v) | PEG 8000 | | | |
| D02 | | | | | | Sodium cacodylate | 6.5 | 1 | M | Sodium acetate | | | |
| D04 | | | | | | HEPES | 7.5 | 1.4 | M | Sodium acetate | | | |
| D07 | | | | | | MES | 6.5 | 4.3 | M | Sodium chloride | | | |
| D06 | 0.1 | M | Sodium phosphate | | | | | 2 | M | Sodium chloride | 0.1 | M | potassium phosphate |
| D05 | | | | | | Sodium acetate | 4.6 | 2 | M | Sodium chloride | | | |
| D11 | | | | | | Sodium acetate | 4.6 | 2 | M | Sodium formate | | | |
| D12 | | | | | | | | 4 | M | Sodium formate | | | |
| D10 | | | | | | HEPES sodium salt | 7.5 | 0.8 | M | Sodium phosphate | 0.8 | M | potassium phosphate |
| B11 | | | | | | TRIS | 8.5 | 25 | % (v/v) | tert-butanol | | | |
| B12 | | | | | | Tri-sodium citrate | 5.6 | 35 | % (v/v) | tert-butanol | | | |
| D08 | | | | | | HEPES sodium salt | 7.5 | 1.4 | M | tri-sodium citrate | | | |
| D09 | | | | | | | | 1.6 | M | tri-sodium citrate pH 6.5 | | | |

ANNEXE : Qiagen "The PEGS" plate

| Well | Salt | C | U | Buffer | pH | C | U | Precipitant |
|---|---|---|---|---|---|---|---|---|
| A01 | | | | Sodium acetate | 4.6 | 40 | % (v/v) | PEG 200 |
| A02 | | | | Sodium acetate | 4.6 | 30 | % (v/v) | PEG 300 |
| A03 | | | | Sodium acetate | 4.6 | 30 | % (v/v) | PEG 400 |
| A04 | | | | Sodium acetate | 4.6 | 25 | % (w/v) | PEG 550 MME |
| A05 | | | | Sodium acetate | 4.6 | 25 | % (w/v) | PEG 1000 |
| A06 | | | | Sodium acetate | 9.6 | 25 | % (w/v) | PEG 2000 MME |
| A07 | | | | MES | 6.5 | 40 | % (v/v) | PEG 200 |
| A08 | | | | MES | 6.5 | 30 | % (v/v) | PEG 300 |
| A09 | | | | MES | 6.5 | 30 | % (v/v) | PEG 400 |
| A10 | | | | MES | 6.5 | 25 | % (w/v) | PEG 550 MME |
| A11 | | | | MES | 6.5 | 25 | % (w/v) | PEG 1000 |
| A12 | | | | MES | 6.5 | 25 | % (w/v) | PEG 2000 MME |
| B01 | | | | HEPES sodium salt | 7.5 | 40 | % (v/v) | PEG 200 |
| B02 | | | | HEPES sodium salt | 7.5 | 30 | % (v/v) | PEG 300 |
| B03 | | | | HEPES sodium salt | 7.5 | 30 | % (v/v) | PEG 400 |
| B04 | | | | HEPES sodium salt | 7.5 | 25 | % (w/v) | PEG 550 MME |
| B05 | | | | HEPES sodium salt | 7.5 | 25 | % (w/v) | PEG 1000 |
| B06 | | | | HEPES sodium salt | 7.5 | 25 | % (w/v) | PEG 2000 MME |
| B07 | | | | TRIS HCl | 8.5 | 40 | % (v/v) | PEG 200 |
| B08 | | | | TRIS HCl | 8.5 | 30 | % (v/v) | PEG 300 |
| B09 | | | | TRIS HCl | 8.5 | 30 | % (v/v) | PEG 400 |
| B10 | | | | TRIS HCl | 8.5 | 25 | % (w/v) | PEG 550 MME |
| B11 | | | | TRIS HCl | 8.5 | 25 | % (w/v) | PEG 1000 |
| B12 | | | | TRIS HCl | 8.5 | 25 | % (w/v) | PEG 2000 MME |
| C01 | | | | Sodium acetate | 4.6 | 25 | % (w/v) | PEG 3000 |
| C02 | | | | Sodium acetate | 4.6 | 25 | % (w/v) | PEG 4000 |
| C03 | | | | Sodium acetate | 9.6 | 25 | % (w/v) | PEG 6000 |
| C04 | | | | Sodium acetate | 9.6 | 25 | % (w/v) | PEG 8000 |
| C05 | | | | Sodium acetate | 9.6 | 20 | % (w/v) | PEG 10000 |
| C06 | | | | Sodium acetate | 9.6 | 15 | % (w/v) | PEG 20000 |

ANNEXE 2B-continued

| | | | | | | | | |
|---|---|---|---|---|---|---|---|---|
| C07 | | | | 0.1 | M | MES | 6.5 | 25 % (w/v) PEG 3000 |
| C08 | | | | 0.1 | M | MES | 6.5 | 25 % (w/v) PEG 4000 |
| C09 | | | | 0.1 | M | MES | 6.5 | 25 % (w/v) PEG 6000 |
| C10 | | | | 0.1 | M | MES | 6.5 | 25 % (w/v) PEG 8000 |
| C11 | | | | 0.1 | M | MES | 6.5 | 20 % (w/v) PEG 10000 |
| C12 | | | | 0.1 | M | MES | 6.5 | 15 % (w/v) PEG 20000 |
| D01 | | | | 0.1 | M | HEPES sodium salt | 7.5 | 25 % (w/v) PEG 3000 |
| D02 | | | | 0.1 | M | HEPES sodium salt | 7.5 | 25 % (w/v) PEG 4000 |
| D03 | | | | 0.1 | M | HEPES sodium salt | 7.5 | 25 % (w/v) PEG 6000 |
| D04 | | | | 0.1 | M | HEPES sodium salt | 7.5 | 25 % (w/v) PEG 8000 |
| D05 | | | | 0.1 | M | HEPES sodium salt | 7.5 | 20 % (w/v) PEG 10000 |
| D06 | | | | 0.1 | M | HEPES sodium salt | 7.5 | 15 % (w/v) PEG 20000 |
| D07 | | | | 0.1 | M | TRIS HCl | 8.5 | 25 % (w/v) PEG 3000 |
| D08 | | | | 0.1 | M | TRIS HCl | 8.5 | 25 % (w/v) PEG 4000 |
| D09 | | | | 0.1 | M | TRIS HCl | 8.5 | 25 % (w/v) PEG 6000 |
| D10 | | | | 0.1 | M | TRIS HCl | 8.5 | 25 % (w/v) PEG 8000 |
| D11 | | | | 0.1 | M | TRIS HCl | 8.5 | 20 % (w/v) PEG 10000 |
| D12 | | | | 0.1 | M | TRIS HCl | 8.5 | 15 % (w/v) PEG 20000 |
| E01 | 0.2 | M | Sodium fluoride | | | | | 20 % (w/v) PEG 3350 |
| E02 | 0.2 | M | Potassium fluoride | | | | | 20 % (w/v) PEG 3350 |
| E03 | 0.2 | M | Ammonium fluoride | | | | | 20 % (w/v) PEG 3350 |
| E04 | 0.2 | M | Lithium chloride | | | | | 20 % (w/v) PEG 3350 |
| E05 | 0.2 | M | Magnesium chloride | | | | | 20 % (w/v) PEG 3350 |
| E06 | 0.2 | M | Sodium chloride | | | | | 20 % (w/v) PEG 3350 |
| E07 | 0.2 | M | Calcium chloride | | | | | 20 % (w/v) PEG 3350 |
| E08 | 0.2 | M | Potassium chloride | | | | | 20 % (w/v) PEG 3350 |
| E09 | 0.2 | M | Ammonium chloride | | | | | 20 % (w/v) PEG 3350 |
| E10 | 0.2 | M | Sodium iodide | | | | | 20 % (w/v) PEG 3350 |
| E11 | 0.2 | M | Potassium iodide | | | | | 20 % (w/v) PEG 3350 |
| E12 | 0.2 | M | Ammonium iodide | | | | | 20 % (w/v) PEG 3350 |
| F01 | 0.2 | M | Sodium thiocyanate | | | | | 20 % (w/v) PEG 3350 |
| F02 | 0.2 | M | Potassium thiocyanate | | | | | 20 % (w/v) PEG 3350 |
| F03 | 0.2 | M | Lithium nitrate | | | | | 20 % (w/v) PEG 3350 |
| F04 | 0.2 | M | Magnesium nitrate | | | | | 20 % (w/v) PEG 3350 |
| F05 | 0.2 | M | Sodium nitrate | | | | | 20 % (w/v) PEG 3350 |
| F06 | 0.2 | M | Potassium nitrate | | | | | 20 % (w/v) PEG 3350 |
| F07 | 0.2 | M | Ammonium nitrate | | | | | 20 % (w/v) PEG 3350 |
| F08 | 0.2 | M | Magnesium formate | | | | | 20 % (w/v) PEG 3350 |
| F09 | 0.2 | M | Sodium formate | | | | | 20 % (w/v) PEG 3350 |
| F10 | 0.2 | M | Potassium formate | | | | | 20 % (w/v) PEG 3350 |
| F11 | 0.2 | M | Ammonium formate | | | | | 20 % (w/v) PEG 3350 |
| F12 | 0.2 | M | Lithium acetate | | | | | 20 % (w/v) PEG 3350 |
| G01 | 0.2 | M | Magnesium acetate | | | | | 20 % (w/v) PEG 3350 |
| G02 | 0.2 | M | Zinc acetate | | | | | 20 % (w/v) PEG 3350 |
| G03 | 0.2 | M | Sodium acetate | | | | | 20 % (w/v) PEG 3350 |
| G04 | 0.2 | M | Calcium acetate | | | | | 20 % (w/v) PEG 3350 |
| G05 | 0.2 | M | Potassium acetate | | | | | 20 % (w/v) PEG 3350 |
| G06 | 0.2 | M | Ammonium acetate | | | | | 20 % (w/v) PEG 3350 |
| G07 | 0.2 | M | Lithium sulfate | | | | | 20 % (w/v) PEG 3350 |
| G08 | 0.2 | M | Magnesium sulfate | | | | | 20 % (w/v) PEG 3350 |
| G09 | 0.2 | M | Sodium sulfate | | | | | 20 % (w/v) PEG 3350 |

ANNEXE 2B-continued

| | C | U | Salt | C | U | | | | Precipitant |
|---|---|---|---|---|---|---|---|---|---|
| G10 | 0.2 | M | Potassium sulfate | | | | 20 | % (w/v) | PEG 3350 |
| G11 | 0.2 | M | Ammonium sulfate | | | | 20 | % (w/v) | PEG 3350 |
| G12 | 0.2 | M | Di-sodium tartrate | | | | 20 | % (w/v) | PEG 3350 |
| H01 | 0.2 | M | Potassium/ sodium tartrate | | | | 20 | % (w/v) | PEG 3350 |
| H02 | 0.2 | M | Di-ammonium tartrate | | | | 20 | % (w/v) | PEG 3350 |
| H03 | 0.2 | M | Sodium phosphate | | | | 20 | % (w/v) | PEG 3350 |
| H04 | 0.2 | M | Di-sodium phosphate | | | | 20 | % (w/v) | PEG 3350 |
| H05 | 0.2 | M | Potassium phosphate | | | | 20 | % (w/v) | PEG 3350 |
| H06 | 0.2 | M | Di-potassium phosphate | | | | 20 | % (w/v) | PEG 3350 |
| H07 | 0.2 | M | Ammonium phosphate | | | | 20 | % (w/v) | PEG 3350 |
| H08 | 0.2 | M | Di-ammonium phosphate | | | | 20 | % (w/v) | PEG 3350 |
| H09 | 0.2 | M | Tri-lithium citrate | | | | 20 | % (w/v) | PEG 3350 |
| H10 | 0.2 | M | Tri-sodium citrate | | | | 20 | % (w/v) | PEG 3350 |
| H11 | 0.2 | M | Tri-potassium citrate | | | | 20 | % (w/v) | PEG 3350 |
| H12 | 0.18 | M | Tri-ammonium citrate | | | | 20 | % (w/v) | PEG 3350 |

ANNEXE: Rigaku "Wizard I & II" plate

| Well | C | U | Salt | C | U | Buffer | pH | C | U | Precipitant | C | U | ADDITIVE |
|---|---|---|---|---|---|---|---|---|---|---|---|---|---|
| D10 | 0.2 | M | Calcium acetate | 0.1 | M | Imidazole/HCl | 8 | 10 | % (w/v) | PEG-8000 | | | |
| D11 | 0.2 | M | Lithium sulfate | 0.1 | M | TRIS BASE/HCl | 8.5 | 1.26 | M | Ammonium sulfate | | | |
| D12 | 0.2 | M | Zinc acetate | 0.1 | M | Sodium acetate/ citric acid | 4.5 | 20 | % (w/v) | PEG-1000 | | | |
| E01 | 0.2 | M | Zinc acetate | 0.1 | M | Sodium acetate/ citric acid | 4.5 | 10 | % (w/v) | PEG-3000 | | | |
| E02 | 0.2 | M | Lithium sulfate | 0.1 | M | MES/NaOH | 6 | 3.5 | % (v/v) | 2-methyl-2,4-pentanediol | | | |
| E03 | 0.2 | M | Magnesium chloride | 0.1 | M | Tris base/HCl | 8.5 | 20 | % (w/v) | PEG-8000 | | | |
| E04 | 0.2 | M | Sodium chloride | 0.1 | M | sodium cacodylate/ HCl | 6.5 | 2 | M | Ammonium sulfate | | | |
| E05 | 0.2 | M | Sodium chloride | 0.1 | M | HEPES/NaOH | 7.5 | 20 | % (v/v) | 1,4-butanediol | | | |
| E06 | 0.2 | M | Lithium sulfate | 0.1 | M | Sodium phosphate dibasic/citric acid | 4.2 | 10 | % (v/v) | 2-propanol | | | |
| E07 | 0.2 | M | Sodium chloride | 0.1 | M | TRIS BASE/HCl | 7 | 30 | % (w/v) | PEG-3000 | | | |
| E08 | 0.2 | M | Sodium chloride | 0.1 | M | Potassium phosphate monobasic/sodium phosphate dibasic | 6.2 | 10 | % (w/v) | PEG-8000 | | | |
| E09 | | | | 0.1 | M | Sodium phosphate dibasic/citric acid | 4.2 | 2 | M | Ammonium sulfate | | | |
| E10 | | | | 0.1 | M | TRIS BASE/HCL | 8.5 | 1 | M | Ammonium phosphate dibasic | | | |
| E11 | 0.2 | M | Zinc acetate | 0.1 | M | Sodium cacodylate/ HCl | 6.5 | 10 | % (v/v) | 2-propanol | | | |

ANNEXE 2B-continued

| | | | | | | | | | | |
|---|---|---|---|---|---|---|---|---|---|---|
| E12 | 0.2 | M | Lithium sulfate | 0.1 | M | Sodium cacodylate/HCl | 6.5 | | | PEG-400 |
| F01 | 0.2 | M | Lithium sulfate | 0.1 | M | Sodium citrate/citric acid | 5.5 | 15 | % (v/v) | Reagent alcohol* |
| F02 | 0.2 | M | Sodium chloride | 0.1 | M | Potassium phosphate monobasic/sodium phosphate dibasic | 6.2 | 20 | % (w/v) | PEG-1000 |
| F03 | | | | 0.1 | M | HEPES/NaOH | 7.5 | 1.26 | M | Ammonium sulfate |
| F04 | | | | 0.1 | M | CHES/NaOH | 9.5 | 1 | M | Sodium citrate tribasic |
| F05 | 0.2 | M | Magnesium chloride | 0.1 | M | TRIS BASE/HCl | 7 | 2.5 | M | Sodium chloride |
| F06 | 0.2 | M | Calcium acetate | 0.1 | M | TRIS BASE/HCl | 7 | 20 | % (w/v) | PEG-3000 |
| F07 | | | | 0.1 | M | Sodium phosphate dibasic/citric acid | 4.2 | 1.6 | M | Sodium phosphate monobasic |
| F08 | 0.2 | M | Zinc acetate | 0.1 | M | MES/NaOH | 6 | 15 | % (v/v) | reagent alcohol* |
| F09 | | | | 0.1 | M | Sodium acetate/citric acid | 4.5 | 35 | % (v/v) | 2-methyl-2,4-pentanediol |
| F10 | | | | 0.1 | M | Imidazole/HCl | 8 | 10 | % (v/v) | 2-propanol |
| F11 | 0.2 | M | Magnesium chloride | 0.1 | M | HEPES/NaOH | 7.5 | 15 | % (v/v) | Reagent alcohol* |
| F12 | 0.2 | M | Sodium chloride | 0.1 | M | Imidazole/HCl | 8 | 30 | % (w/v) | PEG-8000 |
| G01 | 0.2 | M | Sodium chloride | 0.1 | M | HEPES/NaOH | 7.5 | 35 | % (v/v) | 2-methyl-2,4-pentanediol |
| G02 | | | | 0.1 | M | CHES/NaOH | 9.5 | 30 | % (w/v) | PEG-400 |
| G03 | 0.2 | M | Magnesium chloride | 0.1 | M | sodium cacodylate/HCl | 6.5 | 10 | % (w/v) | PEG-3000 |
| G04 | 0.2 | M | Calcium acetate | 0.1 | M | MES/NaOH | 6 | 20 | % (w/v) | PEG-8000 |
| G05 | 0.2 | M | Sodium chloride | 0.1 | M | CHES/NaOH | 9.5 | 26 | % (v/v) | Ammonium sulfate |
| G06 | 0.2 | M | Zinc acetate | 0.1 | M | Imidazole/HCl | 8 | 20 | % (v/v) | 1,4-butanediol |
| G07 | 0.2 | M | Sodium chloride | 0.1 | M | TRIS BASE/HCL | 7 | 1 | M | Sodium citrate tribasic |
| G08 | | | | 0.1 | M | TRIS BASE/HCl | 8.5 | 20 | % (w/v) | PEG-1000 |
| G09 | 0.2 | M | Sodium chloride | 0.1 | M | Sodium citrate/citric acid | 5.5 | 1 | M | Ammonium phosphate dibasic |
| G10 | | | | 0.1 | M | Imidazole/HCl | 8 | 10 | % (w/v) | PEG-8000 |
| G11 | | | | 0.1 | M | Sodium acetate/citric acid | 4.5 | 0.8 | M | Sodium phosphate monobasic / 1.2 M Potassium phosphate dibasic |
| G12 | 0.2 | M | Sodium chloride | 0.1 | M | Sodium phosphate dibasic/citric acid | 4.2 | 10 | % (w/v) | PEG-3000 |
| H01 | 0.2 | M | Lithium sulfate | 0.1 | M | TRIS BASE/HCl | 7 | 1 | M | Potassium/sodium tartrate |
| H02 | 0.2 | M | Lithium sulfate | 0.1 | M | Sodium acetate/citric acid | 4.5 | 2.5 | M | Sodium chloride |
| H03 | 0.2 | M | Sodium chloride | 0.1 | M | CAPS/NaOH | 10.5 | 20 | % (w/v) | PEG-8000 |
| H04 | 0.2 | M | Zinc acetate | 0.1 | M | Imidazole/HCl | 8 | 20 | % (w/v) | PEG-3000 |
| H05 | 0.2 | M | Lithium sulfate | 0.1 | M | TRIS BASE/HCl | 7 | 2 | M | Ammonium sulfate |
| H06 | 0.2 | M | Sodium chloride | 0.1 | M | HEPES/NaOH | 7.5 | 30 | % (v/v) | PEG-400 |
| H07 | 0.2 | M | Magnesium chloride | 0.1 | M | TRIS BASE/NaOH | 7 | 10 | % (w/v) | PEG-8000 |
| H08 | 0.2 | M | Magnesium chloride | 0.1 | M | Sodium cacodylate/HCl | 6.5 | 20 | % (v/v) | PEG-1000 |
| H09 | | | | 0.1 | M | MES/NaOH | 6 | 1.26 | M | Ammonium sulfate |
| H10 | 0.2 | M | Sodium chloride | 0.1 | M | Imidazole/HCl | 8 | 1 | M | Ammonium phosphate dibasic |
| H11 | 0.2 | M | Zinc acetate | 0.1 | M | Imidazole/HCl | 8 | 2.5 | M | Sodium chloride |

ANNEXE 2B-continued

| | | | | | | | | | | | |
|---|---|---|---|---|---|---|---|---|---|---|---|
| H12 | | | 0.1 | M | MES/NaOH | 6 | 1 | M | Potassium/ sodium tartrate | | |
| A01 | | | 0.1 | M | CHES/NaOH | 9.5 | 20 | % (w/v) | PEG-8000 | | |
| A02 | 0.2 | M | Sodium chloride | 0.1 | M | HEPES/NaOH | 7.5 | 10 | % (v/v) | 2-propanol | | |
| A03 | | | 0.1 | M | CHES/NaOH | 9.5 | 15 | % (v/v) | reagent alcohol* | | |
| A04 | 0.2 | M | Magnesium chloride | 0.1 | M | Imidazole/HCl | 8 | 35 | % (v/v) | 2-methyl-2,4-pentanediol | | |
| A05 | | | 0.1 | M | CAPS/NaOH | 10.5 | 30 | % (v/v) | PEG-400 | | |
| A06 | | | 0.1 | M | Sodium citrate/citric acid | 5.5 | 20 | % (w/v) | PEG-3000 | | |
| A07 | 0.2 | M | Zinc acetate | 0.1 | M | MES/NaOH | 6 | 10 | % (w/v) | PEG-8000 | | |
| A08 | | | 0.1 | M | Sodium citrate/citric acid | 5.5 | 2 | M | ammonium sulfate | | |
| A09 | | | 0.1 | M | Sodium acetate/citric acid | 4.5 | 1 | M | ammonium phosphate dibasic | | |
| A10 | | | 0.1 | M | TRIS BASE/HCl | 7 | 20 | % (w/v) | PEG-2000 MME | | |
| A11 | 0.2 | M | Lithium sulfate | 0.1 | M | MES/NaOH | 6 | 20 | % (v/v) | 1,4-butanediol | | |
| A12 | 0.2 | M | Calcium acetate | 0.1 | M | Imidazole/HCl | 8 | 20 | % (w/v) | PEG-1000 | | |
| B01 | | | 0.1 | M | Sodium cacodylate/HCl | 6.5 | 1.26 | M | ammonium sulfate | | |
| B02 | | | 0.1 | M | Sodium cacodylate/HCl | 6.5 | 1 | M | sodium citrate tribasic | | |
| B03 | 0.2 | M | Lithium sulfate | 0.1 | M | Imidazole/HCl | 8 | 10 | % (w/v) | PEG-3000 | | |
| B04 | | | | | Potassium phosphate monobasic/sodium phosphate dibasic | 6.2 | 2.5 | M | Sodium chloride | | | |
| B05 | 0.2 | M | Lithium sulfate | 0.1 | M | Sodium acetate/citric acid | 4.5 | 30 | % (w/v) | PEG-8000 | | |
| B06 | 0.2 | M | Sodium chloride | 0.1 | M | Imidazole/HCl | 8 | 1 | M | Potassium/ sodium tartrate | | |
| B07 | | | | 0.1 | M | TRIS BASE/HCl | 7 | 20 | % (w/v) | PEG-1000 | | |
| B08 | 0.2 | M | Sodium chloride | 0.1 | M | Imidazole/HCl | 8 | 0.4 | M | Sodium phosphate monobasic | 1.6 | M | Potassium phosphate dibasic |
| B09 | | | | 0.1 | M | HEPES/NaOH | 7.5 | 20 | % (v/v) | PEG-8000 | | |
| B10 | | | | 0.1 | M | TRIS BASE/HCl | 8.5 | 10 | % (v/v) | 2-propanol | | |
| B11 | 0.2 | M | Magnesium chloride | 0.1 | M | Imidazole/HCl | 8 | 15 | % (v/v) | Reagent alcohol* | | |
| B12 | 0.2 | M | Sodium chloride | 0.1 | M | TRIS BASE/HCl | 7 | 35 | % (v/v) | 2-methyl-2,4-pentanediol | | |
| C01 | 0.2 | M | Magnesium chloride | 0.1 | M | TRIS BASE/HCl | 8.5 | 30 | % (v/v) | PEG-400 | | |
| C02 | | | | 0.1 | M | CHES/NaOH | 9.5 | 10 | % (w/v) | PEG-3000 | | |
| C03 | 0.2 | M | Lithium sulfate | 0.1 | M | CAPS/NaOH | 10.5 | 1.2 | M | Sodium phosphate monobasic | 0.8 | M | Potassium phosphate dibasic |
| C04 | 0.2 | M | Sodium chloride | 0.1 | M | HEPES/NaOH | 7.5 | 20 | % (w/v) | PEG-3000 | | |
| C05 | 0.2 | M | Sodium chloride | 0.1 | M | CHES/NaOH | 9.5 | 10 | % (w/v) | PEG-8000 | | |
| C06 | 0.2 | M | Sodium chloride | 0.1 | M | Sodium acetate/citric acid | 4.5 | 1.26 | M | Ammonium sulfate | | |
| C07 | 0.2 | M | Sodium chloride | 0.1 | M | Sodium phosphate dibasic/citric acid | 4.2 | 20 | % (w/v) | PEG-8000 | | |
| C08 | | | | 0.1 | M | Potassium phosphate | 6.2 | 10 | % (w/v) | PEG-3000 | | |

ANNEXE 2B-continued

| | C | U | Buffer | pH | C | U | Precipitant | | U | Precipitant 2 | | U |
|---|---|---|---|---|---|---|---|---|---|---|---|---|
| C09 | 0.2 | M | Lithium sulfate | | | | | | | monobasic/sodium phosphate dibasic | | |
| | | | | | | | | | | CAPS/NaOH | 10.5 | M |
| C10 | | | | | | | | | | Imidazole/HCl | 8 | M |
| C11 | | | | | | | | | | Sodium acetate/citric acid | 4.5 | | 20 | % (v/v) | 1.4-butanediol |
| C12 | | | | | | | | | | Imidazole/HCl | 8 | M | 1 | M | Sodium citrate tribasic |
| D01 | | | | | | | | | | Imidazole/HCl | 8 | M | 2.5 | M | Sodium chloride |
| D02 | 0.2 | M | Lithium sulfate | | | | | | | CHES/NaOH | 9.5 | M | 1 | M | Potassium/sodium tartrate |
| D03 | 0.2 | M | Lithium sulfate | | | | | | | Sodium phosphate dibasic/citric acid | 4.2 | | 20 | % (w/v) | PEG-1000 |
| D04 | 0.2 | M | Calcium acetate | | | | | | | MES/NaOH | 6 | | 10 | % (v/v) | 2-propanol |
| D05 | | | | | | | | | | CHES/NaOH | 9.5 | | 30 | % (w/v) | PEG-3000 |
| D06 | | | | | | | | | | TRIS BASE/HCl | 7 | | 15 | % (v/v) | Reagent alcohol* |
| D07 | 0.1 | M | | | | | | | | Potassium phosphate monobasic/sodium phosphate dibasic | 6.2 | | 35 | % (v/v) | 2-methyl-2,4-pentanediol |
| D08 | 0.2 | M | Calcium acetate | | | | | | | Sodium acetate/citric acid | 4.5 | | 30 | % (w/v) | PEG-400 |
| D09 | | | | | | | | | | Sodium acetate/citric acid | 4.5 | | 20 | % (w/v) | PEG-3000 |

ANNEXE: Hampton "Salt grid" plate

| Well | C | U | Buffer | pH | C | U | Precipitant | | U | Precipitant 2 | C | U | pH |
|---|---|---|---|---|---|---|---|---|---|---|---|---|---|
| A01 | 0.1 | M | CITRIC ACID | 4 | 0.8 | M | Ammonium sulfate | | | | | | |
| A02 | 0.1 | M | CITRIC ACID | 5 | 0.8 | M | Ammonium sulfate | | | | | | |
| A03 | 0.1 | M | MES monohydrate | 6 | 0.8 | M | Ammonium sulfate | | | | | | |
| A04 | 0.1 | M | HEPES | 7 | 0.8 | M | Ammonium sulfate | | | | | | |
| A05 | 0.1 | M | TRIS | 8 | 0.8 | M | Ammonium sulfate | | | | | | |
| A06 | 0.1 | M | BICINE | 9 | 0.8 | M | Ammonium sulfate | | | | | | |
| B01 | 0.1 | M | CITRIC ACID | 4 | 1.6 | M | Ammonium sulfate | | | | | | |
| B02 | 0.1 | M | CITRIC ACID | 5 | 1.6 | M | Ammonium sulfate | | | | | | |
| B03 | 0.1 | M | MES monohydrate | 6 | 1.6 | M | Ammonium sulfate | | | | | | |
| B04 | 0.1 | M | HEPES | 7 | 1.6 | M | Ammonium sulfate | | | | | | |
| B05 | 0.1 | M | TRIS | 8 | 1.6 | M | Ammonium sulfate | | | | | | |
| B06 | 0.1 | M | BICINE | 9 | 1.6 | M | Ammonium sulfate | | | | | | |
| C01 | 0.1 | M | CITRIC ACID | 4 | 2.4 | M | Ammonium sulfate | | | | | | |
| C02 | 0.1 | M | CITRIC ACID | 5 | 2.4 | M | Ammonium sulfate | | | | | | |
| C03 | 0.1 | M | MES monohydrate | 6 | 2.4 | M | Ammonium sulfate | | | | | | |
| C04 | 0.1 | M | HEPES | 7 | 2.4 | M | Ammonium sulfate | | | | | | |
| C05 | 0.1 | M | TRIS | 8 | 2.4 | M | Ammonium sulfate | | | | | | |
| C06 | 0.1 | M | BICINE | 9 | 2.4 | M | Ammonium sulfate | | | | | | |
| D01 | 0.1 | M | CITRIC ACID | 4 | 3 | M | Ammonium sulfate | | | | | | |
| D02 | 0.1 | M | CITRIC ACID | 5 | 3 | M | Ammonium sulfate | | | | | | |
| D03 | 0.1 | M | MES monohydrate | 6 | 3 | M | Ammonium sulfate | | | | | | |
| D04 | 0.1 | M | HEPES | 7 | 3 | M | Ammonium sulfate | | | | | | |
| D05 | 0.1 | M | TRIS | 8 | 3 | M | Ammonium sulfate | | | | | | |
| D06 | 0.1 | M | BICINE | 9 | 3 | M | Ammonium sulfate | | | | | | |

ANNEXE 2B-continued

| Well | Val1 | M/ | Val2 | Reagent1 | M/ | Val3 | Reagent2 | Val4 |
|---|---|---|---|---|---|---|---|---|
| E01 | 4 | | 1 | Malonate | | | | |
| E02 | 4 | M | 1.5 | Malonate | | | | |
| E03 | 4 | M | 1.9 | Malonate | | | | |
| E04 | 4 | M | 2.4 | Malonate | | | | |
| E05 | 4 | M | 2.9 | Malonate | | | | |
| E06 | 9 | M | 3.4 | Malonate | | | | |
| F01 | 5 | M | 1 | Malonate | | | | |
| F02 | 5 | M | 1.5 | Malonate | | | | |
| F03 | 5 | M | 1.9 | Malonate | | | | |
| F04 | 5 | M | 2.4 | Malonate | | | | |
| F05 | 5 | M | 2.9 | Malonate | | | | |
| F06 | 5 | M | 3.4 | Malonate | | | | |
| G01 | 6 | M | 1 | Malonate | | | | |
| G02 | 6 | M | 1.5 | Malonate | | | | |
| G03 | 6 | M | 1.9 | Malonate | | | | |
| G04 | 6 | M | 2.4 | Malonate | | | | |
| G05 | 6 | M | 2.9 | Malonate | | | | |
| G06 | 6 | M | 3.4 | Malonate | | | | |
| H01 | 7 | M | 1 | Malonate | | | | |
| H02 | 7 | M | 1.5 | Malonate | | | | |
| H03 | 7 | M | 1.9 | Malonate | | | | |
| H04 | 7 | M | 2.4 | Malonate | | | | |
| H05 | 7 | M | 2.9 | Malonate | | | | |
| H06 | 7 | M | 3.4 | Malonate | | | | |
| A07 | | M | 0.784 | Sodium phosphate monobasic monohydrate | | 0.016 | | 0 |
| | | | | | | | | 0 |
| | | | | | | | | 0 |
| | | | | | | | | 5 |
| A08 | | M | 0.72 | Sodium phosphate monobasic monohydrate | M | 0.08 | Di-potassium hydrogenophosphate | 5.6 |
| A09 | | M | 0.52 | Sodium phosphate monobasic monohydrate | M | 0.28 | Di-potassium hydrogenophosphate | 6.3 |
| A10 | | | 0.28 | Sodium phosphate monobasic monohydrate | M | 0.52 | Di-potassium hydrogenophosphate | 6.9 |
| A11 | | | 0.12 | Sodium phosphate monobasic monohydrate | M | 0.68 | Di-potassium hydrogenophosphate | 7.5 |
| A12 | | M | G.032 | Sodium phosphate monobasic monohydrate | M | 0.768 | Di-potassium hydrogenophosphate | 8.2 |
| B07 | | M | 0.98 | Sodium phosphate monobasic monohydrate | | 0.02 | Di-potassium hydrogenophosphate | 5 |
| B08 | | M | 0.9 | Sodium phosphate monobasic monohydrate | M | 0.1 | Di-potassium hydrogenophosphate | 5.6 |
| B09 | | M | 0.65 | Sodium phosphate monobasic monohydrate | M | 0.35 | Di-potassium hydrogenophosphate | 6.3 |
| B10 | | M | 0.35 | Sodium phosphate monobasic monohydrate | M | 0.65 | Di-potassium hydrogenophosphate | 6.9 |
| B11 | | M | 0.15 | Sodium phosphate monobasic monohydrate | M | 0.85 | Di-potassium hydrogenophosphate | 7.5 |
| B12 | | | 0.04 | Sodium phosphate monobasic monohydrate | M | 0.96 | Di-potassium hydrogenophosphate | 8.2 |
| C07 | | M | 1.372 | Sodium phosphate monobasic monohydrate | | 0.028 | Di-potassium hydrogenophosphate | 5 |
| C08 | | M | 1.26 | Sodium phosphate monobasic monohydrate | M | 0.14 | Di-potassium hydrogenophosphate | 5.6 |

ANNEXE 2B-continued

| | | | | | | | | |
|---|---|---|---|---|---|---|---|---|
| C09 | | | 0.91 | M | Sodium phosphate monobasic monohydrate | 0.49 | M | Di-potassium hydrogenophosphate | 6.3 |
| C10 | | | 0.49 | M | Sodium phosphate monobasic monohydrate | 0.91 | M | Di-potassium hydrogenophosphate | 6.9 |
| C11 | | | 0.21 | M | Sodium phosphate monobasic monohydrate | 1.19 | M | Di-potassium hydrogenophosphate | 7.5 |
| C12 | | | 0.056 | M | Sodium phosphate monobasic monohydrate | 1.344 | M | Di-potassium hydrogenophosphate | 8.2 |
| D07 | | | 1.764 | M | Sodium phosphate monobasic monohydrate | 0.036 | M | Di-potassium hydrogenophosphate | 5 |
| D08 | | | 1.62 | M | Sodium phosphate monobasic monohydrate | 0.18 | M | Di-potassium hydrogenophosphate | 5.6 |
| D09 | | | 1.17 | M | Sodium phosphate monobasic monohydrate | 0.63 | M | Di-potassium hydrogenophosphate | 6.3 |
| D10 | | | 0.63 | M | Sodium phosphate monobasic monohydrate | 1.17 | M | Di-potassium hydrogenophosphate | 6.9 |
| D11 | | | 0.27 | M | Sodium phosphate monobasic monohydrate | 1.53 | M | Di-potassium hydrogenophosphate | 7.5 |
| D12 | | | 0.072 | M | Sodium phosphate monobasic monohydrate | 1.728 | M | Di-potassium hydrogenophosphate | 8.2 |
| E07 | 0.1 | M | CITRIC ACID | 4 | 0.8 | M | Sodium formate pH4 | |
| E08 | 0.1 | M | CITRIC ACID | 5 | 0.8 | M | Sodium formate pH5 | |
| E09 | 0.1 | M | MES | 6 | 0.8 | M | Sodium formate pH6 | |
| E10 | 0.1 | M | HEPES | 7 | 0.8 | M | Sodium formate pH7 | |
| E11 | 0.1 | M | TRIS | 8 | 0.8 | M | Sodium formate pH8 | |
| E12 | 0.1 | M | BIINE | 9 | 0.8 | M | Sodium formate pH9 | |
| F07 | 0 | M | CITRIC ACID | 4 | 1.6 | M | Sodium formate pH4 | |
| F08 | 0.1 | M | CITRIC ACID | 5 | 1.6 | M | Sodium formate pH5 | |
| F09 | 0.1 | M | MES | 6 | 1.6 | M | Sodium formate pH6 | |
| F10 | 0.1 | M | HEPES | 7 | 1.6 | M | Sodium formate pH7 | |
| F11 | 0.1 | M | TRIS | 8 | 1.6 | M | Sodium formate pH8 | |
| F12 | 0.1 | M | BICINE | 9 | 1.6 | M | Sodium formate pH9 | |
| G07 | 0.1 | M | CITRIC ACID | 4 | 2.4 | M | Sodium formate pH4 | |
| G08 | 0.1 | M | CITRIC ACID | 5 | 2.4 | M | Sodium formate pH5 | |
| G09 | 0.1 | M | MES | 6 | 2.4 | M | Sodium formate pH6 | |
| G10 | 0.1 | M | HEPES | 7 | 2.4 | M | Sodium formate pH7 | |
| G11 | 0.1 | M | TRIS | 8 | 2.4 | M | Sodium formate pH8 | |
| G12 | 0.1 | M | BICINE | 9 | 2.4 | M | Sodium formate pH9 | |
| H07 | 0.1 | M | CITRIC ACID | 4 | 3.2 | M | Sodium formate pH4 | |
| H08 | 0.1 | M | CITRIC ACID | 5 | 3.2 | M | Sodiumformate pH5 | |
| H09 | 0.1 | M | MES | 6 | 3.2 | M | Sodium formate pH6 | |
| H10 | 0.1 | M | HEPES | 7 | 3.2 | M | Sodium formate pH7 | |
| H11 | 0.1 | M | TRIS | 8 | 3.2 | M | Sodium formate pH8 | |
| H12 | 0.1 | M | BICINE | 9 | 3.2 | M | Sodium formate pH9 | |

The invention claimed is:

1. Lathanide complexes formed of a lanthanide ion $Ln^{3+}$ and a ligand of formula (IA-IC), the lanthanide complexes being cationic and having a positive charge greater than or equal to one, the ligand of formula (IA-IC) forming an open coordination sphere comprising aromatic groups with at least seven coordination sites of the lanthanide ion Ln3+, the ligand of formula (IA-IC) being:

(IA)

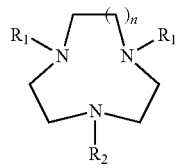

(IB)

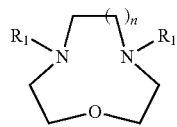

(IC)

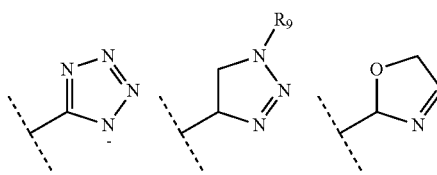

in which:

n is equal to 1, 2 or 3;

$R_2$ is a hydrogen atom or a methyl group or $-CH_2R_5$, where $R_5$ is a phenyl, or pyridinyl;

$R_4$ represents $-H$, $-CH_3$, $-CH_2R_6$; $R_6$ represents a phenyl or pyridinyl group;

$R_1$ represents:

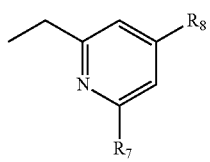

with:

$R_7$ which represents $-COO^-$, $-CONH_2$, $-CONHR_9$, $-PR_9OO^-$, or a selected group chosen from:

with $R_9$ which represents a hydrogen atom, a methyl, ethyl or phenyl group; and $R_8$ which represents a hydrogen, fluorine, chlorine, bromine or iodine atom, an $-OH$ or $-NH_2$; and their salts with an anion, their solvates and hydrates.

2. Complexes according to claim 1 in the form of a salt with an anion chosen from: $Cl^-$, $Br^-$, $I^-$, $OH^-$, $NO_3^-$, triflate, $PF_6^-$, $SbF_6^-$, $B(Ph)_4^-$, $BF_4^-$, sulphates, carbonates, phosphates and carboxylates.

3. Complexes according to claim 1 formed with a ligand corresponding to the formula (IA):

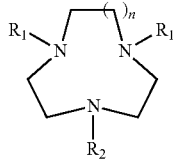
(IA)

wherein n=1 and $R_2$=H, and $R_1$ represents:

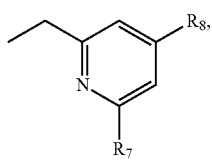

as well as their salts with an anion, their solvates and hydrates.

4. Complexes according to claim 1 characterized in that $R_1$ represents:

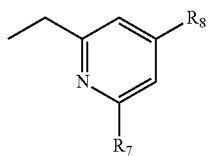

with:
$R_7$ which represents COO⁻ or —$PR_9OO^-$ with $R_9$ which represents a group methyl or ethyl; or $R_7$ which represents

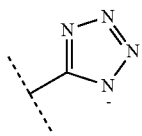

$R_8$ which represents a hydrogen, fluorine, chlorine, bromine or iodine atom;
as well as their salts with an anion, their solvates and hydrates.

5. Complexes according to claim 1, chosen from among complexes of formula:

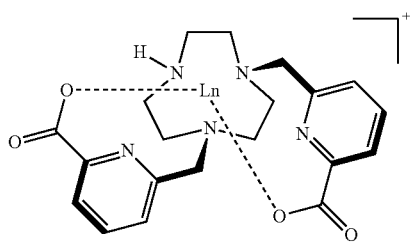

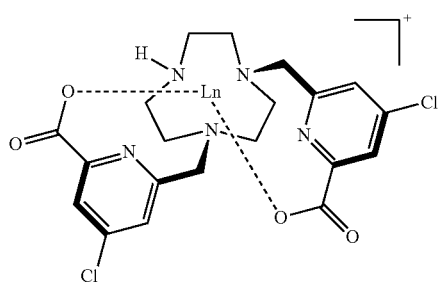

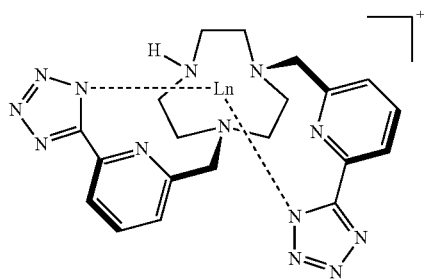

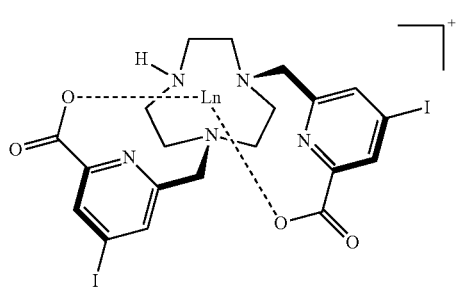

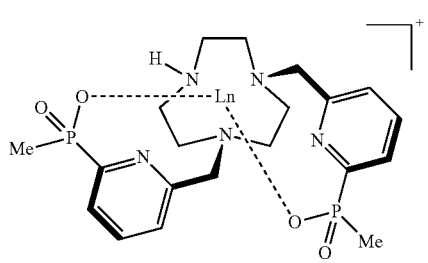

as well as their salts with an anion, in particular their hydrochloride salt, their solvates and hydrates.

6. Complexes according to claim 1, with a lanthanide ion $Ln^{3+}$, Ln being Sm, Eu, Gd, Tb, Dy, Ho, Er, Tm, Yb or Lu, with Eu, Tb, Yb and Lu being preferred.

* * * * *

SEQUENCE LISTING

<160> NUMBER OF SEQ ID NOS: 7

<210> SEQ ID NO 1
<211> LENGTH: 129
<212> TYPE: PRT
<213> ORGANISM: Gallus gallus
<220> FEATURE:
<223> OTHER INFORMATION: Lysozyme HEWL

<400> SEQUENCE: 1

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 2
<211> LENGTH: 207
<212> TYPE: PRT
<213> ORGANISM: Thaumatococcus daniellii
<220> FEATURE:
<223> OTHER INFORMATION: Thaumatine

<400> SEQUENCE: 2

Ala Thr Phe Glu Ile Val Asn Arg Cys Ser Tyr Thr Val Trp Ala Ala
1               5                   10                  15

Ala Ser Lys Gly Asp Ala Ala Leu Asp Ala Gly Gly Arg Gln Leu Asn
                20                  25                  30

Ser Gly Glu Ser Trp Thr Ile Asn Val Glu Pro Gly Thr Asn Gly Gly
            35                  40                  45

Lys Ile Trp Ala Arg Thr Asp Cys Tyr Phe Asp Asp Ser Gly Ser Gly
        50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Ile Asp Ile Ser Asn Ile Lys Gly Phe Asn Val Pro Met
            100                 105                 110

Asn Phe Ser Pro Thr Thr Arg Gly Cys Arg Gly Val Arg Cys Ala Ala
        115                 120                 125

Asp Ile Val Gly Gln Cys Pro Ala Lys Leu Lys Ala Pro Gly Gly Gly
    130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Arg Leu

```
                    165                 170                 175
Cys Pro Asp Ala Phe Ser Tyr Val Leu Asp Lys Pro Thr Thr Val Thr
                180                 185                 190

Cys Pro Gly Ser Ser Asn Tyr Arg Val Thr Phe Cys Pro Thr Ala
            195                 200                 205

<210> SEQ ID NO 3
<211> LENGTH: 279
<212> TYPE: PRT
<213> ORGANISM: Tritirachium album
<220> FEATURE:
<223> OTHER INFORMATION: Proteinase K

<400> SEQUENCE: 3

Ala Ala Gln Thr Asn Ala Pro Trp Gly Leu Ala Arg Ile Ser Thr
1               5                   10                  15

Ser Pro Gly Thr Ser Thr Tyr Tyr Tyr Asp Glu Ser Ala Gly Gln Gly
                20                  25                  30

Ser Cys Val Tyr Val Ile Asp Thr Gly Ile Glu Ala Ser His Pro Glu
            35                  40                  45

Phe Glu Gly Arg Ala Gln Met Val Lys Thr Tyr Tyr Tyr Ser Ser Arg
50                  55                  60

Asp Gly Asn Gly His Gly Thr His Cys Ala Gly Thr Val Gly Ser Arg
65                  70                  75                  80

Thr Tyr Gly Val Ala Lys Lys Thr Gln Leu Phe Gly Val Lys Val Leu
                85                  90                  95

Asp Asp Asn Gly Ser Gly Gln Tyr Ser Thr Ile Ile Ala Gly Met Asp
            100                 105                 110

Phe Val Ala Ser Asp Lys Asn Asn Arg Asn Cys Pro Lys Gly Val Val
        115                 120                 125

Ala Ser Leu Ser Leu Gly Gly Gly Tyr Ser Ser Ser Val Asn Ser Ala
130                 135                 140

Ala Ala Arg Leu Gln Ser Ser Gly Val Met Val Ala Val Ala Ala Gly
145                 150                 155                 160

Asn Asn Asn Ala Asp Ala Arg Asn Tyr Ser Pro Ala Ser Glu Pro Ser
                165                 170                 175

Val Cys Thr Val Gly Ala Ser Asp Arg Tyr Asp Arg Arg Ser Ser Phe
            180                 185                 190

Ser Asn Tyr Gly Ser Val Leu Asp Ile Phe Gly Pro Gly Thr Asp Ile
        195                 200                 205

Leu Ser Thr Trp Ile Gly Gly Ser Thr Arg Ser Ile Ser Gly Thr Ser
210                 215                 220

Met Ala Thr Pro His Val Ala Gly Leu Ala Ala Tyr Leu Met Thr Leu
225                 230                 235                 240

Gly Lys Thr Thr Ala Ala Ser Ala Cys Arg Tyr Ile Ala Asp Thr Ala
                245                 250                 255

Asn Lys Gly Asp Leu Ser Asn Ile Pro Phe Gly Thr Val Asn Leu Leu
            260                 265                 270

Ala Tyr Asn Asn Tyr Gln Ala
        275

<210> SEQ ID NO 4
<211> LENGTH: 336
<212> TYPE: PRT
<213> ORGANISM: Pyrococcus furiosus
<220> FEATURE:
<223> OTHER INFORMATION: Glyoxylate and Hydroxypyruvate Reductase
```

<400> SEQUENCE: 4

```
Met Lys Pro Lys Val Phe Ile Thr Arg Ala Ile Pro Glu Asn Gly Ile
1               5                   10                  15

Asn Met Leu Glu Glu Glu Phe Glu Val Glu Val Trp Glu Glu Glu Arg
            20                  25                  30

Glu Ile Pro Arg Glu Lys Leu Leu Glu Lys Val Lys Asp Val Asp Ala
        35                  40                  45

Leu Val Thr Met Leu Ser Glu Arg Ile Asp Gln Glu Val Phe Glu Asn
    50                  55                  60

Ala Pro Arg Leu Arg Ile Val Ala Asn Tyr Ala Val Gly Tyr Asp Asn
65                  70                  75                  80

Ile Asp Val Glu Glu Ala Thr Arg Arg Gly Ile Tyr Val Thr Asn Thr
                85                  90                  95

Pro Asp Val Leu Thr Asn Ala Thr Ala Asp His Ala Phe Ala Leu Leu
            100                 105                 110

Leu Ala Thr Ala Arg His Val Val Lys Gly Asp Lys Phe Val Arg Ser
        115                 120                 125

Gly Glu Trp Lys Arg Lys Gly Ile Ala Trp His Pro Lys Trp Phe Leu
130                 135                 140

Gly Tyr Glu Leu Tyr Gly Lys Thr Ile Gly Ile Val Gly Phe Gly Arg
145                 150                 155                 160

Ile Gly Gln Ala Ile Ala Arg Arg Ala Lys Gly Phe Asn Met Arg Ile
                165                 170                 175

Leu Tyr Tyr Ser Arg Thr Arg Lys Ser Gln Ala Glu Lys Glu Leu Gly
            180                 185                 190

Ala Glu Tyr Arg Pro Leu Glu Glu Val Leu Lys Glu Ser Asp Phe Val
        195                 200                 205

Ile Leu Ala Val Pro Leu Thr Lys Glu Thr Met Tyr Met Ile Asn Glu
210                 215                 220

Glu Arg Leu Lys Leu Met Lys Pro Thr Ala Ile Leu Val Asn Ile Ala
225                 230                 235                 240

Arg Gly Lys Val Val Asp Thr Lys Ala Leu Ile Lys Ala Leu Lys Glu
                245                 250                 255

Gly Trp Ile Ala Gly Ala Gly Leu Asp Val Phe Glu Glu Pro Tyr
            260                 265                 270

Tyr Asn Glu Glu Leu Phe Ser Leu Asp Asn Val Val Leu Thr Pro His
        275                 280                 285

Ile Gly Ser Ala Thr Phe Glu Ala Arg Glu Ala Met Ala Glu Leu Val
290                 295                 300

Ala Arg Asn Leu Ile Ala Phe Lys Arg Gly Glu Ile Pro Pro Thr Leu
305                 310                 315                 320

Val Asn Lys Glu Val Ile Lys Ile Arg Lys Pro Gly Phe Asn Glu Gln
                325                 330                 335
```

<210> SEQ ID NO 5
<211> LENGTH: 166
<212> TYPE: PRT
<213> ORGANISM: Pyrococcus horikoshii OT3
<220> FEATURE:
<223> OTHER INFORMATION: Protease 1

<400> SEQUENCE: 5

```
Met Lys Val Leu Phe Leu Thr Ala Asn Glu Phe Glu Asp Val Glu Leu
1               5                   10                  15
```

```
Ile Tyr Pro Tyr His Arg Leu Lys Glu Gly His Glu Val Tyr Ile
                20                  25                  30

Ala Ser Phe Glu Arg Gly Thr Ile Thr Gly Lys His Gly Tyr Ser Val
            35                  40                  45

Lys Val Asp Leu Thr Phe Asp Lys Val Asn Pro Glu Glu Phe Asp Ala
 50                  55                  60

Leu Val Leu Pro Gly Gly Arg Ala Pro Glu Arg Val Arg Leu Asn Glu
 65                  70                  75                  80

Lys Ala Val Ser Ile Ala Arg Lys Met Phe Ser Glu Gly Lys Pro Val
                85                  90                  95

Ala Ser Ile Cys His Gly Pro Gln Ile Leu Ile Ser Ala Gly Val Leu
            100                 105                 110

Arg Gly Arg Lys Gly Thr Ser Tyr Pro Gly Ile Lys Asp Asp Met Ile
            115                 120                 125

Asn Ala Gly Val Glu Trp Val Asp Ala Glu Val Val Val Asp Gly Asn
130                 135                 140

Trp Val Ser Ser Arg Val Pro Ala Asp Leu Tyr Ala Trp Met Arg Glu
145                 150                 155                 160

Phe Val Lys Leu Leu Lys
                165
```

<210> SEQ ID NO 6
<211> LENGTH: 464
<212> TYPE: PRT
<213> ORGANISM: Artificial Sequence
<220> FEATURE:
<223> OTHER INFORMATION: phage T5

<400> SEQUENCE: 6

```
Met Ser Leu Gln Leu Leu Arg Asn Thr Arg Ile Phe Val Ser Thr Val
 1               5                  10                  15

Lys Thr Gly His Asn Lys Thr Asn Thr Gln Glu Ile Leu Val Gln Asp
                20                  25                  30

Asp Ile Ser Trp Gly Gln Asp Ser Asn Ser Thr Asp Ile Thr Val Asn
            35                  40                  45

Glu Ala Gly Pro Arg Pro Thr Arg Gly Ser Lys Arg Phe Asn Asp Ser
 50                  55                  60

Leu Asn Ala Ala Glu Trp Ser Phe Ser Thr Tyr Ile Leu Pro Tyr Lys
 65                  70                  75                  80

Asp Lys Asn Thr Ser Lys Gln Ile Val Pro Asp Tyr Met Leu Trp His
                85                  90                  95

Ala Leu Ser Ser Gly Arg Ala Ile Asn Leu Glu Gly Thr Thr Gly Ala
            100                 105                 110

His Asn Asn Ala Thr Asn Phe Met Val Asn Phe Lys Asp Asn Ser Tyr
            115                 120                 125

His Glu Leu Ala Met Leu His Ile Tyr Ile Leu Thr Asp Lys Thr Trp
            130                 135                 140

Ser Tyr Ile Asp Ser Cys Gln Ile Asn Gln Ala Glu Val Asn Val Asp
145                 150                 155                 160

Ile Glu Asp Ile Gly Arg Val Thr Trp Ser Gly Asn Gly Asn Gln Leu
                165                 170                 175

Ile Pro Leu Asp Glu Gln Pro Phe Asp Pro Asp Gln Ile Gly Ile Asp
            180                 185                 190

Asp Glu Thr Tyr Met Thr Ile Gln Gly Ser Tyr Ile Lys Asn Lys Leu
            195                 200                 205
```

```
Thr Ile Leu Lys Ile Lys Asp Met Asp Thr Asn Lys Ser Tyr Asp Ile
    210                 215                 220

Pro Ile Thr Gly Gly Thr Phe Thr Ile Asn Asn Asn Ile Thr Tyr Leu
225                 230                 235                 240

Thr Pro Asn Val Met Ser Arg Val Thr Ile Pro Ile Gly Ser Phe Thr
                245                 250                 255

Gly Ala Phe Glu Leu Thr Gly Ser Leu Thr Ala Tyr Leu Asn Asp Lys
                260                 265                 270

Ser Leu Gly Ser Met Glu Leu Tyr Lys Asp Leu Ile Lys Thr Leu Lys
                275                 280                 285

Val Val Asn Arg Phe Glu Ile Ala Leu Val Leu Gly Gly Glu Tyr Asp
290                 295                 300

Asp Glu Arg Pro Ala Ala Ile Leu Val Ala Lys Gln Ala His Val Asn
305                 310                 315                 320

Ile Pro Thr Ile Glu Thr Asp Asp Val Leu Gly Thr Ser Val Glu Phe
                325                 330                 335

Lys Ala Ile Pro Ser Asp Leu Asp Ala Gly Asp Glu Gly Tyr Leu Gly
                340                 345                 350

Phe Ser Ser Lys Tyr Thr Arg Thr Thr Ile Asn Asn Leu Ile Val Asn
                355                 360                 365

Gly Asp Gly Ala Thr Asp Ala Val Thr Ala Ile Thr Val Lys Ser Ala
370                 375                 380

Gly Asn Val Thr Thr Leu Asn Arg Ser Ala Thr Leu Gln Met Ser Val
385                 390                 395                 400

Glu Val Thr Pro Ser Ser Ala Arg Asn Lys Glu Val Thr Trp Ala Ile
                405                 410                 415

Thr Ala Gly Asp Ala Ala Thr Ile Asn Ala Thr Gly Leu Leu Arg Ala
                420                 425                 430

Asp Ala Ser Lys Thr Gly Ala Val Thr Val Glu Ala Thr Ala Lys Asp
                435                 440                 445

Gly Ser Gly Val Lys Gly Thr Lys Val Ile Thr Val Thr Ala Gly Gly
                450                 455                 460

<210> SEQ ID NO 7
<211> LENGTH: 304
<212> TYPE: PRT
<213> ORGANISM: Artificial Sequence
<220> FEATURE:
<223> OTHER INFORMATION: ANC80 Malate Dehydrogenase

<400> SEQUENCE: 7

Met Thr Lys Val Ser Val Val Gly Ala Ala Gly Thr Val Gly Ala Ala
1               5                   10                  15

Ala Gly Tyr Asn Leu Ala Leu Arg Asp Ile Ala Asp Glu Leu Val Phe
                20                  25                  30

Val Asp Ile Pro Asp Gln Glu Asp Val Thr Ile Gly Gln Ala Ala Asp
            35                  40                  45

Thr Asn His Gly Val Ala Tyr Asp Ser Asn Thr Thr Val Arg Gln Gly
        50                  55                  60

Gly Tyr Glu Asp Thr Ala Gly Ser Asp Val Val Ile Thr Ala Gly
65                  70                  75                  80

Ile Pro Arg Gln Pro Gly Gln Thr Arg Ile Asp Leu Ala Gly Asp Asn
                85                  90                  95

Ala Pro Ile Met Glu Asp Ile Gly Ser Ser Leu Ala Glu His Asn Asp
            100                 105                 110
```

```
Asp Phe Val Thr Ile Thr Thr Ser Asn Pro Val Asp Leu Leu Asn Arg
            115             120             125

His Leu Tyr Glu Thr Gly Asp Arg Ala Arg Glu Lys Val Ile Gly Phe
            130             135             140

Gly Gly Arg Leu Asp Ser Ala Arg Phe Arg Tyr Val Leu Ser Gln Arg
145             150             155             160

Phe Asp Ala Pro Val Gln Asn Val Glu Ala Thr Ile Leu Gly Glu His
            165             170             175

Gly Asp Ala Gln Val Pro Val Phe Ser Lys Val Arg Val Asp Gly Thr
            180             185             190

Asp Pro Glu Phe Ser Ala Asp Glu Lys Glu Glu Ile Leu Gly Asp Leu
            195             200             205

Gln Glu Ser Ala Met Asp Val Ile Glu Arg Lys Gly Ala Thr Gln Trp
    210             215             220

Gly Pro Ala Thr Gly Val Ala His Met Val Glu Ala Val Leu His Asp
225             230             235             240

Thr Gly Glu Val Leu Pro Gly Ser Val Val Leu Asp Gly Glu Phe Gly
            245             250             255

His Glu Asp Thr Ala Phe Gly Val Pro Val Lys Leu Gly Ser Asn Gly
            260             265             270

Val Glu Glu Val Val Glu Trp Asp Leu Asp Asp Tyr Glu Gln Asp Leu
    275             280             285

Met Asp Asp Ala Ala Glu Lys Leu Ser Asp Gln Tyr Asp Lys Ile Ala
    290             295             300
```